US010219811B2

(12) United States Patent
Haider et al.

(10) Patent No.: US 10,219,811 B2
(45) Date of Patent: Mar. 5, 2019

(54) ON-BOARD TOOL TRACKING SYSTEM AND METHODS OF COMPUTER ASSISTED SURGERY

(75) Inventors: Hani Haider, Carter Lake, IA (US); Ibrahim Al-Shawi, Amman (JO); Osvaldo Andres Barrera, Omaha, NE (US)

(73) Assignee: Board of Regents of the University of Nebraska, Lincoln, NE (US)

(*) Notice: Subject to any disclaimer, the term of this patent is extended or adjusted under 35 U.S.C. 154(b) by 1101 days.

(21) Appl. No.: 14/128,213

(22) PCT Filed: Jun. 27, 2012

(86) PCT No.: PCT/US2012/044486
§ 371 (c)(1),
(2), (4) Date: Apr. 17, 2014

(87) PCT Pub. No.: WO2013/052187
PCT Pub. Date: Apr. 11, 2013

(65) Prior Publication Data
US 2014/0236159 A1 Aug. 21, 2014

Related U.S. Application Data

(60) Provisional application No. 61/501,489, filed on Jun. 27, 2011.

(51) Int. Cl.
*A61B 34/20* (2016.01)
*A61B 17/17* (2006.01)
(Continued)

(52) U.S. Cl.
CPC ........ *A61B 17/1703* (2013.01); *A61B 17/142* (2016.11); *A61B 17/1626* (2013.01);
(Continued)

(58) Field of Classification Search
CPC .............. A61B 17/1703; A61B 17/142; A61B 17/1626; A61B 17/1675; A61B 17/1764;
(Continued)

(56) References Cited

U.S. PATENT DOCUMENTS 3,730,277 A  5/1973 Brugler
3,752,161 A  8/1973 Bent
(Continued)

FOREIGN PATENT DOCUMENTS

CN  1162251 A  10/1997
CN  1689518 A  11/2005
(Continued)

OTHER PUBLICATIONS

Brisson et al., Precision Freehand Sculpting of Bone; Lecture Notes in Computer Science; vol. 3217; MICCAI 2004; 7th International Conf. Proceedings, Part II; Saint-Malo, France; pp. 105-112; Sep. 26-29, 2004.
(Continued)

*Primary Examiner* — Zade Coley
*Assistant Examiner* — Jessica Weiss
(74) *Attorney, Agent, or Firm* — Shay Glenn LLP

(57) ABSTRACT

A number of improvements are provided relating to computer aided surgery utilizing an on tool tracking system. The various improvements relate generally to both the methods used during computer aided surgery and the devices used during such procedures. Other improvements relate to the structure of the tools used during a procedure and how the tools can be controlled using the OTT device. Still other improvements relate to methods of providing feedback during a procedure to improve either the efficiency or quality, or both, for a procedure including the rate of and type of data processed depending upon a CAS mode.

24 Claims, 58 Drawing Sheets

LID REMOVED

(51) Int. Cl.

|  |  |
|---|---|
| *A61B 17/16* | (2006.01) |
| *A61B 34/32* | (2016.01) |
| *A61B 34/30* | (2016.01) |
| *A61B 34/00* | (2016.01) |
| *A61B 17/14* | (2006.01) |
| *A61B 34/10* | (2016.01) |
| *A61B 90/00* | (2016.01) |

(52) U.S. Cl.
CPC ...... *A61B 17/1675* (2013.01); *A61B 17/1764* (2013.01); *A61B 34/20* (2016.02); *A61B 34/30* (2016.02); *A61B 34/32* (2016.02); *A61B 34/76* (2016.02); *A61B 2034/102* (2016.02); *A61B 2034/2057* (2016.02); *A61B 2090/064* (2016.02); *A61B 2090/366* (2016.02); *A61B 2090/371* (2016.02)

(58) Field of Classification Search
CPC ......... A61B 34/20; A61B 34/76; A61B 34/30; A61B 34/32; A61B 2034/102; A61B 2034/2055; A61B 2034/2057; A61B 2090/064; A61B 2090/371; A61B 2090/366
USPC .................................. 606/130, 79–85, 86 R
See application file for complete search history.

(56) References Cited

U.S. PATENT DOCUMENTS

| | | |
|---|---|---|
| 3,932,923 A | 1/1976 | DiMatteo |
| 4,089,084 A | 5/1978 | Droz |
| 4,204,145 A | 5/1980 | Hevenor, Jr. et al. |
| 4,269,615 A | 5/1981 | Zboralski et al. |
| 4,291,708 A | 9/1981 | Frei et al. |
| 4,337,566 A | 7/1982 | DiMatteo et al. |
| 4,423,075 A | 12/1983 | Dvornik et al. |
| 4,436,684 A | 3/1984 | White |
| 4,458,694 A | 7/1984 | Sollish et al. |
| 4,476,609 A | 10/1984 | Loudin |
| 4,640,120 A | 2/1987 | Garritano et al. |
| 4,660,573 A | 4/1987 | Brumbach |
| 4,660,970 A | 4/1987 | Ferrano |
| 4,668,087 A | 5/1987 | Strandell et al. |
| 4,725,965 A | 2/1988 | Keenan |
| 4,742,819 A | 5/1988 | George |
| 4,899,095 A | 2/1990 | Kishi et al. |
| 4,907,169 A | 3/1990 | Lovoi |
| 4,963,147 A | 10/1990 | Agee et al. |
| 4,977,886 A | 12/1990 | Takehana et al. |
| 4,995,877 A | 2/1991 | Ams et al. |
| 5,006,999 A | 4/1991 | Kuno et al. |
| 5,086,401 A | 2/1992 | Glassman et al. |
| 5,152,799 A | 10/1992 | Lyons |
| 5,188,093 A | 2/1993 | Lafferty et al. |
| 5,190,549 A | 3/1993 | Miller et al. |
| 5,190,550 A | 3/1993 | Miller et al. |
| 5,230,623 A | 7/1993 | Guthrie et al. |
| 5,261,404 A | 11/1993 | Mick et al. |
| 5,263,988 A | 11/1993 | Huebner |
| 5,283,642 A | 2/1994 | Sarr |
| 5,321,353 A | 6/1994 | Furness |
| 5,383,454 A | 1/1995 | Bucholz |
| 5,389,101 A | 2/1995 | Heilbrun et al. |
| 5,411,500 A | 5/1995 | Lafferty et al. |
| 5,429,502 A | 7/1995 | Cooper et al. |
| 5,433,717 A | 7/1995 | Rubinsky et al. |
| 5,449,363 A | 9/1995 | Brust et al. |
| 5,458,443 A | 10/1995 | Belge et al. |
| 5,524,180 A | 6/1996 | Wang et al. |
| 5,548,694 A | 8/1996 | Gibson |
| 5,562,448 A | 10/1996 | Mushabac |
| 5,601,561 A | 2/1997 | Terry et al. |
| 5,603,318 A | 2/1997 | Heilbrun et al. |
| 5,611,025 A | 3/1997 | Lorensen et al. |
| 5,617,857 A | 4/1997 | Chader et al. |
| 5,622,170 A | 4/1997 | Schulz |
| 5,626,594 A | 5/1997 | Smith |
| 5,632,758 A | 5/1997 | Sklar |
| 5,668,061 A | 9/1997 | Herko et al. |
| 5,669,921 A | 9/1997 | Berman et al. |
| 5,676,673 A | 10/1997 | Ferre et al. |
| 5,682,886 A | 11/1997 | Delp et al. |
| 5,688,281 A | 11/1997 | Cripe et al. |
| 5,694,013 A | 12/1997 | Stewart et al. |
| 5,706,408 A | 1/1998 | Pryor |
| 5,715,836 A | 2/1998 | Kliegis et al. |
| 5,725,580 A | 3/1998 | Cloutier et al. |
| 5,732,992 A | 3/1998 | Mauldin |
| 5,735,283 A | 4/1998 | Snook |
| 5,740,802 A | 4/1998 | Nafis et al. |
| 5,748,767 A | 5/1998 | Raab |
| 5,751,011 A | 5/1998 | McLaughlin et al. |
| RE35,816 E | 6/1998 | Schulz |
| 5,769,087 A | 6/1998 | Westphal et al. |
| 5,769,092 A | 6/1998 | Williamson |
| 5,776,136 A | 7/1998 | Sahay et al. |
| 5,777,720 A | 7/1998 | Shapiro et al. |
| 5,781,195 A | 7/1998 | Marvin |
| 5,788,636 A | 8/1998 | Curley |
| 5,792,147 A | 8/1998 | Evans et al. |
| 5,806,518 A | 9/1998 | Mittelstadt |
| 5,817,105 A | 10/1998 | Van Der Brug |
| 5,820,627 A | 10/1998 | Rosen et al. |
| 5,824,085 A | 10/1998 | Sahay et al. |
| 5,827,178 A | 10/1998 | Berall |
| 5,838,882 A | 11/1998 | Gan et al. |
| 5,846,244 A | 12/1998 | Cripe |
| 5,880,976 A | 3/1999 | DiGioia, III et al. |
| 5,882,206 A | 3/1999 | Gillio |
| 5,902,239 A | 5/1999 | Buurman |
| 5,907,395 A | 5/1999 | Schulz et al. |
| 5,920,395 A | 7/1999 | Schulz |
| 5,921,992 A | 7/1999 | Costales et al. |
| 5,925,064 A | 7/1999 | Meyers et al. |
| 5,928,137 A | 7/1999 | Green |
| 5,951,475 A | 9/1999 | Gueziec et al. |
| 5,954,648 A | 9/1999 | Van Der Brug |
| 5,956,253 A | 9/1999 | Gottschalk |
| 5,971,767 A | 10/1999 | Kaufman et al. |
| 5,973,678 A | 10/1999 | Stewart et al. |
| 5,987,960 A | 11/1999 | Messner et al. |
| 5,995,738 A | 11/1999 | DiGioia, III et al. |
| 6,002,859 A | 12/1999 | DiGioia, III et al. |
| 6,003,415 A | 12/1999 | Turner et al. |
| 6,006,126 A | 12/1999 | Cosman |
| 6,006,127 A | 12/1999 | Van Der Brug et al. |
| 6,011,581 A | 1/2000 | Swift et al. |
| 6,014,145 A | 1/2000 | Bardon et al. |
| 6,021,343 A | 2/2000 | Foley et al. |
| 6,033,415 A | 3/2000 | Mittelstadt et al. |
| 6,038,467 A | 3/2000 | De Bliek et al. |
| 6,054,992 A | 4/2000 | Gibson |
| 6,059,494 A | 5/2000 | Susnjara |
| 6,063,095 A | 5/2000 | Wang et al. |
| 6,069,634 A | 5/2000 | Gibson |
| 6,080,162 A | 6/2000 | Dye et al. |
| 6,080,181 A | 6/2000 | Jensen et al. |
| 6,083,163 A | 7/2000 | Wegner et al. |
| 6,084,979 A | 7/2000 | Kanade et al. |
| 6,086,544 A | 7/2000 | Hibner et al. |
| 6,091,453 A | 7/2000 | Coan et al. |
| 6,094,007 A | 7/2000 | Faul et al. |
| 6,097,168 A | 8/2000 | Katoh et al. |
| 6,106,457 A | 8/2000 | Perkins et al. |
| 6,112,113 A | 8/2000 | Van Der Brug et al. |
| 6,120,462 A | 9/2000 | Hibner et al. |
| 6,131,097 A | 10/2000 | Peurach et al. |
| 6,141,104 A | 10/2000 | Schulz et al. |
| 6,151,009 A | 11/2000 | Kanade et al. |
| 6,158,136 A | 12/2000 | Gotz et al. |
| 6,159,200 A | 12/2000 | Verdura et al. |
| 6,167,292 A | 12/2000 | Badano et al. |

(56) References Cited

U.S. PATENT DOCUMENTS

| | | |
|---|---|---|
| 6,167,295 A | 12/2000 | Cosman |
| 6,167,296 A | 12/2000 | Shahidi |
| 6,176,837 B1 | 1/2001 | Foxlin |
| 6,187,012 B1 | 2/2001 | Masini |
| 6,190,395 B1 | 2/2001 | Williams |
| 6,192,777 B1 | 2/2001 | Williams et al. |
| 6,198,794 B1 | 3/2001 | Peshkin et al. |
| 6,203,497 B1 | 3/2001 | Dekel et al. |
| 6,205,411 B1 | 3/2001 | DiGioia, III et al. |
| 6,214,018 B1 | 4/2001 | Kreizman et al. |
| 6,216,029 B1 | 4/2001 | Paltieli |
| 6,226,548 B1 | 5/2001 | Foley et al. |
| 6,228,089 B1 | 5/2001 | Wahrburg |
| 6,236,875 B1 | 5/2001 | Bucholz et al. |
| 6,245,084 B1 | 6/2001 | Mark et al. |
| 6,262,738 B1 | 7/2001 | Gibson et al. |
| 6,263,230 B1 | 7/2001 | Haynor et al. |
| 6,273,862 B1 | 8/2001 | Privitera et al. |
| 6,285,902 B1 | 9/2001 | Kienzle, III et al. |
| 6,298,262 B1 | 10/2001 | Franck et al. |
| 6,314,310 B1 | 11/2001 | Ben Haim et al. |
| 6,314,311 B1 | 11/2001 | Williams et al. |
| 6,317,616 B1 | 11/2001 | Glossop |
| 6,319,286 B1 | 11/2001 | Fernandez et al. |
| 6,322,567 B1 | 11/2001 | Mittelstadt et al. |
| 6,329,778 B1 | 12/2001 | Culp et al. |
| 6,332,891 B1 | 12/2001 | Himes |
| 6,336,931 B1 | 1/2002 | Hsu et al. |
| 6,347,460 B1 | 2/2002 | Forrer et al. |
| 6,351,573 B1 | 2/2002 | Schneider |
| 6,368,354 B2 | 4/2002 | Burstein et al. |
| 6,390,982 B1 | 5/2002 | Bova et al. |
| 6,423,063 B1 | 7/2002 | Bonutti |
| 6,424,885 B1 | 7/2002 | Niemeyer et al. |
| 6,428,547 B1 | 8/2002 | Vilsmeier et al. |
| 6,430,434 B1 | 8/2002 | Mittelstadt |
| 6,432,112 B2 | 8/2002 | Brock et al. |
| 6,434,416 B1 | 8/2002 | Mizoguchi et al. |
| 6,442,416 B1 | 8/2002 | Schultz |
| 6,442,417 B1 | 8/2002 | Shahidi et al. |
| 6,450,978 B1 | 9/2002 | Brosseau et al. |
| 6,453,190 B1 | 9/2002 | Acker et al. |
| 6,456,868 B2 | 9/2002 | Saito et al. |
| 6,468,289 B1 | 10/2002 | Bonutti |
| 6,470,207 B1 | 10/2002 | Simon et al. |
| 6,474,159 B1 | 11/2002 | Foxlin et al. |
| 6,478,802 B2 | 11/2002 | Kienzle, III et al. |
| 6,491,701 B2 | 12/2002 | Tierney et al. |
| 6,497,134 B1 | 12/2002 | Faul et al. |
| 6,501,997 B1 | 12/2002 | Kakino |
| 6,503,195 B1 | 1/2003 | Keller et al. |
| 6,503,267 B2 | 1/2003 | Bonutti et al. |
| 6,503,277 B2 | 1/2003 | Bonutti |
| 6,511,323 B1 | 1/2003 | Wilkinson |
| 6,514,259 B2 | 2/2003 | Picard et al. |
| 6,520,228 B1 | 2/2003 | Kennedy et al. |
| 6,522,906 B1 | 2/2003 | Salisbury et al. |
| 6,529,765 B1 | 3/2003 | Franck et al. |
| 6,546,277 B1 | 4/2003 | Franck et al. |
| 6,546,279 B1 | 4/2003 | Bova et al. |
| 6,550,997 B1 | 4/2003 | King et al. |
| 6,552,722 B1 | 4/2003 | Shih et al. |
| 6,575,969 B1 | 6/2003 | Rittman, III et al. |
| 6,575,982 B1 | 6/2003 | Bonutti |
| 6,584,339 B2 | 6/2003 | Galloway et al. |
| 6,591,698 B1 | 7/2003 | Carlsson et al. |
| 6,599,247 B1 | 7/2003 | Stetten |
| 6,608,688 B1 | 8/2003 | Faul et al. |
| 6,620,181 B1 | 9/2003 | Bonutti |
| 6,620,198 B2 | 9/2003 | Burstein et al. |
| 6,635,073 B2 | 10/2003 | Bonutti |
| 6,638,233 B2 | 10/2003 | Corvi et al. |
| 6,640,127 B1 | 10/2003 | Kosaka et al. |
| 6,640,128 B2 | 10/2003 | Vilsmeier et al. |
| 6,647,840 B2 | 11/2003 | Luik |
| 6,659,939 B2 | 12/2003 | Moll et al. |
| 6,662,036 B2 | 12/2003 | Cosman |
| 6,669,635 B2 | 12/2003 | Kessman et al. |
| 6,669,710 B2 | 12/2003 | Moutafis et al. |
| 6,676,669 B2 | 1/2004 | Charles et al. |
| 6,678,552 B2 | 1/2004 | Pearlman |
| 6,681,129 B2 | 1/2004 | Matsuzaki et al. |
| 6,685,711 B2 | 2/2004 | Axelson, Jr. et al. |
| 6,690,964 B2 | 2/2004 | Bieger et al. |
| 6,702,821 B2 | 3/2004 | Bonutti |
| 6,711,432 B1 | 3/2004 | Krause et al. |
| 6,718,194 B2 | 4/2004 | Kienzle, III |
| 6,725,080 B2 | 4/2004 | Melkent et al. |
| 6,730,128 B2 | 5/2004 | Burstein |
| 6,738,657 B1 | 5/2004 | Franklin et al. |
| 6,747,651 B1 | 6/2004 | Tan et al. |
| 6,757,582 B2 | 6/2004 | Brisson et al. |
| 6,770,078 B2 | 8/2004 | Bonutti |
| 6,780,007 B1 | 8/2004 | Coffin |
| 6,782,287 B2 | 8/2004 | Grzeszczuk et al. |
| 6,788,999 B2 | 9/2004 | Green |
| 6,796,988 B2 | 9/2004 | Melkent et al. |
| 6,816,755 B2 | 11/2004 | Habibi et al. |
| 6,823,207 B1 | 11/2004 | Jensen et al. |
| 6,827,723 B2 | 12/2004 | Carson |
| 6,829,384 B2 | 12/2004 | Schneiderman et al. |
| 6,837,892 B2 | 1/2005 | Shoham |
| 6,847,394 B1 | 1/2005 | Hansen et al. |
| 6,859,661 B2 | 2/2005 | Tuke |
| 6,892,090 B2 | 5/2005 | Verard et al. |
| 6,917,827 B2 | 7/2005 | Kienzle, III |
| 6,920,347 B2 | 7/2005 | Simon et al. |
| 6,923,817 B2 | 8/2005 | Carson et al. |
| 6,932,823 B2 | 8/2005 | Grimm et al. |
| 6,947,786 B2 | 9/2005 | Simon et al. |
| 6,960,894 B2 | 11/2005 | Carusillo et al. |
| 6,963,792 B1 | 11/2005 | Green |
| 6,977,356 B2 | 12/2005 | Vaidyanathan et al. |
| 6,978,167 B2 | 12/2005 | Dekel et al. |
| 6,980,229 B1 | 12/2005 | Ebersole |
| 6,990,368 B2 | 1/2006 | Simon et al. |
| 6,993,374 B2 | 1/2006 | Sasso |
| 6,994,004 B2 | 2/2006 | Gass et al. |
| 7,005,606 B2 | 2/2006 | Legge et al. |
| 7,022,123 B2 | 4/2006 | Heldreth |
| 7,027,083 B2 | 4/2006 | Kanade et al. |
| 7,032,458 B2 | 4/2006 | Tanaka |
| 7,034,821 B2 | 4/2006 | Baumberg |
| RE39,102 E | 5/2006 | Schulz et al. |
| 7,084,867 B1 | 8/2006 | Ho et al. |
| 7,102,666 B2 | 9/2006 | Kanade et al. |
| 7,104,996 B2 | 9/2006 | Bonutti |
| 7,106,361 B2 | 9/2006 | Kanade et al. |
| 7,107,091 B2 | 9/2006 | Jutras et al. |
| 7,130,676 B2 | 10/2006 | Barrick |
| 7,139,601 B2 | 11/2006 | Bucholz et al. |
| 7,166,114 B2 | 1/2007 | Moctezuma De La Barrera et al. |
| 7,203,277 B2 | 4/2007 | Birkenbach et al. |
| 7,204,805 B2 | 4/2007 | Dean |
| 7,206,626 B2 | 4/2007 | Quaid et al. |
| 7,206,627 B2 | 4/2007 | Abovitz et al. |
| 7,213,598 B2 | 5/2007 | Zeiss et al. |
| 7,217,276 B2 | 5/2007 | Henderson et al. |
| 7,220,283 B2 | 5/2007 | Terrill |
| 7,226,456 B2 | 6/2007 | O'Neil et al. |
| 7,232,409 B2 | 6/2007 | Hale et al. |
| 7,239,940 B2 | 7/2007 | Wang et al. |
| 7,258,668 B2 | 8/2007 | Hirooka et al. |
| 7,302,288 B1 | 11/2007 | Schellenberg |
| 7,313,430 B2 | 12/2007 | Urquhart et al. |
| 7,317,955 B2 | 1/2008 | McGreevy |
| 7,324,915 B2 | 1/2008 | Altmann et al. |
| 7,361,018 B2 | 4/2008 | Imgrund et al. |
| 7,366,562 B2 | 4/2008 | Dukesherer et al. |
| 7,371,068 B2 | 5/2008 | Lloyd et al. |
| 7,377,429 B2 | 5/2008 | Anderson et al. |
| 7,377,924 B2 | 5/2008 | Raistrick et al. |
| 7,383,073 B1 | 6/2008 | Abovitz et al. |
| 7,399,946 B2 | 7/2008 | Hertzberg et al. |

(56) References Cited

U.S. PATENT DOCUMENTS

| | | |
|---|---|---|
| 7,422,605 B2 | 9/2008 | Burstein et al. |
| 7,463,823 B2 | 12/2008 | Birkenbach et al. |
| 7,485,882 B2 | 2/2009 | Zombo et al. |
| 7,492,930 B2 | 2/2009 | Leitner et al. |
| 7,509,899 B2 | 3/2009 | Gass et al. |
| 7,556,652 B2 | 7/2009 | Angibaud et al. |
| 7,558,617 B2 | 7/2009 | Vilsmeier |
| 7,559,940 B2 | 7/2009 | McGuire et al. |
| 7,561,733 B2 | 7/2009 | Vilsmeier et al. |
| 7,567,834 B2 | 7/2009 | Clayton et al. |
| 7,570,986 B2 | 8/2009 | Huang et al. |
| 7,574,250 B2 | 8/2009 | Niemeyer |
| 7,594,933 B2 | 9/2009 | Kammerzell et al. |
| 7,599,730 B2 | 10/2009 | Hunter et al. |
| 7,636,595 B2 | 12/2009 | Marquart et al. |
| 7,638,958 B2 | 12/2009 | Philipp et al. |
| 7,641,660 B2 | 1/2010 | Lakin et al. |
| 7,643,862 B2 | 1/2010 | Schoenefeld |
| 7,657,300 B2 | 2/2010 | Hunter et al. |
| 7,665,647 B2 | 2/2010 | Shelton, IV et al. |
| 7,697,972 B2 | 4/2010 | Verard et al. |
| 7,697,973 B2 | 4/2010 | Strommer et al. |
| 7,706,683 B2 | 4/2010 | Rossner et al. |
| 7,708,782 B2 | 5/2010 | Burstein et al. |
| 7,715,602 B2 | 5/2010 | Richard |
| 7,726,564 B2 | 6/2010 | Goldbach |
| 7,728,868 B2 | 6/2010 | Razzaque et al. |
| 7,747,311 B2 | 6/2010 | Quaid et al. |
| 7,747,312 B2 | 6/2010 | Barrick et al. |
| 7,758,495 B2 | 7/2010 | Pease et al. |
| 7,760,909 B2 | 7/2010 | Manus |
| 7,766,971 B2 | 8/2010 | Gladdish et al. |
| 7,771,444 B2 | 8/2010 | Patel et al. |
| 7,774,044 B2 | 8/2010 | Sauer et al. |
| 7,794,396 B2 | 9/2010 | Gattani et al. |
| 7,796,789 B2 | 9/2010 | Salgo et al. |
| 7,835,778 B2 | 11/2010 | Foley et al. |
| 7,835,785 B2 | 11/2010 | Scully et al. |
| 7,837,621 B2 | 11/2010 | Krause et al. |
| 7,853,058 B2 | 12/2010 | Gauldie et al. |
| 7,857,756 B2 | 12/2010 | Warren et al. |
| 7,876,942 B2 | 1/2011 | Gilboa |
| 7,885,705 B2 | 2/2011 | Murphy |
| 7,894,872 B2 | 2/2011 | Sherman |
| 7,909,831 B2 | 3/2011 | Axelson, Jr. et al. |
| 7,933,341 B2 | 4/2011 | Agazzi et al. |
| 7,933,782 B2 | 4/2011 | Reiner |
| 7,935,134 B2 | 5/2011 | Reglos et al. |
| 7,937,277 B2 | 5/2011 | Marx |
| 7,949,544 B2 | 5/2011 | Miglietta et al. |
| 7,962,348 B2 | 6/2011 | Dew et al. |
| 7,983,733 B2 | 7/2011 | Viswanathan |
| 7,987,001 B2 | 7/2011 | Teichman et al. |
| 7,993,353 B2 | 8/2011 | Rossner et al. |
| 8,007,437 B2 | 8/2011 | Lombaert et al. |
| 8,010,180 B2 | 8/2011 | Quaid et al. |
| 8,010,181 B2 | 8/2011 | Smith et al. |
| 8,025,680 B2 | 9/2011 | Hayes et al. |
| 8,031,190 B2 | 10/2011 | Smith et al. |
| 8,041,459 B2 | 10/2011 | Sutherland et al. |
| 8,046,050 B2 | 10/2011 | Govari et al. |
| 8,050,938 B1 | 11/2011 | Green et al. |
| 8,057,482 B2 | 11/2011 | Stone et al. |
| 8,074,662 B2 | 12/2011 | Hunter et al. |
| 8,095,237 B2 | 1/2012 | Habibi et al. |
| 8,096,996 B2 | 1/2012 | Gutierrez et al. |
| 8,108,025 B2 | 1/2012 | Csavoy et al. |
| 8,114,086 B2 | 2/2012 | Claypool et al. |
| 8,114,092 B2 | 2/2012 | Altarac et al. |
| 8,116,847 B2 | 2/2012 | Gattani et al. |
| 8,117,549 B2 | 2/2012 | Reiner |
| 8,123,675 B2 | 2/2012 | Funda et al. |
| 8,126,226 B2 | 2/2012 | Bernard et al. |
| 8,131,343 B2 | 3/2012 | Burgkart |
| 8,147,503 B2 | 4/2012 | Zhao et al. |
| 8,157,826 B2 | 4/2012 | Deng et al. |
| 8,160,325 B2 | 4/2012 | Zug et al. |
| 8,160,677 B2 | 4/2012 | Gielen et al. |
| 8,165,658 B2 | 4/2012 | Waynik et al. |
| 8,180,429 B2 | 5/2012 | Sasso |
| 8,193,931 B2 | 6/2012 | Rapaport et al. |
| 8,206,293 B2 | 6/2012 | Reglos et al. |
| 8,207,863 B2 | 6/2012 | Neubauer et al. |
| 8,224,024 B2 | 7/2012 | Foxlin et al. |
| 8,226,690 B2 | 7/2012 | Altarac et al. |
| 8,229,548 B2 | 7/2012 | Frangioni |
| 8,233,963 B2 | 7/2012 | Hartmann et al. |
| 8,238,631 B2 | 8/2012 | Hartmann et al. |
| 8,241,366 B2 | 8/2012 | Roche et al. |
| 8,248,413 B2 | 8/2012 | Gattani et al. |
| 8,248,414 B2 | 8/2012 | Gattani et al. |
| 8,265,790 B2 | 9/2012 | Amiot et al. |
| 8,267,969 B2 | 9/2012 | Altarac et al. |
| 8,282,487 B2 | 10/2012 | Wilson et al. |
| 8,285,363 B2 | 10/2012 | Malackowski et al. |
| 8,287,600 B2 | 10/2012 | Angibaud |
| 8,290,570 B2 | 10/2012 | Hoppe et al. |
| 8,311,611 B2 | 11/2012 | Csavoy et al. |
| 8,315,689 B2 | 11/2012 | Jenkins et al. |
| 8,317,869 B2 | 11/2012 | Cloutier et al. |
| 8,320,612 B2 | 11/2012 | Knobel et al. |
| 8,320,996 B2 | 11/2012 | Panasyuk et al. |
| 8,323,320 B2 | 12/2012 | Lowry et al. |
| 8,337,563 B2 | 12/2012 | Roche et al. |
| 8,494,608 B2 | 7/2013 | Markowitz et al. |
| 8,532,734 B2 | 9/2013 | Markowitz et al. |
| 8,560,047 B2 | 10/2013 | Haider et al. |
| 8,771,304 B1 | 7/2014 | Jurbala |
| 2001/0034530 A1 | 10/2001 | Malackowski et al. |
| 2001/0053907 A1 | 12/2001 | Ota |
| 2002/0016624 A1 | 2/2002 | Patterson et al. |
| 2002/0019644 A1 | 2/2002 | Hastings et al. |
| 2002/0040220 A1 | 4/2002 | Zvuloni et al. |
| 2002/0082865 A1 | 6/2002 | Bianco et al. |
| 2002/0122038 A1 | 9/2002 | Cowperthwaite |
| 2002/0156365 A1 | 10/2002 | Tsekos |
| 2002/0170399 A1 | 11/2002 | Gass et al. |
| 2003/0004519 A1 | 1/2003 | Torode et al. |
| 2003/0069591 A1 | 4/2003 | Carson et al. |
| 2003/0076413 A1 | 4/2003 | Kanade et al. |
| 2003/0078485 A1 | 4/2003 | Hartlep |
| 2003/0153978 A1 | 8/2003 | Whiteside |
| 2003/0209096 A1 | 11/2003 | Pandey et al. |
| 2003/0210812 A1 | 11/2003 | Khamene et al. |
| 2003/0218720 A1 | 11/2003 | Morita et al. |
| 2003/0229279 A1 | 12/2003 | Amstutz et al. |
| 2004/0015070 A1 | 1/2004 | Liang et al. |
| 2004/0043368 A1 | 3/2004 | Hsieh et al. |
| 2004/0068173 A1 | 4/2004 | Viswanathan |
| 2004/0068187 A1 | 4/2004 | Krause et al. |
| 2004/0091462 A1 | 5/2004 | Lin et al. |
| 2004/0092933 A1 | 5/2004 | Shaolian et al. |
| 2004/0106916 A1 | 6/2004 | Quaid et al. |
| 2004/0138556 A1 | 7/2004 | Cosman |
| 2004/0171924 A1 | 9/2004 | Mire et al. |
| 2004/0201857 A1 | 10/2004 | Foxlin |
| 2005/0015005 A1 | 1/2005 | Kockro |
| 2005/0020909 A1 | 1/2005 | Moctezuma de la Barrera et al. |
| 2005/0065617 A1 | 3/2005 | Moctezuma de la Barrera et al. |
| 2005/0107920 A1 | 5/2005 | Ban et al. |
| 2005/0108052 A1 | 5/2005 | Omaboe |
| 2005/0116673 A1 | 6/2005 | Carl et al. |
| 2005/0119550 A1 | 6/2005 | Serra et al. |
| 2005/0131426 A1 | 6/2005 | Moctezuma de la Barrera et al. |
| 2005/0154296 A1 | 7/2005 | Lechner et al. |
| 2005/0156876 A1 | 7/2005 | Kong |
| 2005/0159759 A1 | 7/2005 | Harbaugh et al. |
| 2005/0192583 A1 | 9/2005 | Walker et al. |
| 2005/0197569 A1 | 9/2005 | McCombs |
| 2005/0215879 A1 | 9/2005 | Chuanggui |
| 2005/0216032 A1 | 9/2005 | Hayden |
| 2005/0228250 A1 | 10/2005 | Bitter et al. |
| 2005/0228266 A1 | 10/2005 | McCombs |
| 2005/0251030 A1 | 11/2005 | Azar et al. |

(56) References Cited

U.S. PATENT DOCUMENTS

| | | |
|---|---|---|
| 2005/0251065 A1 | 11/2005 | Henning et al. |
| 2005/0279368 A1 | 12/2005 | McCombs |
| 2005/0288575 A1 | 12/2005 | Moctezuma De La Barrera et al. |
| 2006/0011001 A1 | 1/2006 | Showalter |
| 2006/0063998 A1 | 3/2006 | von Jako et al. |
| 2006/0142656 A1 | 6/2006 | Malackowski et al. |
| 2006/0142739 A1 | 6/2006 | DiSilestro et al. |
| 2006/0176242 A1 | 8/2006 | Jaramaz et al. |
| 2006/0200025 A1 | 9/2006 | Elliott et al. |
| 2006/0224151 A1 | 10/2006 | Waaler |
| 2006/0235849 A1 | 10/2006 | Schmidt et al. |
| 2006/0241388 A1 | 10/2006 | Lavallee |
| 2006/0258938 A1 | 11/2006 | Hoffman et al. |
| 2006/0293557 A1 | 12/2006 | Chuanggui et al. |
| 2007/0018975 A1 | 1/2007 | Chuanggui et al. |
| 2007/0033073 A1 | 2/2007 | Tajaliawal et al. |
| 2007/0043375 A1 | 2/2007 | Anissian |
| 2007/0046661 A1 | 3/2007 | Ma et al. |
| 2007/0055131 A1 | 3/2007 | Deinzer et al. |
| 2007/0055142 A1 | 3/2007 | Webler |
| 2007/0066917 A1 | 3/2007 | Hodorek et al. |
| 2007/0118140 A1 | 5/2007 | Baur et al. |
| 2007/0142917 A1 | 6/2007 | Roche et al. |
| 2007/0161907 A1 | 7/2007 | Goldman et al. |
| 2007/0192133 A1 | 8/2007 | Morgan |
| 2007/0213692 A1 | 9/2007 | Neubauer et al. |
| 2007/0219559 A1 | 9/2007 | Heavener et al. |
| 2007/0219561 A1 | 9/2007 | Lavallee et al. |
| 2007/0225595 A1 | 9/2007 | Malackowski et al. |
| 2007/0236514 A1 | 10/2007 | Agusanto et al. |
| 2007/0238981 A1 | 10/2007 | Zhu et al. |
| 2007/0239159 A1 | 10/2007 | Altarac et al. |
| 2007/0244563 A1 | 10/2007 | Roche et al. |
| 2007/0270660 A1 | 11/2007 | Caylor et al. |
| 2007/0274577 A1 | 11/2007 | De Font Reaulx Rojas |
| 2007/0299334 A1 | 12/2007 | Vilsmeier |
| 2008/0004516 A1 | 1/2008 | DiSilvestro et al. |
| 2008/0004533 A1 | 1/2008 | Jansen et al. |
| 2008/0008366 A1 | 1/2008 | Desh et al. |
| 2008/0010706 A1 | 1/2008 | Moses et al. |
| 2008/0013809 A1 | 1/2008 | Zhu et al. |
| 2008/0051908 A1 | 2/2008 | Angibaud et al. |
| 2008/0077158 A1 | 3/2008 | Haider et al. |
| 2008/0077200 A1 | 3/2008 | Bendett et al. |
| 2008/0103509 A1 | 5/2008 | Goldbach |
| 2008/0109012 A1 | 5/2008 | Falco et al. |
| 2008/0123910 A1 | 5/2008 | Zhu |
| 2008/0125630 A1 | 5/2008 | Caylor |
| 2008/0132882 A1 | 6/2008 | DeMaria et al. |
| 2008/0132909 A1 | 6/2008 | Jascob et al. |
| 2008/0147075 A1 | 6/2008 | Bonutti |
| 2008/0147529 A1 | 6/2008 | Kreiner et al. |
| 2008/0161682 A1 | 7/2008 | Kendrick et al. |
| 2008/0183068 A1 | 7/2008 | Carls et al. |
| 2008/0183074 A1 | 7/2008 | Carls et al. |
| 2008/0183188 A1 | 7/2008 | Carls et al. |
| 2008/0183190 A1 | 7/2008 | Adcox et al. |
| 2008/0183215 A1 | 7/2008 | Altarac et al. |
| 2008/0195109 A1 | 8/2008 | Hunter et al. |
| 2008/0200794 A1 | 8/2008 | Teichman et al. |
| 2008/0200926 A1 | 8/2008 | Verard et al. |
| 2008/0228195 A1 | 9/2008 | von Jako et al. |
| 2008/0235052 A1 | 9/2008 | Node-Langlois et al. |
| 2008/0243125 A1 | 10/2008 | Guzman et al. |
| 2008/0252726 A1 | 10/2008 | Chan et al. |
| 2008/0269596 A1 | 10/2008 | Revie et al. |
| 2008/0269755 A1 | 10/2008 | Malackowski et al. |
| 2008/0281989 A1 | 11/2008 | Hager et al. |
| 2008/0291219 A1 | 11/2008 | Morita et al. |
| 2008/0302226 A1 | 12/2008 | Fischer |
| 2008/0319313 A1 | 12/2008 | Boivin et al. |
| 2009/0017430 A1 | 1/2009 | Muller-Daniels et al. |
| 2009/0018465 A1 | 1/2009 | Hessel et al. |
| 2009/0024140 A1 | 1/2009 | Allen et al. |
| 2009/0036902 A1 | 2/2009 | DiMaio et al. |
| 2009/0051763 A1 | 2/2009 | Adler et al. |
| 2009/0118742 A1 | 5/2009 | Hartmann et al. |
| 2009/0124891 A1 | 5/2009 | Shechter et al. |
| 2009/0125047 A1 | 5/2009 | Reglos et al. |
| 2009/0143828 A1 | 6/2009 | Stad et al. |
| 2009/0183740 A1 | 7/2009 | Sheffer et al. |
| 2009/0187393 A1 | 7/2009 | Van Lierde et al. |
| 2009/0204222 A1 | 8/2009 | Burstein et al. |
| 2009/0216113 A1 | 8/2009 | Meier et al. |
| 2009/0228045 A1 | 9/2009 | Hayes et al. |
| 2009/0234360 A1 | 9/2009 | Alexander |
| 2009/0264940 A1 | 10/2009 | Beale et al. |
| 2009/0281419 A1 | 11/2009 | Troesken et al. |
| 2009/0285465 A1 | 11/2009 | Haimerl et al. |
| 2009/0299439 A1 | 12/2009 | Mire et al. |
| 2009/0309874 A1 | 12/2009 | Salganicoff et al. |
| 2009/0322867 A1 | 12/2009 | Carney et al. |
| 2009/0326322 A1 | 12/2009 | Diolaiti |
| 2009/0326556 A1 | 12/2009 | Diolaiti et al. |
| 2010/0022871 A1 | 1/2010 | De Beni et al. |
| 2010/0030063 A1 | 2/2010 | Lee et al. |
| 2010/0036384 A1 | 2/2010 | Gorek et al. |
| 2010/0036393 A1 | 2/2010 | Unsworth |
| 2010/0036423 A1 | 2/2010 | Hayes et al. |
| 2010/0069758 A1 | 3/2010 | Barnes et al. |
| 2010/0094656 A1 | 4/2010 | Conant |
| 2010/0100081 A1 | 4/2010 | Tuma et al. |
| 2010/0114597 A1 | 5/2010 | Shreiber et al. |
| 2010/0130853 A1 | 5/2010 | Chandonnet et al. |
| 2010/0141961 A1 | 6/2010 | Knobel et al. |
| 2010/0156906 A1 | 6/2010 | Montgomery et al. |
| 2010/0174410 A1 | 7/2010 | Greer et al. |
| 2010/0174558 A1 | 7/2010 | Smith et al. |
| 2010/0179418 A1 | 7/2010 | Mueller et al. |
| 2010/0211179 A1 | 8/2010 | Angibaud et al. |
| 2010/0228117 A1 | 9/2010 | Hartmann |
| 2010/0231509 A1 | 9/2010 | Boillot et al. |
| 2010/0234857 A1 | 9/2010 | Itkowitz et al. |
| 2010/0241129 A1 | 9/2010 | Markey et al. |
| 2010/0245549 A1 | 9/2010 | Allen et al. |
| 2010/0249571 A1 | 9/2010 | Jensen et al. |
| 2010/0256504 A1 | 10/2010 | Moreau-Gaudry et al. |
| 2010/0262150 A1 | 10/2010 | Lian |
| 2010/0280363 A1 | 11/2010 | Skarda et al. |
| 2010/0292703 A1 | 11/2010 | Couture |
| 2011/0007069 A1 | 1/2011 | Lee |
| 2011/0009694 A1* | 1/2011 | Schultz ............ A61B 1/00052 600/109 |
| 2011/0015647 A1 | 1/2011 | Salisbury et al. |
| 2011/0026794 A1 | 2/2011 | Sundar et al. |
| 2011/0060341 A1 | 3/2011 | Angibaud et al. |
| 2011/0064286 A1 | 3/2011 | Chien et al. |
| 2011/0066143 A1 | 3/2011 | Bischoff et al. |
| 2011/0119089 A1 | 5/2011 | Carlisle |
| 2011/0125149 A1 | 5/2011 | El-Galley et al. |
| 2011/0130761 A1 | 6/2011 | Plaskos et al. |
| 2011/0137156 A1 | 6/2011 | Razzaque et al. |
| 2011/0144658 A1 | 6/2011 | Wenderow et al. |
| 2011/0160569 A1 | 6/2011 | Cohen et al. |
| 2011/0160593 A1 | 6/2011 | Deno et al. |
| 2011/0161110 A1 | 6/2011 | Mault |
| 2011/0166883 A1 | 7/2011 | Palmer et al. |
| 2011/0190637 A1 | 8/2011 | Knobel et al. |
| 2011/0224688 A1 | 9/2011 | Larkin et al. |
| 2011/0230894 A1 | 9/2011 | Simaan et al. |
| 2011/0242097 A1 | 10/2011 | Miyamoto |
| 2011/0257653 A1 | 10/2011 | Hughes et al. |
| 2011/0264107 A1 | 10/2011 | Nikou et al. |
| 2011/0270084 A1 | 11/2011 | Choi et al. |
| 2011/0301654 A1 | 12/2011 | Wozencroft et al. |
| 2011/0301732 A1 | 12/2011 | Gao |
| 2012/0015329 A1 | 1/2012 | Gross et al. |
| 2012/0016269 A1 | 1/2012 | Moctezuma de la Barrera |
| 2012/0019511 A1 | 1/2012 | Chandrasekhar |
| 2012/0035417 A1 | 2/2012 | Möllstam et al. |
| 2012/0040305 A1 | 2/2012 | Karazivan et al. |
| 2012/0046521 A1 | 2/2012 | Hunter et al. |
| 2012/0046536 A1 | 2/2012 | Cheung et al. |
| 2012/0046668 A1 | 2/2012 | Gantes |

(56) References Cited

U.S. PATENT DOCUMENTS

| | | | |
|---|---|---|---|
| 2012/0046914 A1 | 2/2012 | Gao | |
| 2012/0078236 A1 | 3/2012 | Schoepp | |
| 2012/0087558 A1 | 4/2012 | Meyer | |
| 2012/0088965 A1* | 4/2012 | Stokes | A61B 1/00087 600/104 |
| 2012/0100517 A1 | 4/2012 | Bowditch et al. | |
| 2012/0101847 A1 | 4/2012 | Johnson et al. | |
| 2012/0108900 A1 | 5/2012 | Viola et al. | |
| 2012/0113223 A1 | 5/2012 | Hilliges et al. | |
| 2012/0120091 A1 | 5/2012 | Koudijs et al. | |
| 2012/0123418 A1 | 5/2012 | Giurgi et al. | |
| 2012/0143213 A1 | 6/2012 | Myrman | |
| 2012/0157841 A1 | 6/2012 | Glaenzer et al. | |
| 2012/0165652 A1 | 6/2012 | Dempsey | |
| 2012/0209392 A1 | 8/2012 | Angibaud et al. | |
| 2012/0215094 A1 | 8/2012 | Rahimian et al. | |
| 2012/0220859 A1 | 8/2012 | Amiot et al. | |
| 2012/0222323 A1 | 9/2012 | Tait | |
| 2012/0223970 A1 | 9/2012 | Cortés Provencio | |
| 2012/0226150 A1 | 9/2012 | Balicki et al. | |
| 2012/0232377 A1 | 9/2012 | Nottmeier | |
| 2012/0259204 A1 | 10/2012 | Carrat et al. | |
| 2012/0274631 A1 | 11/2012 | Friedland et al. | |
| 2012/0289825 A1 | 11/2012 | Rai et al. | |
| 2013/0010081 A1 | 1/2013 | Tenney et al. | |
| 2013/0030250 A1 | 1/2013 | Findeisen et al. | |
| 2013/0039732 A1 | 2/2013 | Brewer et al. | |
| 2013/0041292 A1 | 2/2013 | Cunningham | |
| 2013/0116574 A1 | 5/2013 | Knobel et al. | |
| 2014/0030669 A1 | 1/2014 | Hey et al. | |
| 2016/0022374 A1 | 1/2016 | Haider et al. | |
| 2016/0206376 A1 | 7/2016 | Haider et al. | |
| 2017/0007327 A1 | 1/2017 | Haider et al. | |
| 2017/0281280 A1 | 10/2017 | Haider et al. | |

FOREIGN PATENT DOCUMENTS

| | | | |
|---|---|---|---|
| CN | 1806771 A | 7/2006 | |
| CN | 101011280 A | 8/2007 | |
| CN | 101797182 A | 8/2010 | |
| CN | 102905641 A | 1/2013 | |
| DE | 10008806 | 12/2001 | |
| DE | 20321068 U1 | 1/2006 | |
| DE | 202005015438 | 3/2006 | |
| EP | 0674881 B1 | 5/2000 | |
| EP | 1219259 B1 | 7/2003 | |
| EP | 1374793 A1 | 1/2004 | |
| EP | 1504726 A1 | 2/2005 | |
| EP | 1442729 B1 | 3/2006 | |
| EP | 1994882 A1 | 11/2008 | |
| EP | 2138280 B1 | 3/2011 | |
| EP | 1404212 B1 | 4/2011 | |
| EP | 1153292 B1 | 8/2011 | |
| EP | 1523951 B1 | 10/2012 | |
| EP | 2508118 A1 | 10/2012 | |
| GB | 1003153 A | 9/1965 | |
| GB | 1499812 A | 2/1978 | |
| GB | 2298931 A | 9/1996 | |
| GB | 2417222 B | 9/2008 | |
| JP | 2000510362 A | 8/2000 | |
| JP | 2002514448 A | 5/2002 | |
| JP | 2006102100 A | 4/2006 | |
| WO | WO89/01192 A1 | 2/1989 | |
| WO | WO89/07910 A1 | 9/1989 | |
| WO | WO94/24933 A1 | 11/1994 | |
| WO | WO95/01757 A1 | 1/1995 | |
| WO | WO96/11624 A2 | 4/1996 | |
| WO | WO99/49280 A1 | 9/1999 | |
| WO | WO00/21442 A1 | 4/2000 | |
| WO | WO00/63719 A1 | 10/2000 | |
| WO | WO01/01845 A2 | 1/2001 | |
| WO | WO01/37743 A1 | 5/2001 | |
| WO | WO02/060653 A2 | 8/2002 | |
| WO | WO2004/001569 A2 | 12/2003 | |
| WO | WO2004/069036 A2 | 8/2004 | |
| WO | WO2005/000139 A1 | 1/2005 | |
| WO | WO2005/072629 A1 | 8/2005 | |
| WO | WO2005/074303 A1 | 8/2005 | |
| WO | WO2005/076033 A1 | 8/2005 | |
| WO | WO2007/073551 A1 | 6/2007 | |
| WO | WO2007/085909 A2 | 8/2007 | |
| WO | WO2007/113815 A2 | 10/2007 | |
| WO | WO2008/064126 A2 | 5/2008 | |
| WO | WO2008/076079 A1 | 6/2008 | |
| WO | WO2009/047629 A1 | 4/2009 | |
| WO | WO2009/111682 A1 | 9/2009 | |
| WO | WO2010/067267 A1 | 6/2010 | |
| WO | WO2010/123858 A2 | 10/2010 | |
| WO | WO2011/020505 A1 | 2/2011 | |
| WO | WO2011/028575 A2 | 3/2011 | |
| WO | WO2011/063266 A2 | 5/2011 | |
| WO | WO2011/116347 * | 9/2011 | A61B 6/00 600/424 |
| WO | WO2011/133927 A2 | 10/2011 | |
| WO | WO2011/133946 A2 | 10/2011 | |
| WO | WO2011/134083 A1 | 11/2011 | |
| WO | WO2012/013304 A1 | 2/2012 | |
| WO | WO2012/045626 A1 | 4/2012 | |
| WO | WO2012/078989 A1 | 6/2012 | |
| WO | WO2012/171555 A1 | 12/2012 | |
| WO | WO2013/080124 A1 | 6/2013 | |

OTHER PUBLICATIONS

DiGioia; Computer-Assisted Measurement Tools for Surgeons and Researchers, Presented at the 47th Annual Meeting of the Orthopaedics Research Society (ORS), San Francisco, CA, Feb. 25-28, 2001 (copy unavailable from publisher).

DiGioia et al.; Computer Assisted Orthopaedic Surgery Image Guided and Robotic Assistive Technologies; Clinical Orthopaedics and Related Research; No. 354; pp. 8-16; Sep. 1998.

DiGioia et al.; HipNav: Pre-operative planning and intra-operative navigational guidance for acetabular implant placement in total hip replacement surgery; Porc. of the Computer Assisted Orthopaedic Surgery Simposium; Bern, Switzerland; 8 pgs.; Nov. 1995.

Feaver et al.; U.S. Pat. No. 8,431,085 entitled "Energy-emitting attachments and methods for medical instruments," filed Apr. 28, 1995.

Gibson (Frisken) et al.; Simulating surgery using volumetric object representations, real-time volume rendering and haptic feedback; TR97-02; 21 pgs.; Dec. 1997.

Gibson (Frisken) et al.; Surgical Simulation: A knee arthroscopy system (presentation); SIGGRAPH'99 Course; 43 pgs.; Aug. 1999.

Kazanzides et al.; Force sensing and control for a surgical robot; Proc. of the 1992 IEEE Int. Conf. on Robotics and Automation; Nice, France; pp. 612-617; May 1992.

O'Toole, III et al.; Towards more capable and less invasive robotic surgery in orthopaedics; CVRMed'95; Nice, France; pp. 123-130; Apr. 3-6, 1995.

Paul et al.; A surgical robot for total hip replacement surgery; Proc. of the 1992 IEEE Conf. on Robotics and Automation; Nice, France; pp. 606-611; May 1992.

Simon et al.; Accuracy validation in image-guided orthopaedic surgery; Proc. of the 2nd International Symp. on Medical Robotics & Computer Assisted Surgery; pp. 185-192; 1995 (year of pub. sufficiently earlier than effective US filed and any foreign priority date).

Troccaz et al.; Computer-augmented surgery; Human Movement Science; 15(3); pp. 445-475; Jun. 1996.

Tsai et al.; An orthopedic virtual reality surgical simulator; JCat 2000; 10th Int. Conf. on Artificial Reality and Tele-existence; Nat. Taiwan Univ.; taipei, Taiwan; 8 pgs.; Oct. 25-27, 2000.

Yao et al.; Primary musculoskeletal neoplasms: Effectiveness of core-needle biopsy; radiology; 212; pp. 682-686; Sep. 1999.

Agus et al.; A multiprocessor decoupled system for the simulation of temporal bone surgery; Computing and Visualization in Science, vol. 5, Issue 1, pp. 35-43; Jul. 2002 (author manuscript, 10 pgs.).

(56) References Cited

OTHER PUBLICATIONS

Amstutz et al.; Press-fit prosthesis: Principle, Results, and Techniques (Chap. 20); pp. 261-270. In: Amstutz, H.C. (Ed.): Hip Arthroplasty. 1st ed.; Elsevier Health Sciences, Aug. 1991.

Azuma et al.; Recent Advances in Augmented Reality; IEEE Computer Graphics and Applications; 21(6); pp. 34-47; Nov./Dec. 2001.

B Braun / Aesculap AG; OrthoPilot®, Orthopaedic Navigation System; 1 pg.; printed from: http://www.orthopilot.com/cps/rde/xchg/ae-orthopilot-en-int/hs.xsl/7218.html on Oct. 24, 2013 (This web address was available to applicant(s) at least as of Jun. 2008).

Bach et al.: Scoring systems in total knee arthroplasty, Clin Orthop Relat Res.; 399; pp. 184-196; Jun. 2002.

Barrera et al., "Comparison of Distal Femoral TKR Bone Cuts by Freehand Navigation vs. Conventional Cutting Jigs", The Fourth Annual Conference of the International Society for Computer Assisted Orthopaedic Surgery, CAOS-International, Chicago, IL, Jun. 2004.

Barrera et al., "Freehand Navigation Cutting for Distal Femoral TKR bone for MIS", Annual Symposium of International Society for Technology in Arthroplasty (ISTA), Rome, Italy, Sep. 2004.

Barrera et al., "Intra Operative Graphical Interface for Freehand Navigated Bone Cutting for TKR Without Jigs-Assessment of First Cuts", Poster 246, 5th Combined Meeting of the Orthopaedic Research Societies of Canada, U.S.A., Japan and Europe, Banff, Alberta, Canada, Oct. 2004.

Barrera et al., "Simulation and Navigation for Knee Replacement Surgery", Paper presented at the 16th Annual Nebraska Biomedical Research Workshop, Omaha, NE, Apr. 2003.

Barrera et al.; Towards a standard in assessment of bone cutting for TKR; (presentation poster); 18th Ann. Symposium of the International Society for Technology and Arthroplasty (ISTA); Kyoto, Japan; Sep. 29-Oct. 2, 2005.

Barrera et al.; Towards a standard in assessment of bone cutting for total knee replacement; Proc Inst Mech Eng H; 222(2); pp. 63-74; Jan. 2008.

Bellamy et al.: Validation study of WOMAC: a health status instrument for measuring clinically important patient relevant outcomes to antirheumatic drug therapy in patients with osteoarthritis of the hip or knee. J Rheumatol; 15 (12); pp. 1833-1840; Dec. 1988.

Blue Belt Technologies, Inc.; NavioPFS} (brochure); 4 pgs.; © 2013; downloaded from: http://www.bluebelttech.com; this web address available to applicant(s) at least as of Nov. 2012.

Bobyn et al.: Osteogenic phenomena across endosteal bone-implant spaces with porous surfaced intramedullary implants. Acta Orthop Scand; 52(2): pp. 145-153, 1981 (year of pub. sufficiently earlier than effective US filing date and any foreign priority date).

Brainlab; Image-Guided Surgery Platforms; 2 pages; printed on Oct. 24, 2013 from http://www.brainlab.com/product/item/image-guided-surgery-platforms (This web address was available to applicant(s) at least as of Jun. 2008).

Brisson et al., "Precision Freehand Sculpting of Bone", 3rd Annual Meeting of the International Society for Computer Assisted Orthopaedic Surgery, CAOS International, Marbella, Spain, pp. 105-112; Jun. 2003.

Carlsson et al.; Implant fixation improved by close fit. Cylindrical implant-bone interface studied in rabbits. Acta Orthop Scand; 59 (3): 272-5, Jun. 1988.

Collier et al.; Macroscopic and microscopic evidence of prosthetic fixation with porous-coated materials; Clin Orthop Relat Res; 235; pp. 173-180; Oct. 1988.

Cooke et al.; Universal bone cutting device for precision knee replacement arthroplasty and osteotomy. J Biomed Eng 7(1): pp. 45-50, Jan. 1985.

Davies et al.; ACROBOT—using robots and surgeons synergistically in knee surgery; Advanced Robotics; ICAR '97; 8th International Conference; Monterey, CA; Proceedings; pp. 173-178; Jul. 7-9, 1997.

Davies: Rating systems for total knee replacement. Knee; 9(4); pp. 261-266; Dec. 2002.

Dawson et al.; Questionnaire on the perceptions of patients about total knee replacement. J Bone Joint Surg (Br) 80(B): 63-9, Jan. 1998.

Denis et al.: Influence of bone milling parameters on the temperature rise, milling forces and surface flatness in view of robot-assisted total knee arthroplasty. International Congress Series, vol. 1230, pp. 300-306; Jun. 2001.

Dunbar et al.: Translation and validation of the Oxford-12 Item Knee Score for use in Sweden. Acta Orthopaedica Scandinavica; 71(3); pp. 268-274; Jun. 2000.

Edwards et al.; Design and evaluation of a system microscope-assisted guided interventions (MAGI); MICCAI'99; LNCS 1679; pp. 842-852; Proc. 2nd Int. Conf.; Cambridge, UK; Sep. 19-22, 1999.

Fleute et al.; Incorporating a statistically based shape model into a system for computer-assisted anterior cruciate ligament surgery; Medical Image Analysis; 3(3); pp. 209-222; Sep. 1999.

Forman et al., "Computer-Assisted Freehand Navigation for Knee Replacement Surgery," The Fourth Annual Conference of the International Society for Computer Assisted Orthopaedic Surgery, CAOS-International, Chicago, IL, pp. 192-193; Jun. 2004.

Gavaghan et al.; A portable image overlay projection device for computer-aided open liver surgery; IEEE Transactions on Biomedical Engineering; 58(6); pp. 1855-1864; Jun. 2011.

Giraud et al.: Bone cutting. Clin. Phys. Physiol. Meas.; 12(1): pp. 1-19, Feb. 1991.

Grood et al.: A joint coordinate system for the clinical description of threedimensional motions: application to the knee. J. Biomech. Eng.; 105: pp. 136-144, May 1983.

Haider et al., "Computer Simulation of Bone Cutting for Knee Replacement Surgery With Freehand Navigation", SE042, 71st Annual Meeting, American Academy of Orthopaedic Surgeons (AAOS), San Francisco, CA, Mar. 2004.

Haider et al., "Freehand Navigated Bone Cutting for TKR Without Jigs-Assessment of First Cuts", Poster 246, 5th Combined Meeting of the Orthopaedic Research Societies of Canada, U.S.A., Japan and Europe, Banff, Alberta, Canada, Oct. 2004.

Haider et al., "Freehand Navigation Cutting for TKR Surgery Without Jigs: Simulation of Bone Saw Cutting" (abstract), 4th Annual Conference of the International Society for Computer Assisted Orthopaedic Surgery, CAOS-International, Chicago, IL, Jun. 2004.

Haider et al., "Real-Time Simulation of Bone Cutting Minimally Invasive Knee Replacement Surgery", Podium paper No. 1618, International Society for Technology in Arthroplasty (ISTA), San Francisco, CA, Sep. 2003.

Haider et al., Total Knee Replacement Bone Cutting Without Jigs: Is it Time? (podium paper 64, submission 3097); 72nd Annual Meeting of the American Academy of Orthopaedic Surgeons AAOS, Washington, D.C., Feb. 2005.

Haider et al.; A framework and parameters for quantitative assessment of bone cutting for TKR; 5th Annual Meeting fo the International Society for Computer Assisted Orthopaedic Surgery (CAOS); Helsinki, Finland; Jun. 19-22, 2005.

Haider et al.; Quantifying the quality of bone cutting for TKR—a proposed assessment method; (presentation paper); MIS meets CAOS Symposium Series: Less and Minimally Invasive Surgery for Joint Arthroplasty: Facts and Fiction; San Diego, CA, USA; Oct. 20-22, 2005; 5 pgs.

Hall et al.; 2000 National Hospital Discharge Survey; Centers for Disease Control and Prevention (CDC), Advance Data No. 329; 19 pgs., Jun. 19, 2002.

Heilbrun et al.; Stereotactic localization and guidance using a machine vision technique; Stereotact Funct Neurosurg.; 58(1-4); pp. 94-98; 1992; Proc. of American Society for Stereotactic & Functional Neurosurgery; Pittsburgh, PA; Jun. 16-19, 1991.

Imperial College London; Robot Assisted Surgery More Accurate Than Conventional Surgery (press release); 2 pgs.; printed Oct. 24, 2013 from http://www.imperial.ac.uk/college.asp?P=7449; Feb. 2006.

Insall et al.; Rationale of the Knee Society Clinical Rating System, Clin Orthop Relat Res., 248: pp. 13-14, Nov. 1989.

(56) References Cited

OTHER PUBLICATIONS

Jakopec et al.; Acrobot: a hands-on robot for total knee replacement surgery; Advanced Motion Control; 7th Intl. Workshop; Piscataway, NJ; pp. 116-120; Jul. 3-5, 2002.
Jakopec et al.; The first clinical application of a "hands-on" robotic knee surgery system; Computer Aided Surgery; 6(6); pp. 329-339; 2001 (year of pub. sufficiently earlier than effective US filing date and any foreign priority date).
Jaramaz et al.; Range of motion after total hip arthroplasty: Experimental verification of the analytical simulator; CVRMed-MRCAS'97; LNCS; vol. 1205; pp. 573-582; Genoble, FR; Mar. 19-22, 1997.
Kim et al.: An Er: YAG Laser Bone Cutting Manipulator for Precise Rotational Acetabular Osteotomy. Proc. of the 26th Annual International Conference of the IEEE EMBS San Francisco, CA, USA. pp. 2750-2753; Sep. 1-4, 2004.
Kim et al.; Results of the Harris-Galante cementless hip prosthesis; J Bone Joint Surg Br; 74(1); pp. 83-87; Jan. 1992.
Knutson et al; Knee revision for aseptic loosening; Surgical Techniques in Orthopaedics and Traumatology; 55-560-C-10; 5 pgs.; 2001 (year of pub. sufficiently earlier than effective US filing date and any foreign priority date).
Leitner et al.; Computer-assisted knee surgical total replacement; CVRMed-MRCAS'97; Lecture Notes in Computer Science; vol. 1205; pp. 629-637; Genoble, FR; Mar. 19-22, 1997.
Levinson et al.; Surgical navigation for THR: A report on clinical trial utilizing HipNav; MICCAI 2000; 3rd Int. Conf.; LNCS; vol. 1935; pp. 1185-1187; Pittsburg, PA; Oct. 11-14, 2000.
Liow et al.: Functional rating for knee arthroplasty: comparison of three scoring systems, Orthopedics, 26(2): pp. 143-149, Feb. 2003.
Liow RY, Walker K, Wajid MA, Bedi G, Lennox CME: The reliability of the American Knee Society Score, Acta Orthopaedica Scandinavica, 71(6): pp. 603-608, Dec. 2000.
Lisien et al.: Mini Bone-Attached Robotic System. Sensor Based Planning Lab, Carnegie Mellon University. Printed Oct. 24, 2013 from http://web.archive.org/web/20041207011420/http://voronoi.sbp.ri.cmu.edu/mbars/; © 2001; Last modified Jun. 1, 2004.
Insall: Results of Total Knee Arthroplasty. Chap. 34, pp. 975-982. In Insall JN, Windsor RE, Scott WN, Kelly MA, Aglietti P (Eds.), Surgery of the Knee, vol. 2, 2nd ed, Churchill Livingstone Inc., New York, May 1993.
Lotke et al.; Influence of Positioning of Prosthesis in Total Knee Replacement; J Bone Joint Surg Am; 59(1); pp. 77-79; Jan. 1977.
MacDonald: Improved tibial cutting accuracy in knee arthroplasty, Medical Engineering & Physics; 26: pp. 807-812, Nov. 2004.
Michigan Metrology, LLC: Glossary of Surface Texture Parameters, printed Dec. 16, 2013 from internet archive, 9 pgs. (http://web.archive.org/web/20040524202705/http://www.michmet.com/).
Noble et al.; The anatomic basis of femoral component design; Clin Orthop Relat Res; 235; pp. 148-165; Oct. 1988.
Piek et al.: Waterjet dissection in neurosurgical procedures: clinical results in 35 patients. J Neurosurg; 96: pp. 690-696, Apr. 2002.
Piltner et al., "Computational Modelling of Novel Implants for Minimally Invasive Knee Replacement Surgery", Poster presented at the 16th Annual Nebraska Biomedical Research Workshop, Omaha, NE, Apr. 2003.
Reaungamornrat et al.; Tracker-on-C: A novel tracker configuration for image-guided therapy using a mobile C-arm; Int J CARS; 6(suppl 1); pp. S134-S137; Jun. 2011.
Richter et al, "Integration of Computer-Based Systems in Foot and Ankle Surgery", Navigation and MIS in Orthopedic Surgery, Ch. 63, pp. 486-495; Dec. 2006.
Rosenberg et al.; Cementless Total Knee Arthroplasty; Chap. 30, pp. 869-890. In Insall et al. (Eds.), Surgery of the Knee, vol. 2, 2nd ed, Churchill Livingstone Inc., New York, Jul. 1993.
Rupprecht et al.; Er: YAG laser osteotomy directed by sensor controlled systems. J Craniomaxillofac Surg, 31(6): pp. 337-42, Dec. 2003.
Sandborn et al.: The effect of surgical fit on bone growth into porous coated implants. 33rd Annual Meeting, Orthopaedic Research Society; San Francisco, CA; pp. 217; Jan. 1987.
Sauer et al.; An augmented reality navigation system with a single-camera tracker: System design and needle biopsy phantom trial; Med. Imaging Computing and Computer-Assisted Intervention—MICCAI 2002; 2489; 5th Int. Conf.; Tokyo, Japan; Proc. Part II; pp. 116-124; Sep. 25-28, 2002.
Schnaider et al.; Implementation and evaluation of an augmented reality system supporting minimal invasive interventions; Virtual and Augmented Reality Status Conference 2004; 10 pgs.; Leipzig; Feb. 19-20, 2004.
Simon et al.; Development and validation of a navigational guidance system for acetabular implant placement; CVRMed-MRCAS'97; Lecture Notes in Computer Science; 1205; pp. 583-592; 1997 (year of pub. sufficiently earlier than effective US filing date and any foreign priority date).
Staub et al.; Visual instrument guidance in minimally invasive robot surgery; International Journal on Advances in Life Sciences; 2(3/4); pp. 103-114; 2010 (year of pub. sufficiently earlier than effective US filing date and any foreign priority date).
Tardif et al.; Projector-based augmented reality in surgery without calibration; Engineering in Medicine and Bilogy Society, 2003; Proc of the 25th ann. int. conf. of the IEEE; vol. 1; Sep. 17-21, 2003.
Taylor et al.; An image-directed robotic system for precise orthopaedic surgery; IEEE Trans. On Robotics and Automation; 10(3); pp. 261-275; Jun. 1994.
Toksvig-Larsen et al.; Surface characteristics following tibial preparation during total knee arthroplasty, The Journal of Arthroplasty, 9(1): pp. 63-66, Feb. 1994.
Toksvig-Larsen et al.; Surface flatness after bone cutting. A cadaver study of tibial condyles, Acta Orthopaedica Scandinavica 62(1): pp. 15-18, Feb. 1991.
Wapler et al.; Controlling miniature robotic systems in minimally invasive surgery; Intelligent Robots and Systems '94. 'Advanced Robotic Systems and the Real World', IROS '94. Proc. of the IEEE/RSJ/GI Int'l Conf. (vol. 1); Munich, DE; pp. 711-716; Sep. 12-16, 1994.
Wu et al.; The dimensional accuracy of preparation of femoral cavity in cementless total hip arthroplasty; J Zhejiang Univ Sci; 5(10); pp. 1270-1278, Oct. 2004.
Haider et al.; U.S. Appl. No. 13/842,526 entitled "On-board tool tracking system and methods of computer assisted surgery," filed Mar. 15, 2013.
Haider et al.; U.S. Appl. No. 14/052,569 entitled "Method and Apparatus for Computer Aided Surgery," filed Oct. 11, 2013.
Haider et al.; U.S. Appl. No. 15/675,345 entitled "Method and apparatus for computer aided surgery," filed Aug. 11, 2017.

* cited by examiner

SURGICAL TOOL

OTT ON SURGICAL TOOL

LID REMOVED

| d | 105 | mm | | |
|---|---|---|---|---|
| a | 94 | deg | | |
| t | MOD/d | MOL/d | MOD | MOL |
| 1 | 13.32 | 28.6 | 1398 | 3001 |
| 2 | 6.65 | 14.3 | 698 | 1502 |
| 3 | 4.42 | 9.5 | 464 | 1002 |
| 4 | 3.31 | 7.2 | 347 | 753 |
| 5 | 2.63 | 5.7 | 277 | 603 |
| 6 | 2.18 | 4.8 | 229 | 504 |
| 7 | 1.86 | 4.1 | 195 | 433 |
| 8 | 1.62 | 3.6 | 170 | 380 |
| 9 | 1.43 | 3.2 | 150 | 339 |
| 10 | 1.27 | 2.9 | 134 | 306 |
| 11 | 1.14 | 2.7 | 120 | 280 |
| 12 | 1.04 | 2.5 | 109 | 258 |
| 13 | 0.95 | 2.3 | 99 | 239 |
| 14 | 0.87 | 2.1 | 91 | 223 |
| 15 | 0.80 | 2.0 | 84 | 209 |
| 16 | 0.73 | 1.9 | 77 | 198 |
| 17 | 0.68 | 1.8 | 71 | 187 |
| 18 | 0.63 | 1.7 | 66 | 178 |
| 19 | 0.58 | 1.6 | 61 | 170 |
| 20 | 0.54 | 1.6 | 57 | 163 |
| 21 | 0.50 | 1.5 | 53 | 157 |
| 22 | 0.47 | 1.4 | 49 | 151 |
| 23 | 0.43 | 1.4 | 46 | 146 |
| 24 | 0.40 | 1.3 | 42 | 141 |

MOD - Minimum Object Distance

MOL - Maximum Object Length (at MOD)

MOD/d = 1/ (tan(a/2+t) - tan(a/2-t))

MOL/d = 1 + 2 (MOD/d)* tan (a/2-t)

FIG. 11B

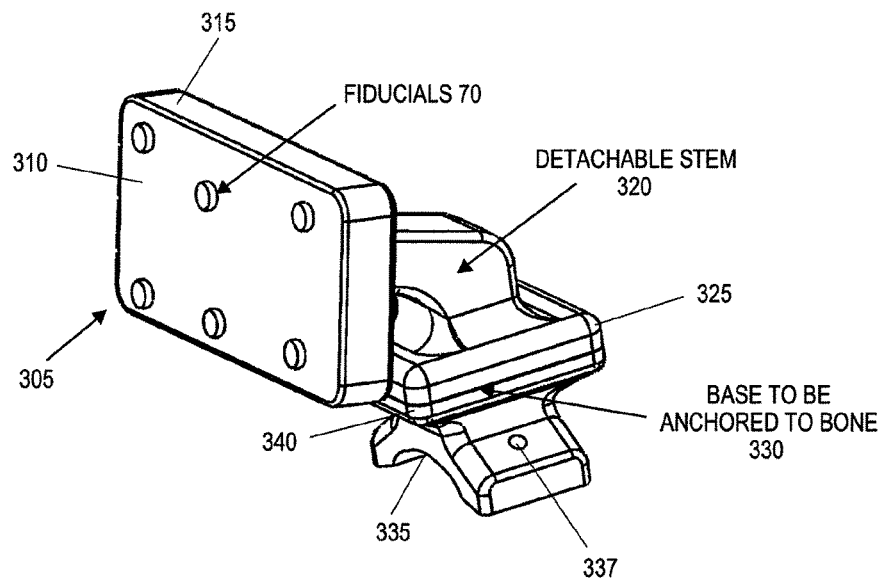
FIG. 16A
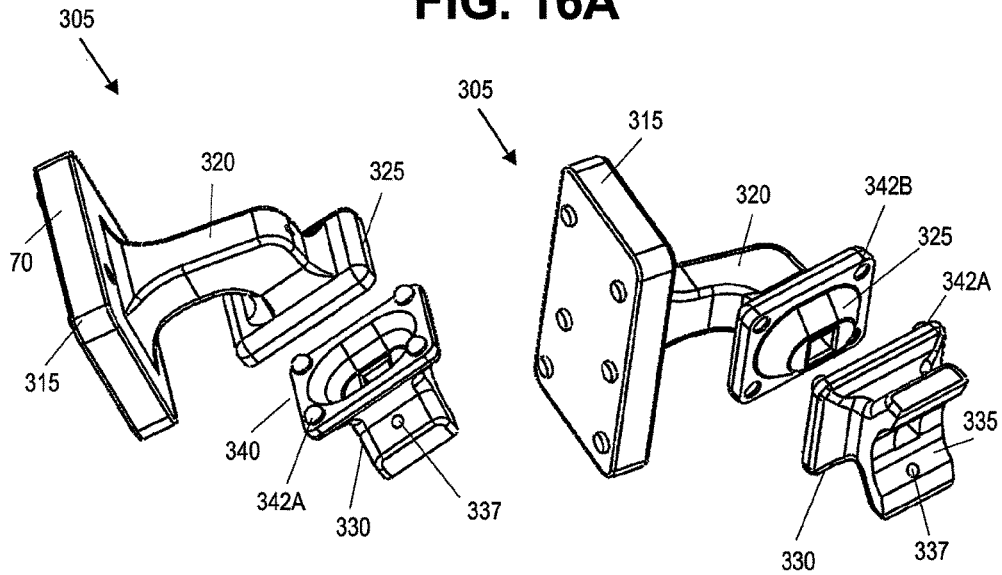
FIG. 16B  FIG. 16C

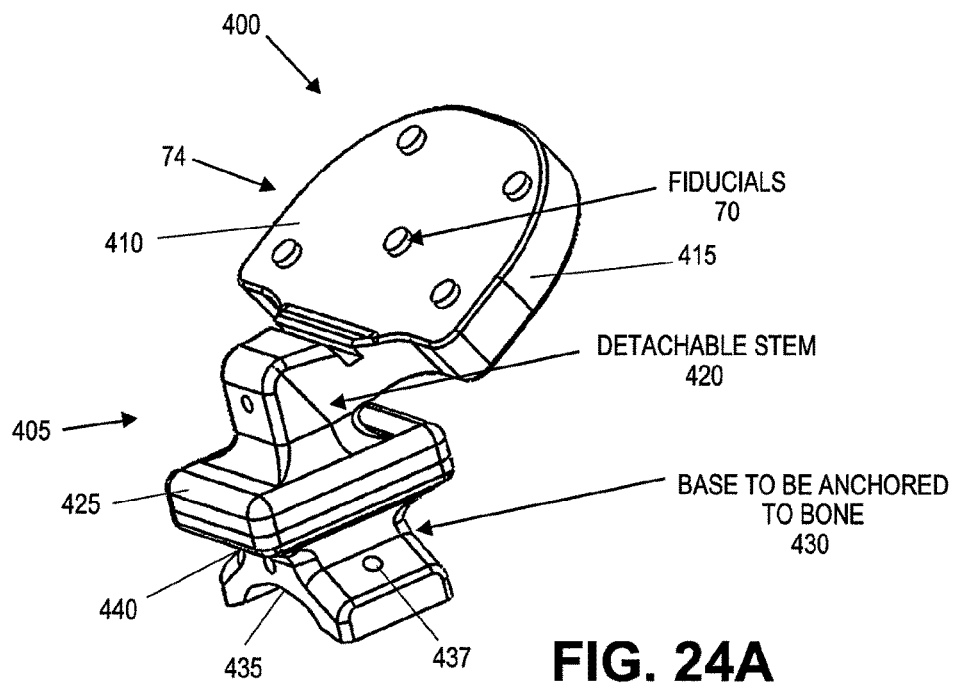
FIG. 24A
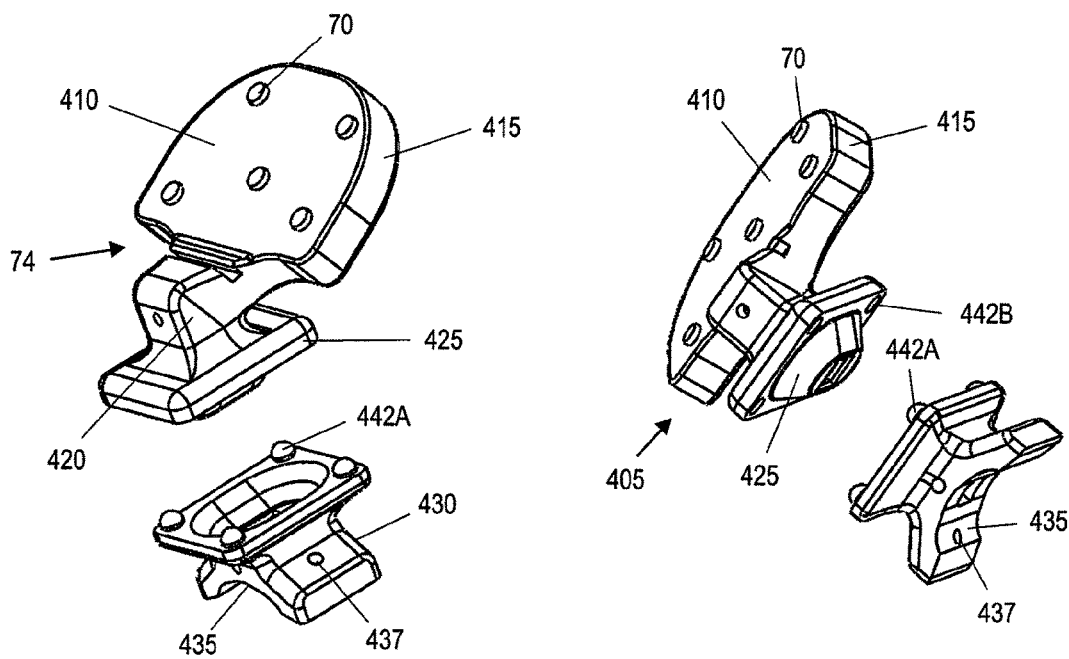
FIG. 24B  FIG. 24C

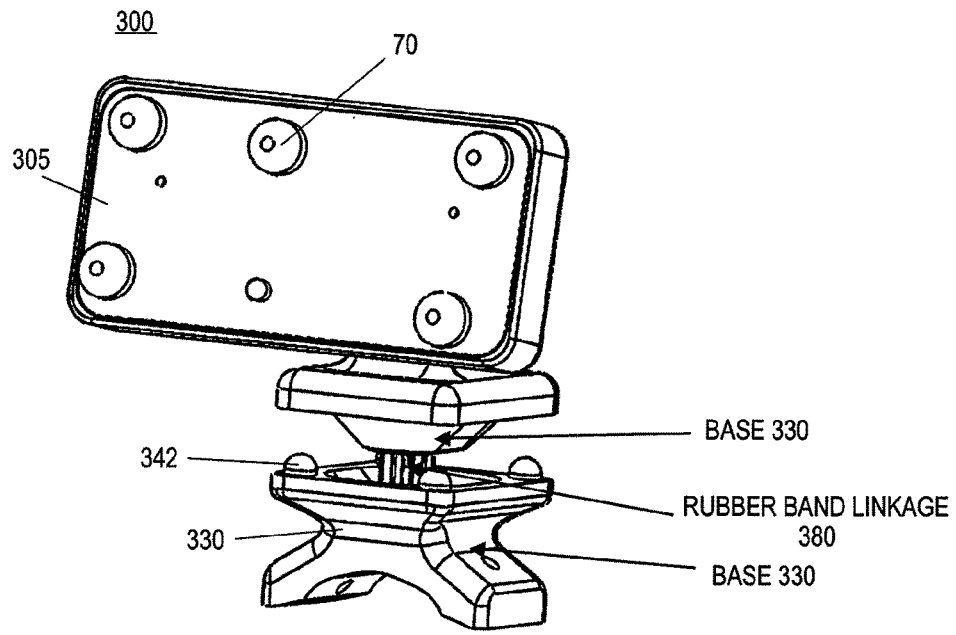
FIG. 26A
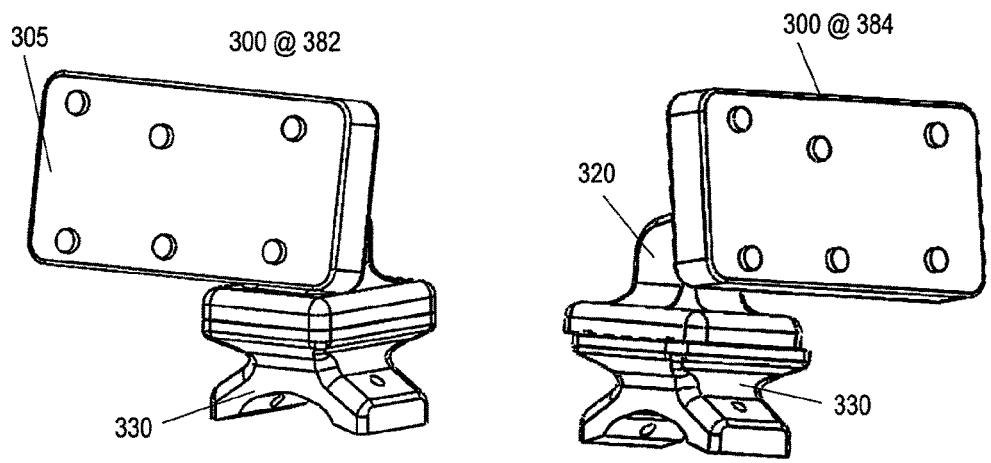
FIG. 26B  FIG. 26C

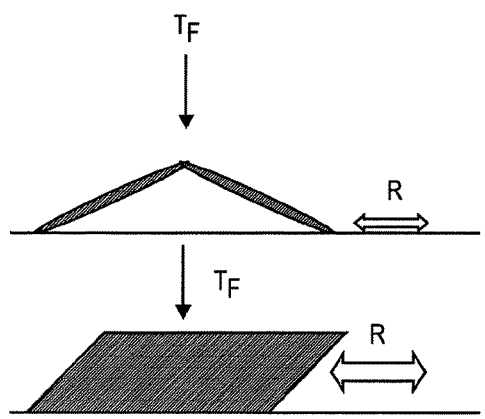
FIG. 37A
FIG. 37B
FIG. 37C
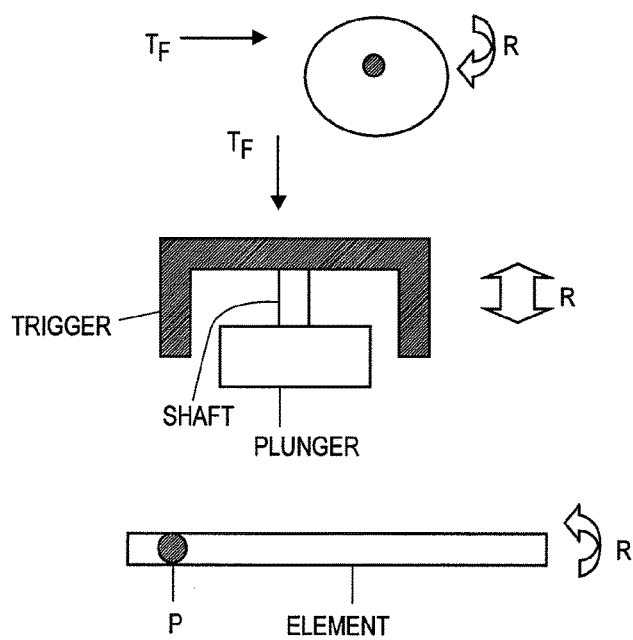
FIG. 37D
FIG. 37E

LOW PROFILE AT FULL SPEED POSITION

FIG. 39A
PUSH-PULL THROUGH A SOLID ACTUATOR
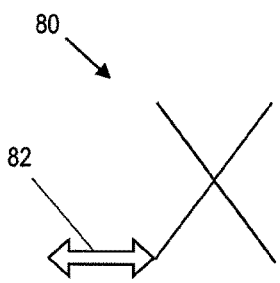
FIG. 39B
PULL / SPRING RETURN - BOWDEN CABLE
"NORMALLY OFF"
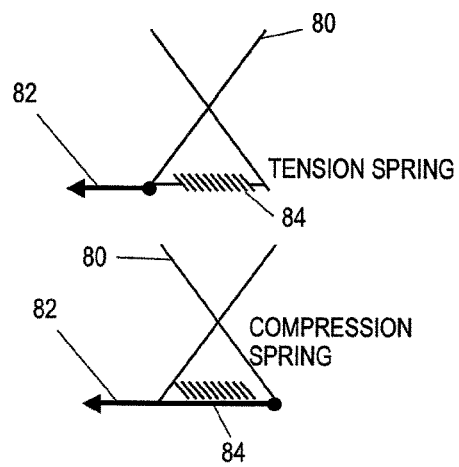
FIG. 39C
THE MOVEMENT OF THE ACTUATOR SHOWN DETERMINES THE HEIGHT OF THE UPPER END OF THE SCISSOR ARMS THEREFORE THE ELEVATION OF THE SCISSOR MECHANISM. THIS HEIGHT WILL PRESS AGAINST, AND WILL BE FELT BY THE USER PLACING HIS OR HER FINGER ON THE TOOL TRIGGER.

All forces can be determined at all positions

MECHANISM ON TOOL - REPLACES THE TOOL TRIGGER

ON-BOARD TOOL TRACKING SYSTEM AND METHODS OF COMPUTER ASSISTED SURGERY

CROSS REFERENCE TO RELATED APPLICATIONS

This application is a National Stage Entry of PCT Application No. PCT/US2012/044486, filed Jun. 27, 2012 which claims the benefit under 35 U.S.C. § 119 of U.S. Provisional Patent Application No. 61/501,489, filed Jun. 27, 2011, titled "SYSTEM FOR COMPUTER ASSISTED NAVIGATION AND CONTROL OF A POWER TOOL." These applications are herein incorporated by reference in their entireties.

STATEMENT AS TO FEDERALLY SPONSORED RESEARCH

This invention was made with Government support under Grant No. W911QY-10-C-0178, awarded by the Army Natick Soldier System Center. The Government has certain rights in the invention.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates to the field of computer assisted surgery. Specifically, the present invention relates to various aspects of a surgical suite in which a tracking system on a tool provides guidance or assistance during a surgical procedure.

BACKGROUND

Many surgical procedures are complex procedures requiring numerous alignment jigs and intricate soft tissue procedures. Preparing and placing the alignment jigs and other preparation is often a significant part of the procedure. For instance, when performing a total knee replacement procedure ("TKR"), the prosthesis must be accurately implanted to ensure that the joint surfaces are properly aligned. If the alignment is inaccurate, the misalignment can eventually lead to failure of the joint, requiring the complex task of replacing one or more portions of the knee prosthesis.

To ensure that the prosthesis is accurately implanted, during a TKR procedure, the surgeon uses a variety of jigs to guide the cutting of the femur and the tibia. The jigs are complex devices that require significant time and skill to locate and attach on the patient during the surgical procedure.

The advent of computer assisted surgery (CAS) provides the promise of simplifying many of the complexities of surgical procedures. To date systems have been developed that utilize separate room based tracking systems designed to monitor the cutting jigs, tools and the patient. In some instances, the computer may be used to guide the surgeon during the process. The placement of the in room camera closer to the tool has been proposed. However, improvements are needed to address the challenges of the real-time and dynamic environment of a surgical procedure.

Although computer assisted surgery holds promise, there are numerous aspects to be addressed to make a system commercially viable and useful to surgeons. There continues to exist numerous aspects of computer assisted surgery that require improvement to improve the efficiency and/or quality of the procedure for processing of CAS data, and more useful outputs to the user.

SUMMARY OF THE DISCLOSURE

In one aspect, a tactile feedback mechanism includes a first platform; a second platform; a scissor linkage formed by a first linkage coupled to a second linkage, the scissor linkage extending between the first platform and the second platform wherein a first end of the first linkage is coupled to the first platform and a second end of the first linkage is coupled to the second platform and the first end of the second linkage is coupled to the first platform and the second end of the second linkage is coupled to the second platform; and at least one position restoration element coupled to the scissor linkage to adjust a force response of the relative movement between the first platform and the second platform. In some aspects the at least one position restoration element is coupled between the first end of the first linkage and the second end of the second linkage. In another aspect, the at least one position restoration element extends along a second platform and is coupled to the scissor linkage to adjust the movement of the second linkage second end relative to the second platform. In one embodiment, the first platform and the second platform are configured for operation alongside, partially covering, partially surrounding, partially over or completely over a trigger of a surgical tool. In one embodiment, a trigger cover is placed within the first platform for engagement with the trigger.

In still another configuration of a tactile feedback mechanism, there is provided at least one position restoration element coupled to the scissor linkage to adjust a force response of the relative movement between the first platform and the second platform is coupled so as to extend between the first platform and the second platform. Still further, there may be provided a position restoration element coupled to the scissor linkage and extending along the second platform. In one specific configuration of a tactile feedback mechanism, the position restoration element is a return spring coupled to second end of the second linkage there is an override spring coupled to the return spring and also may an actuator coupled to the override spring. In another embodiment of a tactile feedback mechanism, the position restoration element is a spring coupled in tension to the movement of the second ends of the scissor linkage relative to the second platform. In still another position restoration element configuration, a spring coupled in compression to the movement of the second ends of the scissor linkage relative to the second platform. In some feedback mechanisms, there is also a shaft extending from an opening in the second platform and coupled to the scissor linkage wherein movement of the scissor linkage produces corresponding movement of the shaft relative to the opening. The alternatives to the shaft include for example, a flexible shaft portion, a cable portion, a hollow shaft portion or a flexible linkage portion.

In still other configurations, an embodiment of a tactile feedback mechanism may be used in conjunction with an embodiment of an on tool tracking device configured for use in computer assisted surgery. Such an OTT device would include for example a component or series of components the working cooperation within the on tool tracking device that are adapted and configured to translate the shaft relative movement into a signal used in a computer assisted surgery procedure. In one aspect the component may be an actuator, a solenoid, a motor, a potentiometer, a linear potentiometer, or a linear encoder or other device positioned adjacent the cable to register and measure displacement of cable. In one aspect, cable movement relates to a signal indicative of the operation of the trigger of the surgical tool. In still further embodiments, the same component or a different component may also act as an actuator to impart movement to the shaft to influence the relative movement between the first platform and the second platform. These various components and functions are each used in support of being configured to impart movement to or respond to the shaft in response to a signal related to controlling the operation of the surgical tool during a computer assisted surgery procedure.

In another embodiment, there is provided a reference frame for use in a computer assisted surgery procedure. The reference frame includes a frame having a surface bounded by perimeter; the stem extending from the frame; a coupling on the stem; a base having a first surface configured to engage a portion of the anatomy within a surgical field related to the procedure and a second surface to engage with the coupling. In some configurations, there may also be provided at least one registration element on the coupling and at least one registration element on the second surface wherein the registration elements are adapted and configured for mating cooperation when the coupling is engaged to the second surface. In still further configurations, a plurality of registration elements on the coupling; and a plurality of registration elements on the second surface, wherein a portion of the registration elements on the coupling when engaged with a portion of the registration elements on the second surface will orient the frame in a first orientation within the surgical field. In one aspect, movement between the coupling in the second surface to engage other of said plurality of registration elements will position the frame in a second, different orientation within the surgical field. In some aspects, the first and second orientations are known position and are used in surgical preplanning. The reference frame may include other features such as surface for engagement anatomy, and aperture for a fixation element or configurations to mate with particular anatomical targets. In another aspect, there is provided a reference frame according to claim C1, further comprising: a reference frame guide having a frame and a stem extending from the frame, wherein the stem has a curvature or shape configured to engage with an anatomical feature to assist in the placement of the reference frame. In one aspect, the reference frame guide further comprising: one or more engagement elements along the frame for temporary engagement with the perimeter or a portion of the reference frame to permit proper positioning and adjustment of a base associated with the reference frame. In one aspect, the portion of the bony anatomy relates to the placement of the stem in relation to the condyles. In another aspect, the reference frame includes a mount coupling adapted and configured to maintain the relative position and orientation of the coupling and the second surface. In one aspect, the mount coupling is provided in the reference frame such that when the mount coupling is mated to the base the mount coupling is within an interior portion of the reference frame. In another aspect, the mount coupling is provided in the reference frame such that when the mount coupling attached to the reference frame the mount coupling substantially or completely surrounds the area of mating contact between the coupling and the second surface.

In one alternative embodiment, there is provided a method of performing a computer aided surgery procedure within a surgical field. First, step of attaching a first reference frame within the surgical field at a first position; then, attaching a second reference frame within the surgical field at a second position; and thereafter initiating an active step of the procedure using the surgical tool while maintaining positioning information used during the computer aided surgery procedure obtained from both the first and the second reference frames. In one alternative aspect, there is the step of adjusting the position of a surgical tool relative to a section of the anatomy during a step or as part of the procedure while maintaining positioning information used during the computer aided surgery procedure obtained from the first and/or the second reference frames attached to the section of the anatomy. In one alternative embodiment there is also the step of hovering the surgical tool during a step of as part of the procedure while maintaining positioning information used during the computer aided surgery procedure obtained from either the first and/or the second reference frames. In still further aspect, there are methods including one or more of the steps of initiating, adjusting or hovering is performed in furtherance of one or more steps of a computer assisted surgery procedure on a knee. In still further alternative, there are methods including, one or more steps of a computer assisted surgery procedure on a knee comprising: making a distal lateral condoyle cut, making a distal medial condoyle cut, making an anterior cut, making a posterior lateral condoyle cut, making a posterior medial condoyle cut, making an anterior chamfer cut, making a posterior lateral condoyle chamfer cut, making a posterior medial condoyle chamfer cut making a femoral box cut, drilling a hole in a portion of a surgical site and making a tibial cut. In still another alternative embodiment, the method method proceeds while maintaining the first reference frame and the second reference frame in the first position and the second position respectively after completion of the attaching steps, altering the orientation of a portion of the reference frame relative to the surgical field and thereafter using position information from the altered orientation for a portion of a computer aided surgery procedure. In still further aspect, the position information relating to the orientations of the first reference frame and the second reference frame in both the initial and the altered orientation are used as part of the preplanning processes for the computer aided surgery.

In another alternative embodiment, there is an on tool tracking and guidance device. In one aspect, the device has a housing having a surface for releasable engagement with a portion of a surgical tool; a first camera and, optionally, a second camera in an arrangement where each of the first camera and the second camera (if provided) provides an image output selected for viewing substantially all or a portion of a surgical field selected for a computer assisted surgery procedure. The OTT device in one aspect may include a simple output device for communicating information to the user about the ongoing OTT CAS processes. In still other aspects, the OTT device may include a projector configured to provide an output at least partially within the surgical field of view. The various embodiments of OTT device is described herein may incorporate a wide variety of capabilities for electronic image processing and image communication capabilities within the housing. Still further, additional embodiments may be configured to receive an output from each of the one, two, or more cameras provided by an embodiment of an OTT device. Additionally or optionally, electronics and processing capabilities of the OTT device may be utilized to perform a wide range of digital processing functions. In one aspect, electronics included with the OTT perform an image processing operation using at least a portion of the output from two cameras configured for use in the computer assisted surgery procedure. In one aspect camera selected for use with an OTT device include a field of view from about 70 mm to about 200 mm, or optionally, from about 50 mm-250 mm from the first and second cameras. Still other ranges and camera configurations may be used in various other embodiments.

In a still further embodiment, the OTT housing surface for releasable engagement with a portion of a surgical tool is shaped to form a complementary curve with the portion of the surgical tool or a modified surgical tool selected for engagement with the housing and, in some instances, the of the surgical tool is modified to accommodate releasable engagement with the housing surface. In one example, the surface for releasable engagement with a portion of a surgical tool is adapted and configured so that when the surface is coupled to the surgical tool at least a portion of an active segment of the surgical tool lies within the horizontal field of view and the vertical field of view.

In a still further aspects, the projector may include such attributes as: the output from the projector is projected on or near an active element associated with a surgical tool attached to the housing; the output from the projector is adapted for projection on a portion of the patients anatomy, or on or within the surgical field surface in the surgical scene; an adaptation process gives an adapted projector output that is adjusted for the curvature, roughness or condition of the anatomy. In one aspect, the projector is a pico projector.

In on embodiment, there is a method for performing a computer assisted surgery procedure using a hand held surgical instrument having an on tool tracking device attached thereto including collecting and processing computer assisted surgery data using the on tool tracking device; assessing the data in real time during the computer assisted surgery procedure; performing CAS related operations using the on tool tracking device selected from at least two of controlling the operation of the tool, controlling the speed of the tool and providing to the user guidance related to a CAS step; controlling the operation or speed of the tool or providing guidance to the user to adjust the speed of the tool; and providing a user of the surgical instrument an output related to the assessing step. There may also be, in additional or alternative aspects, one or more of displaying, projecting, or indicating an output related to a computer assisted surgery processing step.

There may also be, in additional or alternative aspects, an output comprising one or more of a tactile indication, a haptic indication, an audio indication or a visual indication; the tactile indication comprises a temperature indication; and the haptic indication comprises a force indication or a vibration indication. Still further aspects, the output is the control signal automatically generated to adjust a performance parameter of the surgical tool in response to a result of the assessing step. In other aspects, the performance parameter includes modifying a tool cutting speed or stopping a tool operation the output of providing step further comprising electronics to control operation of power tools (modifying cutting speed and/or stopping it). There may also be, in additional or alternative aspects, a determining step that is based upon an evaluation of one or more of: a physical parameter within the surgical field such as position or combination of positions of elements tracked in the field through reference frames attached to them a reference frame input, take projected image, a motion detected from a sensor, a motion detection from a calculation, the overall progress of a computer aided surgery procedure, a measured or predicted deviation from a previously prepared computer aided surgery plan. Still further, the determining step selects one of a number of predefined processing modes, such as for example hover mode, site approach mode, and active step mode. IN each of these modes there are specific outputs, processing techniques and algorithms applied to the CAS data.

In still further aspects, there are OTT CAS processing mode factors are selected from one or more of a camera frame size; an OTT camera orientation; an adjustment to a camera software program or firmware in accordance with the desired adjustment; adjustments to an OTT camera or other camera image outputs to modify a size of a region of interest within a horizontal field of view, the vertical field of view or both the horizontal and the vertical field of view of the camera; drive signals for adjustable camera lens adjustment or positioning; image frame rate; image output quality; refresh rate; frame grabber rate; reference frame two; reference frame one; on reference frame fiducial select; off reference frame fiducial select; visual spectrum processing; IR spectrum processing; reflective spectrum processing; LED or illumination spectrum processing; surgical tool motor/actuator speed and direction, overall CAS procedure progress; specific CAS step progress; image data array modification; an OTT pico projector refresh rate; an OTT pico projector accuracy; one or more image segmentation techniques; one or more logic-based extractions of an image portion based on a CAS progress; signal-to-noise ratio adjustment; one or more image amplification process, one or more imaging filtering process; applying weighted averages or other factors for dynamic, real-time enhancement or reduction of image rate, pixel or sub-pixel vision processing; a hand tremor compensation; an instrument-based noise compensation for a saw, a drill or other electrical surgical tool and a vibration compensation process based on information from the OTT each alone or in any combination.

In still other aspects, the output is provided to the user with a projector in the on tool tracking device. In addition, the projector output is adjusted based upon a physical characteristic the surgical site presented during the display of the projector output. It is to be appreciated that the physical characteristic is one or more of the shape of the portion of the size available to the projector output; the topography in the projector projected field and the orientation of the projector to the portion of the site available for the projector output. Optionally, the projector or a display on the OTT device has an output that includes information visible to the user of the surgical tool while the surgical tool is in use in the surgical site. In still further aspects, the projector or a display on the OTT device output includes information visible to the user of the surgical tool to indicate the position, relative motion, orientation, or other navigation parameter related to the positioning of the active element of the surgical tool within the surgical field according to the surgical plan. Still the step of providing an output from an OTT device may include displaying the output on a system screen; on a GUI interface on the OTT or a mobile device screen.

In a still further aspect, any of the above steps of outputting a CAS output to the user is, optionally, changed and an OTT CAS processing technique or output is modified as a result of the user performing one or more steps of a computer assisted surgery procedure on a knee comprising: making a distal femur lateral condyle cut, making a distal femur medial condyle cut, making a distal femur anterior cut, making a distal femur posterior lateral condyle cut, making a distal femur posterior medial condyle cut, making a distal femur anterior chamfer cut, making a distal femur posterior lateral condyle chamfer cut, making a distal femur posterior medial condyle chamfer cut, making proximal tibial cut. In still other alternatives, the methods herein of outputting a CAS output to the user is changed as a result of one of the above recited steps performed during a surgical procedure related to one of a shoulder; a hip; an ankle; a vertebra; or an elbow. Additionally, an OTT CAS processing technique or output is modified as a result of one of the above recited steps performed during a surgical procedure related to one of a shoulder; a hip; an ankle; a vertebra; or an elbow.

In still another aspects, there is provided a system for performing computer assisted surgery, having a surgical tool having an active element corresponding to the surgical function of the tool; an on tool tracking device coupled to the tool using a housing configured to engage with at least a portion of the surgical tool; at least one camera in the housing configured to obtain imaging information related to the surgical tool and a surgical field; an output device like the display, or, optionally a projector in the housing configured to provide a projected output on or near an active element of the surgical tool; a computer having computer readable instructions stored within electronic memory for performing a computer assisted surgical procedure using data at least partially obtained from the on tool tracking device and to provide an output for use during a step of the surgery. When the system includes a projector within the OTT capabilities, the projector further comprising one or more of the following: projection capability to project an output on a portion of the patient's anatomy, a surface within the surgical scene, an electronic device, or other object within the projector output range. In one configuration, the computer is in the housing in another the computer is separated from the on tool tracking device and connected via a wired or a wireless connection. In still further aspects, the system includes one or more of the computer readable instructions for performing any of the CAS mode select methods described above. In still further aspect, the system may include the on tool tracking device having one or more of the elements described above. The system may adapted and configured for use with one or more reference frames and associated methods described herein. In a still further aspect, the system is adapted and configured for use in combination with a tactile feedback mechanism described herein.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 11A, 11B, 11C and 11D provide additional information relating to variations of camera angle.

FIGS. 16A, 16B and 16C illustrate various views of a reference frame.

FIGS. 24A, B and C illustrates a reference frame and its components.

FIGS. 26A, 26B, and 26C illustrate another reference frame embodiment having a flexible linkage joining the components of the frame.

FIGS. 37A-44 relate to various alternative tactile feedback mechanisms along with related kinematic responses and design criteria.

FIG. 37A illustrates a bent form that deflects to move an actuator in response to trigger force.

FIG. 37B illustrates a sliding trapezoid form that will deform and restore its shape in response to trigger force.

FIG. 37C illustrates a rotating reader or encoder used to provide a rotating response to the trigger force.

FIG. 37 D illustrates a frame moving in response to trigger force to depress a shaft into a base where the movement of the shaft may be registered as an indication of trigger force.

FIG. 37 E illustrates a pinned element that may deflect to indicate an amount of trigger force.

FIGS. 39A, 39B and 39C each illustrate a scissor mechanism without a position restoration element (39A), with a tension spring as a position restoration element (39B) and a compression spring as a position restoration element (39C).

FIG. 47 illustrates the tactile feedback mechanism in an expanded configured that covers the trigger and FIG. 48 shows the tactile feedback mechanism collapsed to expose the trigger.

DETAILED DESCRIPTION

Figure 1:
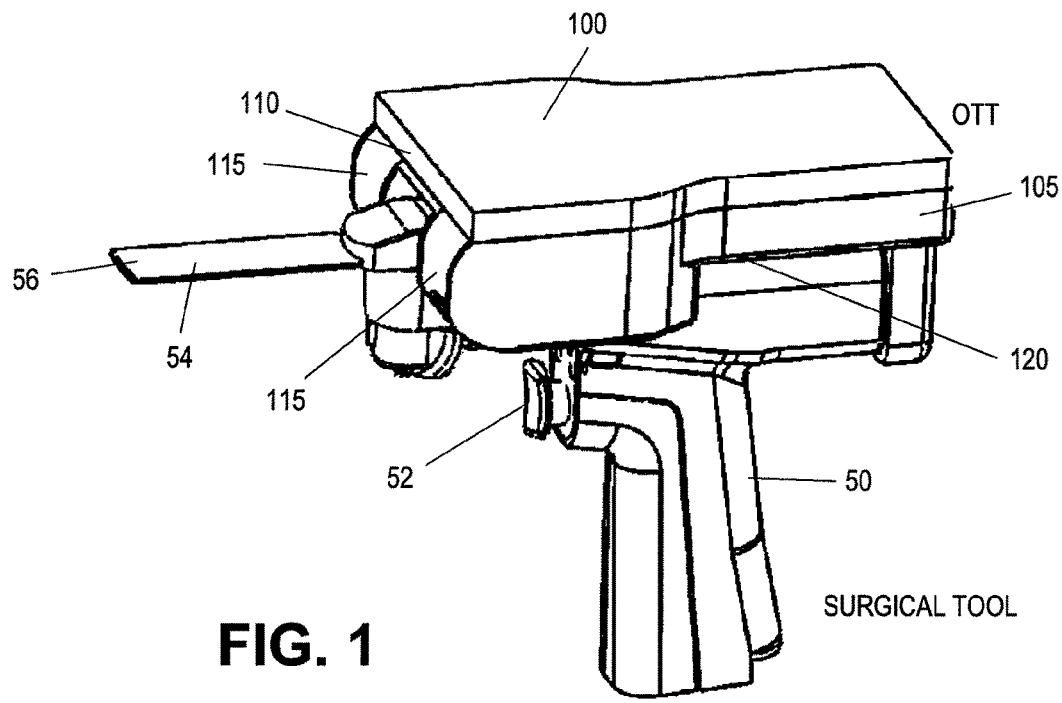
FIG. 1 illustrates an isometric view of an on tool tracking device attached to a surgical instrument.

The present invention is a system for performing computer assisted orthopedic surgery and novel tools for operating that system. The present invention overcomes limitations of current computer assisted surgery systems by optionally combining all elements of computer assisted surgery (tools, displays and tracking) into a single smart instrument. The instrument does not rely on an external navigation system but the tool contains all the tracking equipment on the tool itself in a self-contained assembly. As a result, the overall system is significantly less complicated, less intrusive to the surgeon and easy to integrate into existing practices in orthopedic surgery.

By way of overview, the system is comprised of principal subsystems. The first is the tool itself, which is used to carry a standalone on tool tracking device or modified to contain the subsystems or elements of the subsystems to provide On-Tool Tracking (OTT) functionality. The modifications can be simple, such as an extended chassis to hold the additional components, or complex, such as a modified power system to power the additional subsystems, and/or to stop or control the motor speed or other actuators on the powered tool. The second subsystem is the tracking subsystem, which comprises one or more trackers and one or more tracking elements. The tracker can be a one or more cameras (stereovision) that are sensitive to visible light or light from another wavelength. Alternatively, the tracker could be an electromagnetic tracker or other non-camera based system. The tracking element is whatever the tracker tracks. For example, where the tracker is an infrared camera, the tracking element is an infrared LED, or a passive surface reflective of infra-red light emitted from around the camera or elsewhere. Where the tracker is a pair of high-resolution cameras sensitive to visible light, the tracking element could be the specific anatomy of a patient or marks made directly on the anatomy including markers or reference frames. The subsystem can utilize one or more trackers, mounted on the tool in various configurations, to track one or more tracking elements. In one aspect, the tracker(s) used the sensors required to track the tool, the patient and the other relevant objects in order to perform an OTT CAS surgery, are located, at least in part, on-board the surgical tool in a self-contained manner. The navigation system navigates when the tracking subsystem calculates the position of the tracking element(s) relative to the tool.

The third subsystem is an OTT CAS computer system that contains an appropriate CAS planning software and programming to perform OTT CAS functions surgical plan. The surgical plan can be produced through a variety of means but contains the dimensions of the resections (e.g. cuts, drill holes, volume of tissue to be removed), intended by the operator, in three-dimensional space. The system can also contain a reference image of the patient's anatomy, such as a computed tomography image (dataset) of a patient's anatomy, and 2D or 3D virtual models of the patient's anatomy as a point of reference. The computer system compiles data from the tracking system and the surgical plan to calculate the relative position of boundaries defining the intended resections by the tool. In some configurations, the computer system can be a wholly separate component, in wireless communication with the other components. In other configurations, the computer system is integrated into the other systems. Together, the tracking system and the computer system can determine if the surgeon's location and movement of the tool (the surgical path) will produce the desired resection. It is important to note that the computer sub system and the tracking sub system work together to establish the three dimensional space of the surgical site. Elements necessary for the tracking sub-system to function can be located in the computer sub-system or some intermediary mode of transmitting tracking data to the computer sub-system.

The final subsystem is an indicator to provide the surgeon with OTT CAS appropriate outputs related to when his movement of the tool, as well as in relation is to the intended resection within a real time OTT CAS step. The indicator can be any variety of means to align/locate the surgical path with the intended resection: a panel of lights that sign directions to correct the surgeon, a speaker with audio instructions, a screen, touchscreen or iPhone or iPAd like device (i.e., a so-called "smartphone") on the OTT equipped tool displaying 3d representation of the tool and the patient with added guide imagery or a digital projection (eg. by a picoprojector) onto the patient's anatomy of the appropriate location of a resection. The indicator serves to provide an appropriate OTT CAS output to guide the surgeon to make the right resection based on real time information.

Looking now to the specific subsystems:

A surgical suite for computer assisted surgery includes a first computer for pre-operative use. For example, pre-operative analysis of the patient and selection of various elements may be performed on the first computer. The suite may also include a second computer, referred to as the OR computer, which is used during a procedure to assist the surgeon and/or control one or more surgical instruments. In addition the suite may include a computer (standalone or collaborating with another computer) mounted on the surgical instrument via an embodiment of an on tool tracking system. First computer is provided in the present instance, but may be omitted in some configurations because the functions of the computer are also implemented on the OR computer, which can be a standalone. Moreover the whole 'pre-surgical planning' may eventually happen instantaneously inside the OR using primarily the OR computer in conjunction with an OTT. Nevertheless, if desired for particular applications, the first computer may be used. The pre-surgical planning and procedure can also be aided by data or active guidance from online web-links. As used herein, the term CAS system or CAS computer refers to those computer or electronic components as provided in any of these combinations to perform CAS function. Furthermore, the micro-processing unit of the system can reside in the on tool tracking instrument. In such a configuration, the computations and user interface can be performed within a computer borne on the surgical tool being used, or in collaboration with the main system computer by wired or wireless communication. In collaboration with the main OTT CAS computer by wireless communication, such system performs error analysis of location of the cutting instrument relative to the ideal cut to be performed, and displays corrective actions and other information on a screen provided as part of the on tool tracker alone or in any combination with an output provided by one or more projectors provided with the OTT for that purpose.

As a result, a surgical suite for OTT CAS may include a tracking/navigation system that allows tracking in real time of the position in space of several elements, including: (a) the patient's structures, such as the bone or other tissue; (b) the surgical tool, such as the bone saw and/or OTT, which carries the OTT and is controlled by the surgeon based on information from the OR computer or (c) surgeon/assistants system specific tools, such as a pointer, registration tools, or other objects as desired. The OR computer or an OTT may also perform some control on the instrument. Based on the location of the tool and feedback from an OTT, the system or CAS computer is able to vary the speed of the surgical tool as well as turn the tool off to prevent potential damage. Additionally, the CAS computer may provide variable feedback to a user. The surgical instrument shown in the accompanying description is a surgical saw. It is to be appreciated that many others instruments can be controlled and/or navigated as described herein, such as a drill, burr, file, broach, scalpel, stylus, or other instrument. Therefore in the following discussion, the OTT enabled CAS system is not limited to the particular tool described, but has application to a wide variety of instruments and procedures.

As discussed further below, one exemplary use of the surgical suite incorporates the use of a virtual model of the portion of the patient upon which a procedure is to be performed. Specifically, prior to a procedure, a three dimensional model of the relevant portion of the patient is produced using CT scans, MRI scans or other techniques. Prior to surgery, the surgeon may view and manipulate the patient model to evaluate the strategy for proceeding with the actual procedure.

One potential methodology uses the patient model as a navigation device during a procedure. For instance, prior to a procedure, the surgeon may analyze the virtual model of a portion of the patient and map out the tissue to be resected during a procedure. The model is then used to guide the surgeon during the actual procedure. Specifically, during the procedure, the on tool tracking device monitors the progress of the procedure. As a result of the OTT CAS processes performed, the progress/results are displayed in real time on the OR computer or on an OTT monitor (e.g. onboard LCD screen) so that the surgeon can see the progress relative to the patient model. Importantly, the surgeon is also provided an OTT projector to provide real type feedback based on OTT CAS processing steps (described in greater detail below).

To provide navigation assistance during an OTT CAS procedure, an on tool tracking device monitors the position of the associated surgical tool within the surgical field. The OTT CAS system may use none, or one or more reference frames including one or more positions sensors or one or more fiducial markers depending upon the requirements of the OTT CAS procedure being undertaken. Any of the above described markers may be utilized in an active or passive configuration. Markers may, optionally, be wired or wireless sensors that are in communication with the system. An active marker emits a signal that is received by the OTT device. In some configurations, the passive markers are wireless markers that need not be electrically connected to the OTT CAS system. In general, a passive marker reflects infrared light back to an appropriate sensor on the OTT device. When using passive markers, the surgical field of view is exposed to infrared light that is then reflected back to and received by the OTT from which the data locations of the passive markers is determined by the OTT CAS. Some embodiments of an OTT device may be provided with an infrared transmission device and an infrared receiver. The OTT receives light emitted light from the active markers and reflected light from the passive markers along with other visual field information from the OTT. The OTT CAS system performs calculations and triangulates the three dimensional position of the tool based on the vision processing of the images including the position of the markers along with other imaging information in the surgical field. Embodiments of the on tool tracking device are operable to detect the orientation of the OTT enabled tool relative to three orthogonal axes. In this way, using information from the OTT device, the OTT CAS system determines the location and orientation of the tool, and then uses that information to determine OTT CAS processing modes and produce appropriate OTT CAS outputs for the user.

As is typical in CAS, a series of points or surfaces are used to register or correlate the position of the patient's anatomy with the virtual model of the patient. To gather this information, a navigated pointer is used to acquire points at an anatomical landmark or a set of points on a surface within the patient's anatomy. A process referred to morphing may alternatively be used to register the patient to an approximate virtual model of the patient taken from an atlas or database and not originating from actual imaging of that particular patient. During such a process, the surgeon digitizes parts of the patient and some strategic anatomical landmarks. The OTT CAS computer analyzes the data and identifies common anatomical features to thereby identify the location of points on the patient that correspond to particular points on the virtual model.

Accordingly, as set forth above, the on tool tracking device visually monitors the position of several items in real time, including: the position of the associated surgical tool, the position of the patient and the position of items used during a procedure, such as one or more reference frames or one or more markers. Accordingly, the OTT CAS computer processes the OTT CAS data regarding the position of the associated surgical tool, visual field information in OTT image data, the data regarding the position of the patient, and the data regarding the model of the patient. This result of OTT CAS computer processes provide dynamic, real time interactive position and orientation feedback information, which can be viewed by the surgeon on a monitor provided by the OTT device (if provided) or as a displayed output of an OTT projector. Further still, as previously described, prior to a procedure, the surgeon may analyze the patient model and identify the tissue that is to be resected as well as plan for or indicate desired OTT CAS mode for use during an OTT CAS step or during an CAS procedure. This information can then be used during the procedure to guide the surgeon using dynamically adjusted outputs based on the mode of CAS processing and other factors.

FIG. 1 is an isometric view of an on tool tracking device (OTT) 100 arranged for tracking and providing guidance during computer aided surgery using the surgical instrument 50. The OTT 100 has a housing 105 that includes a pair of cameras 115, in an opening for projector output 110. The OTT 100 and also as a housing 105 with a surface 120 adapted and configured to mate with the surgical instrument 50. The surgical instrument 50 includes a trigger 52 for operating a tool 54 having an active element 56. An illustrative embodiment of FIG. 1 the tool 54 is a saw and the active element 56 is the serrated edge of the distal end thereof.

Figure 2:
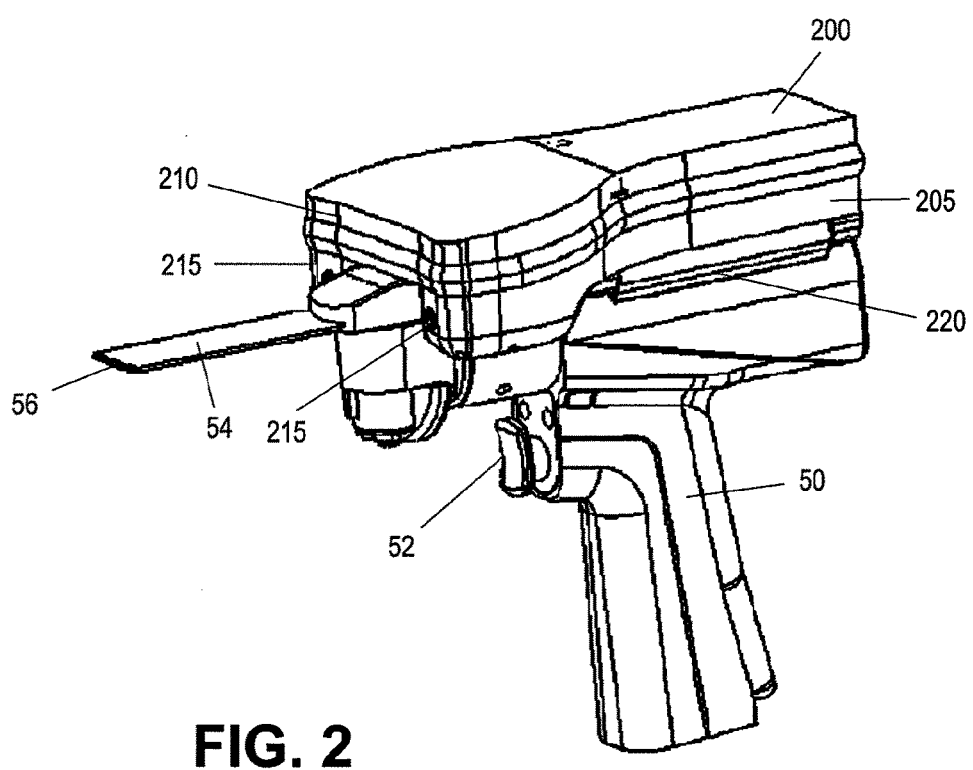
FIG. 2 illustrates an isometric view of an on tool tracking device attached to a surgical instrument.

FIG. 2 is an isometric view of an on tool tracking device (OTT) 200 and arranged for tracking and providing guidance during computer aided surgery using the surgical instrument 50. The OTT 200 has a housing 205 that includes a pair of cameras 215, in an opening for projector output 210. The OTT 200 and also as a housing 205 with a surface 220 adapted and configured to mate with the surgical instrument 50. The surgical instrument 50 includes a trigger 52 for operating a tool 54 having an active element 56. An illustrative embodiment of FIG. 2 the tool 54 is a saw and the active element 56 is the serrated edge of the distal end thereof.

Figure 3:
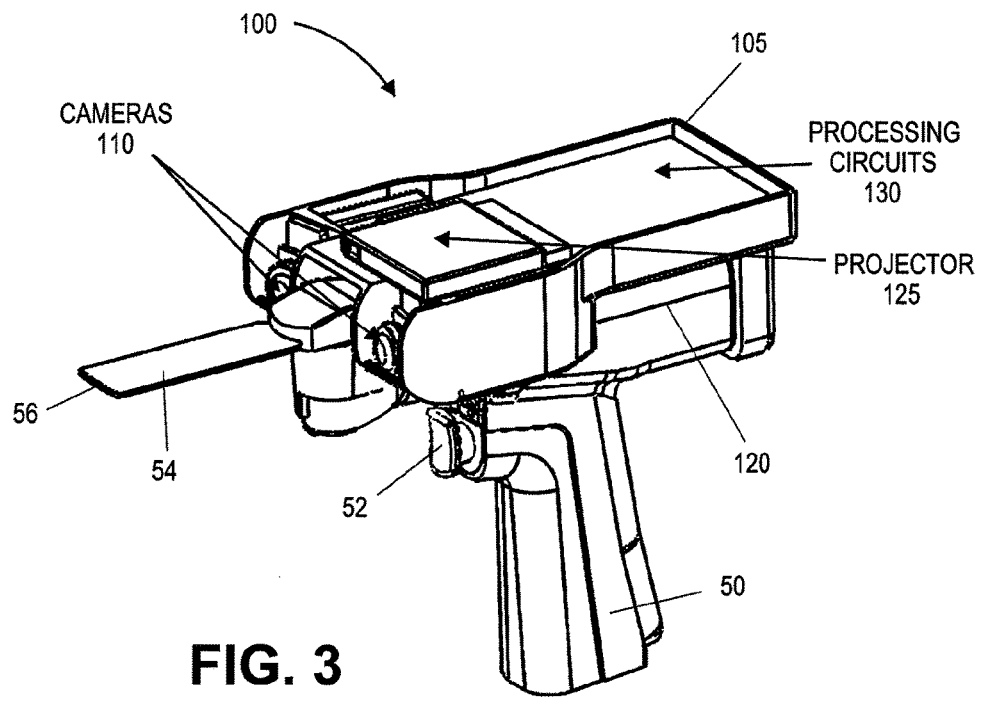
FIG. 3 illustrates an isometric view of the on tool tracking device of FIG. 1 with a cover removed to show internal components.
Figure 4:
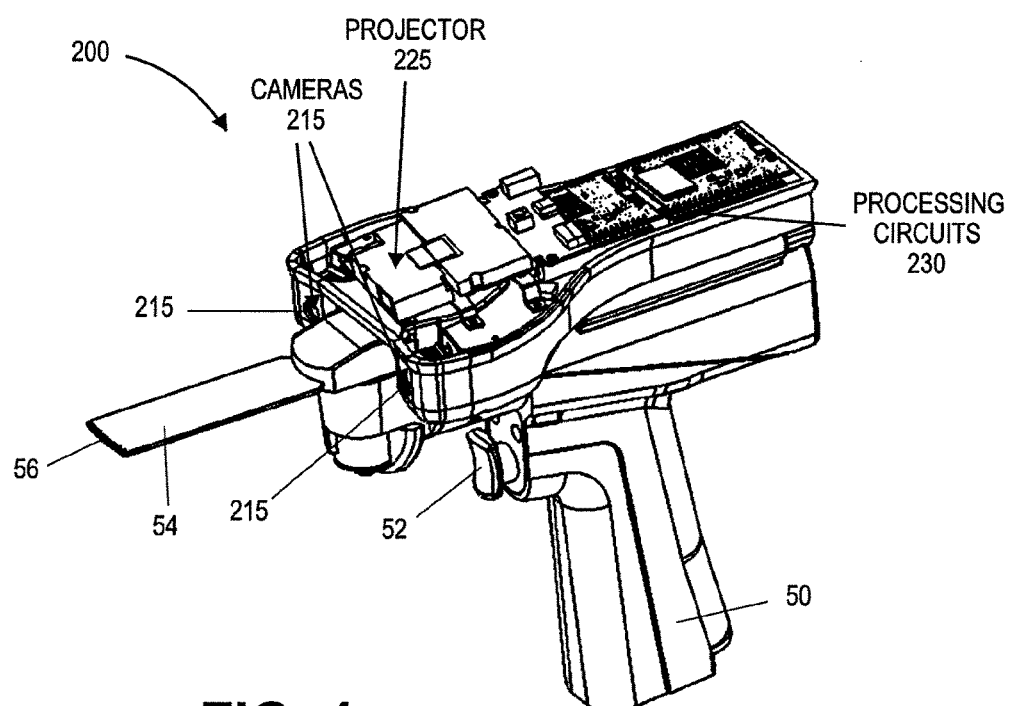
FIG. 4 illustrates an isometric view of the on tool tracking device of FIG. 2 with a cover removed to show internal components.

FIGS. 3 and 4 are isometric views of the on tool tracking devices of FIGS. 1 and 2 with the top cover of the housings removed. In the view of FIG. 3, the interior of the housing 105 exposed in shows the placement of the processing circuits 130, projector 125 and cameras 115. The output 110 of the projector 125 is illustrated in this embodiment in the position above a plane containing the cameras 115. In the view of FIG. 4, the interior of the housing 205 exposed in shows the placement of the processing circuits 230, projector 225 and cameras 215. The output 210 of the projector 225 is illustrated in this embodiment in a position above that at an acute angle with a plane containing the cameras 215.

Figure 5:
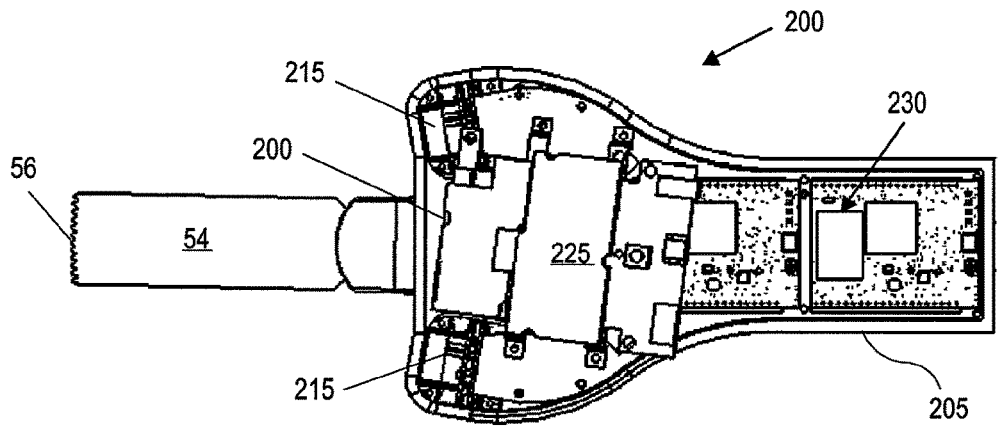
FIG. 5 illustrates a top down view of the on tool tracking device of FIG. 4
Figure 6:
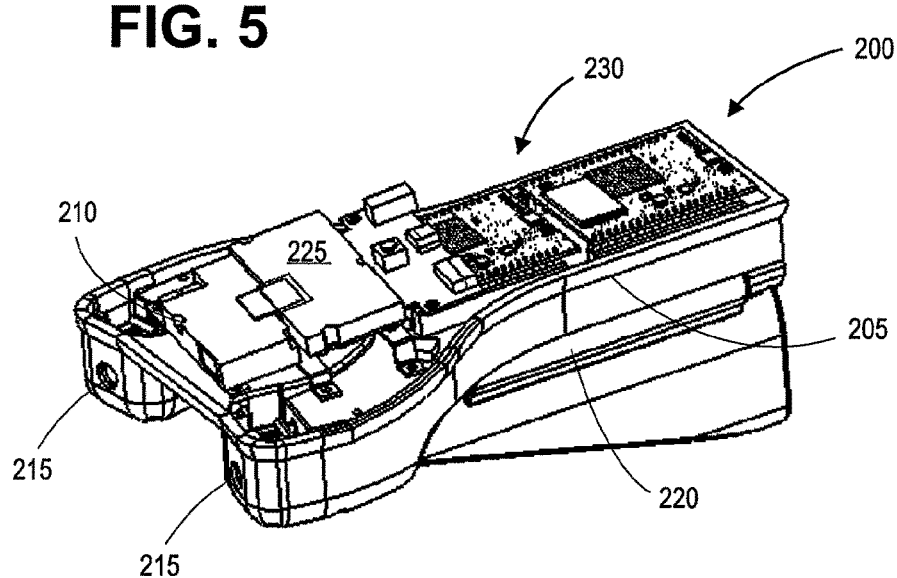
FIG. 6 illustrates an isometric view of the on tool tracking device of FIG. 5 separated from the surgical tool
Figure 7:
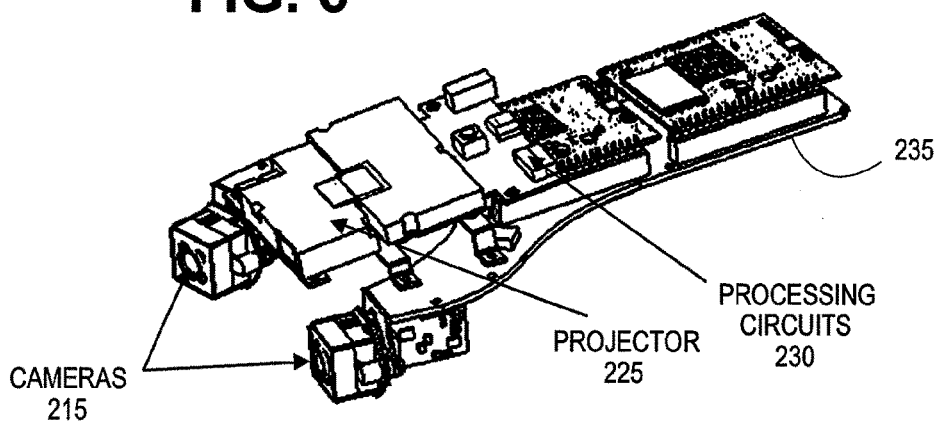
FIG. 7 illustrates electronics package and control circuitry visible in FIGS. 5 and 6 but in this view is removed from the OTT housing.

FIGS. 5, 6, and 7 represent one top down, and two isometric views of the on tool tracker 200. In the top down view of the on tool tracker shown in FIG. 4 the orientation and arrangement of the electronic components is clearly visible. As a result of the type of projector 225 used in this configuration, the projector has been positioned within the housing 205 at an angle and, as shown in FIG. 6 on a slightly inclined surface. In one embodiment, either or both of the cameras or the projector of an on tool tracking device may be positioned in any orientation and then the result of that orientation to the operation of the respective device is then compensated for in other ways as described herein. In this way, various different OTT electronic, the component designs are possible since the slight physical misalignments may be adjusted for using software techniques as described herein. FIG. 7 illustrates an isometric view of the electronic components of the on tool tracker 200 separated from the housing 205. This figure illustrates one embodiment of a quote one piece" OTT electronics package having cameras 215, projector 225 and associated processing electronics 230 on a single board 235 for placement within the housing 205.

Figure 8A:
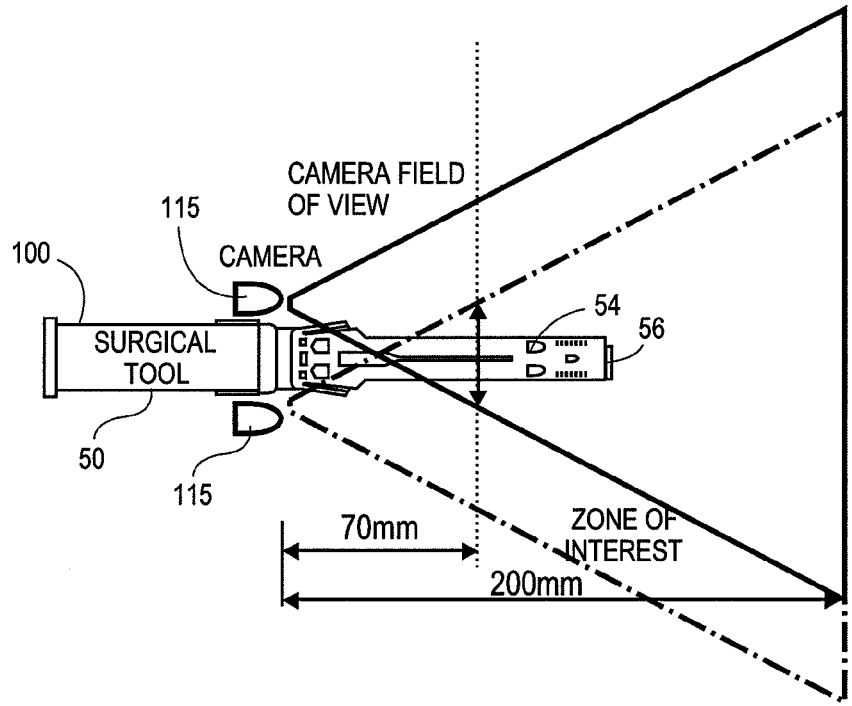
FIGS. 8A, 8B, 9, and 10 provide graphical information relating to the changes in camera field based on camera angle in some OTT device configurations.
Figure 8B:
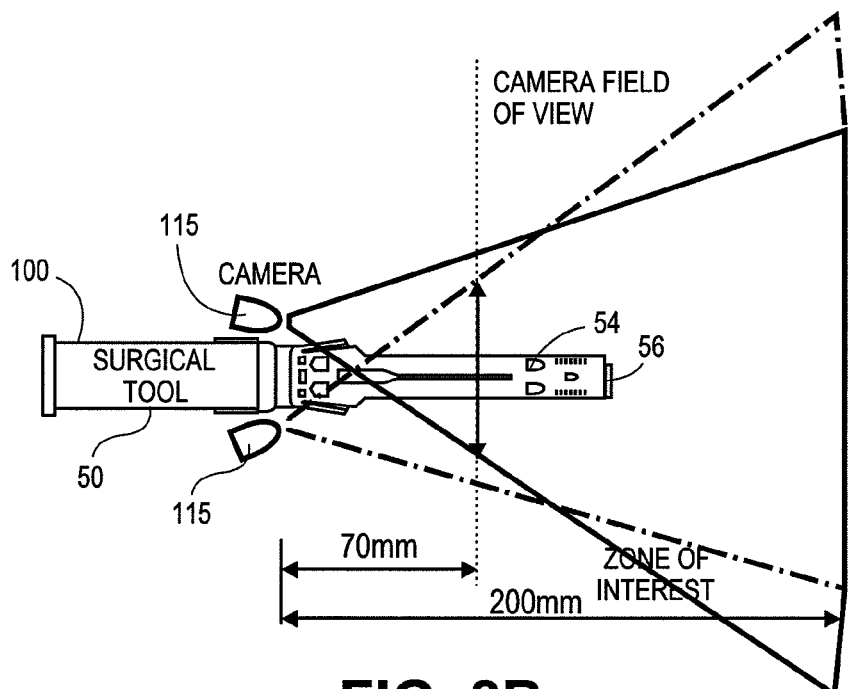
Figure 9:
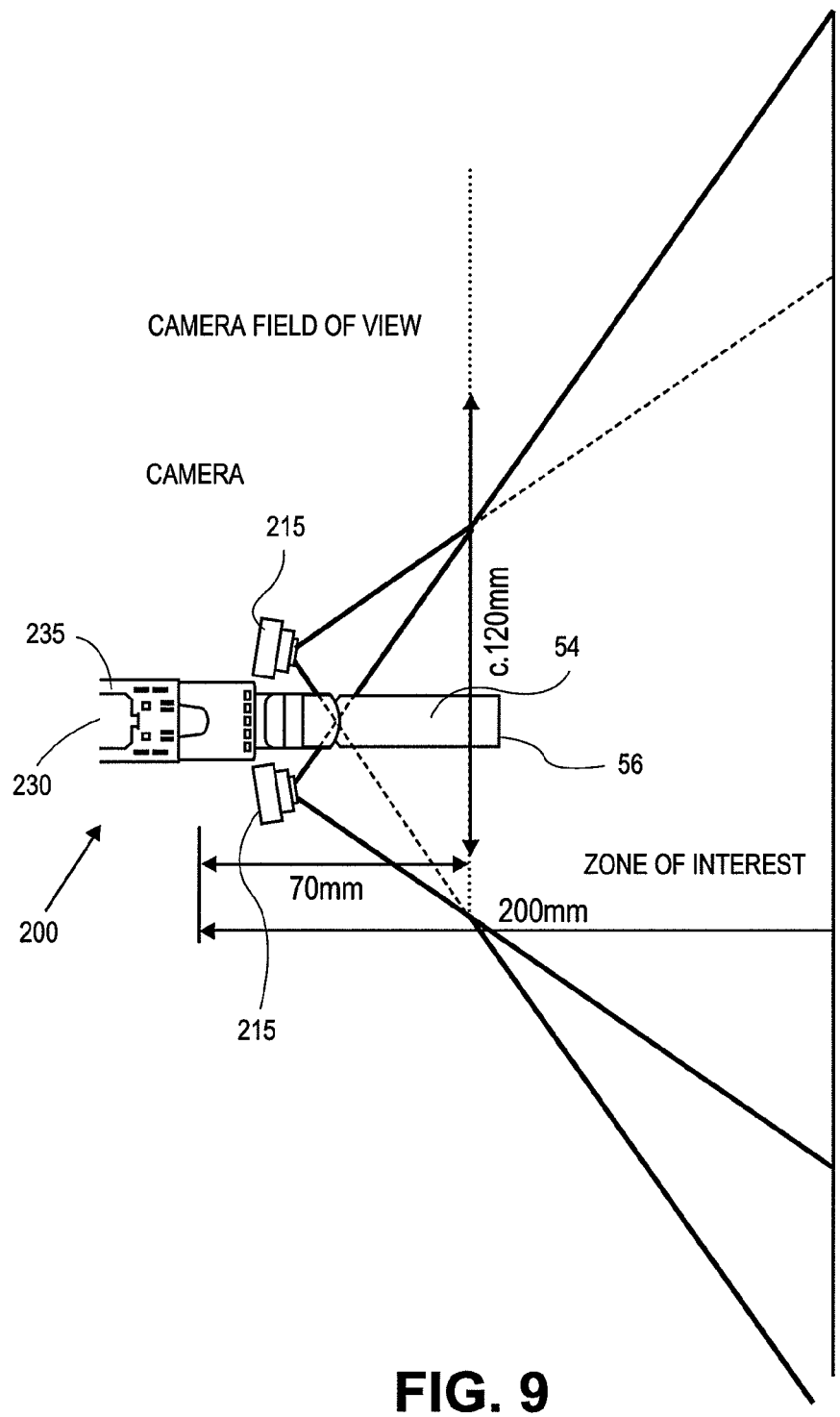
Figure 10:
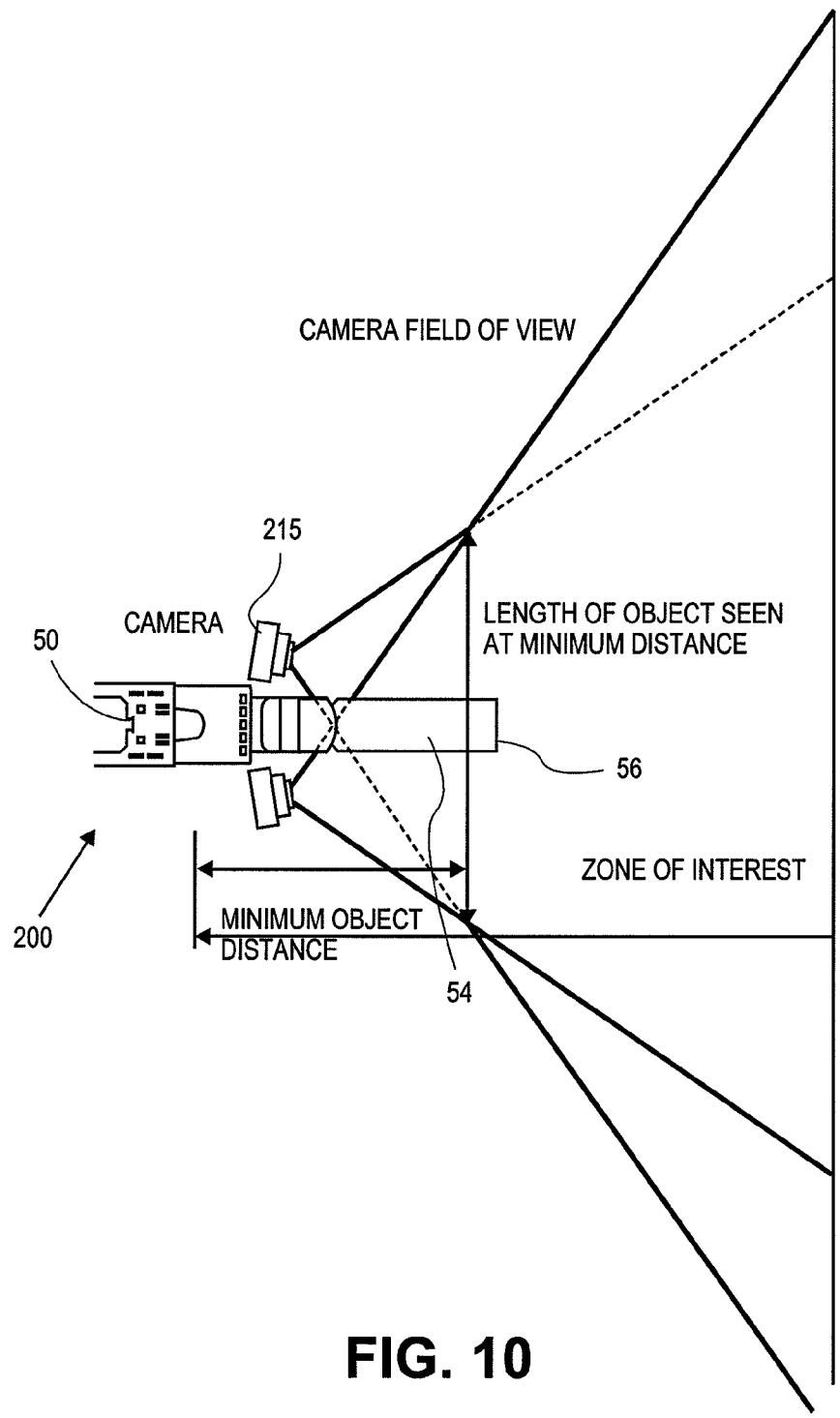

FIGS. 8A, 8B, 9 and 10 all illustrate the result on camera field of view for various camera angle orientations for the cameras included within an on tool tracking device. The cameras 115 in FIG. 8A are oriented in nearly parallel arrangement with regard to one another and the axis of the surgical tool 54. After accounting for blockage caused by other components, this configuration provides a camera field of view ranging from about 70 mm to about 200 mm. In other embodiments, the camera systems of an exemplary OTT device may operate in a camera field of view ranging from about 50 mm to about 250 mm. Is to be appreciated that the camera field of view may be physically or electronically altered depending upon the desired field of view needed for the particular computer aided surgery procedure that the OTT device will be used to perform.

Figure 11A:
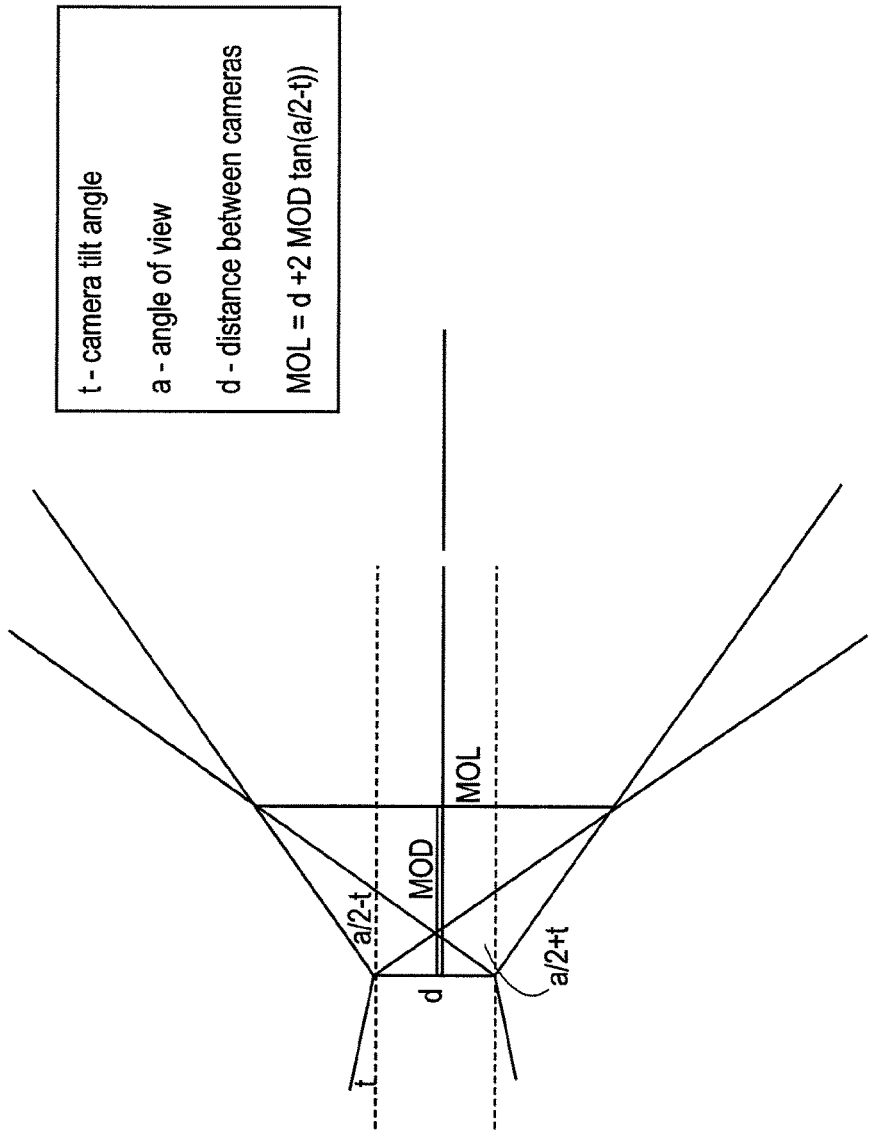
Figure 11C:
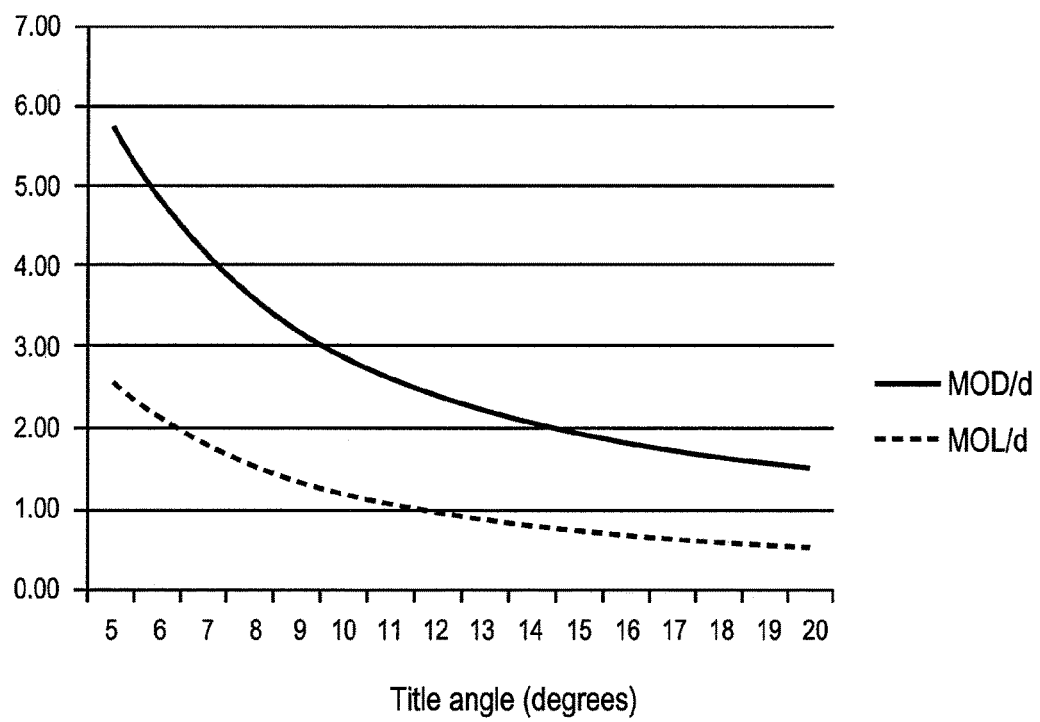
Figure 11D:
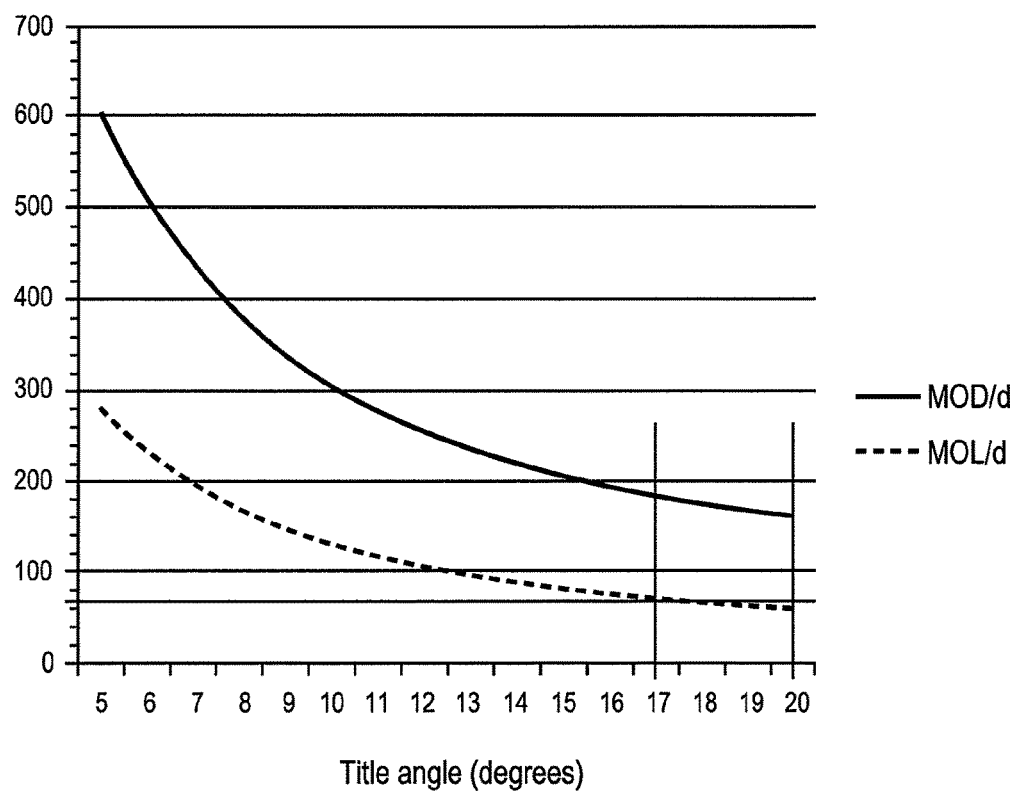

In contrast to the nearly parallel arrangement of the cameras in FIG. 8A, FIGS. 8B, 9 and 10 each demonstrate the result of different camera tilt angles and the resulting alteration of the camera field of view. The relationship of OTT camera positioning and tilt angle and their relationship to the angle of view, minimum object distance and maximum object length are better appreciated with reference to FIGS. 11A, 11B, 11C and 11D. FIG. 11A illustrates the geometric set up and formula for making the calculations used to produce the chart in FIG. 11B that relates tilt angle in degrees to a number of vision field factors. The data from this chart is related to tilt angle is reproduced in the graphs shown in FIGS. 11C and 11D. The optical field information presented in these figures is useful in the design and optimization of camera positioning in some of the various embodiments of the OTT devices described herein.

Figure 12A:
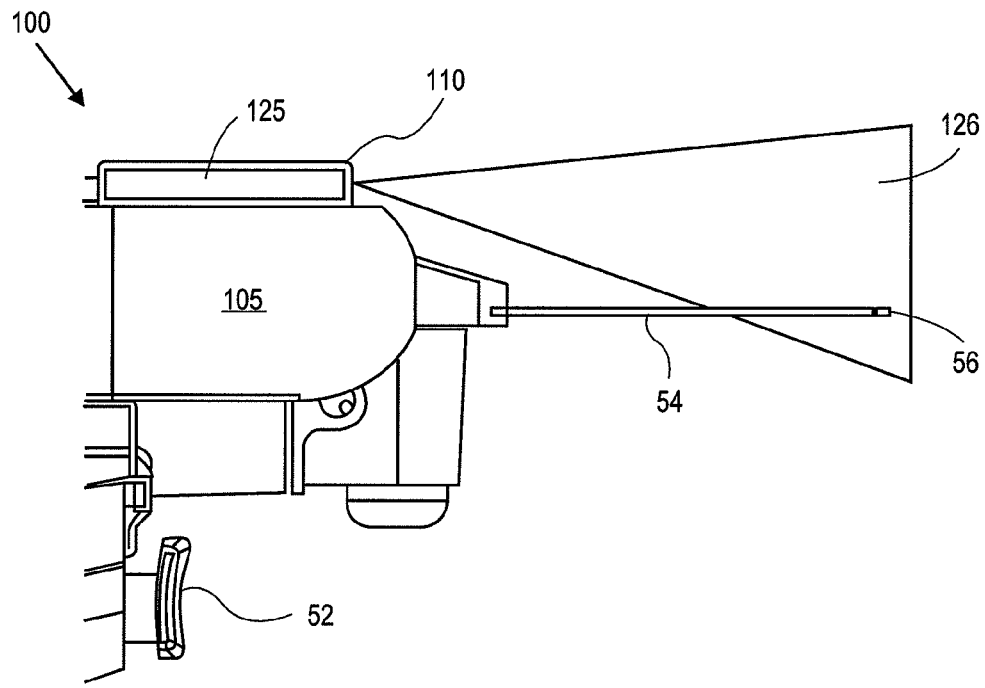
FIGS. 12A and 13A provide side and isometric views respectively of a projector used with an on tool tracking device.
Figure 12B:
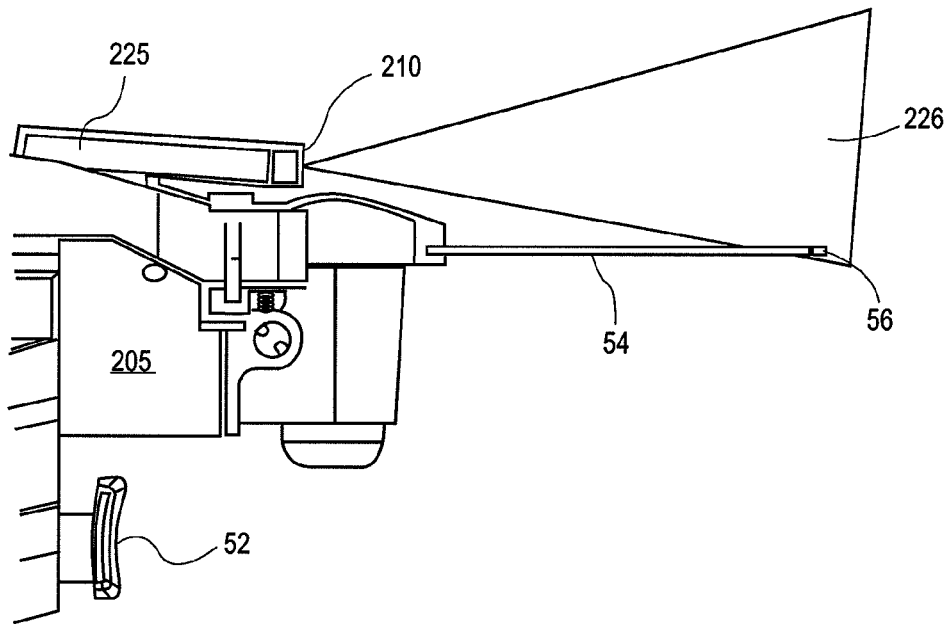
FIGS. 12B, 13B and 13C provide side, isometric and top views respectively of a projector in an angled orientation in use with an on tool tracking device.
Figure 13A:
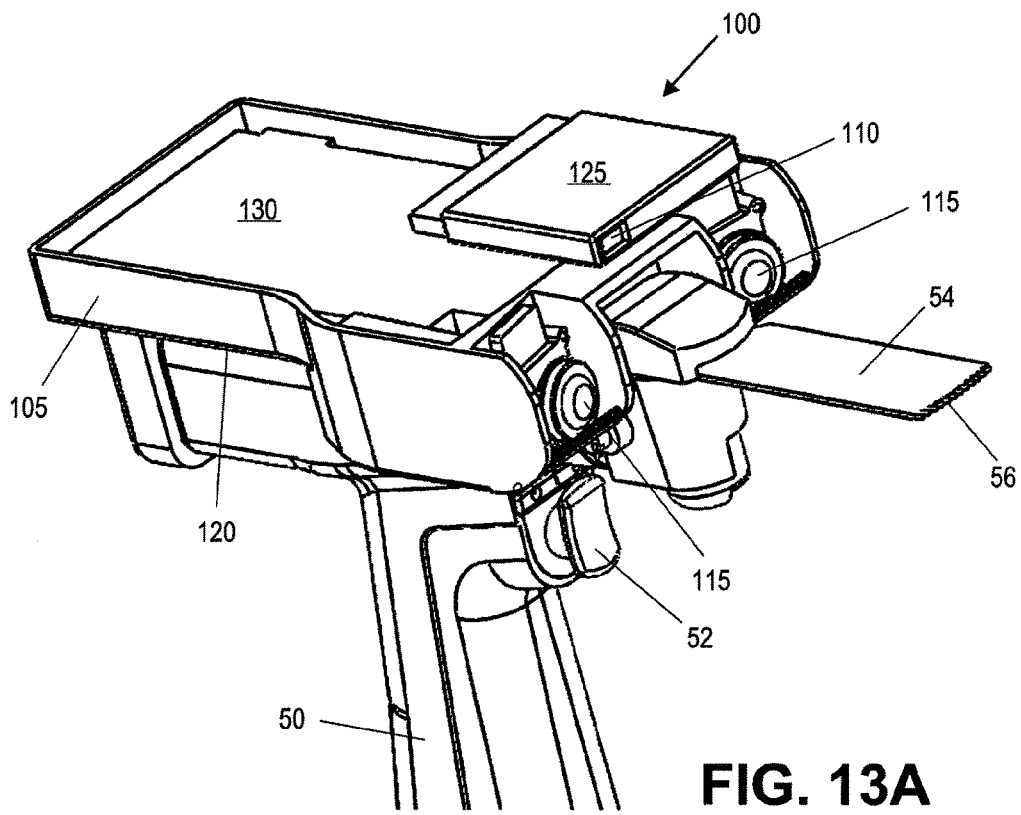
Figure 13B:
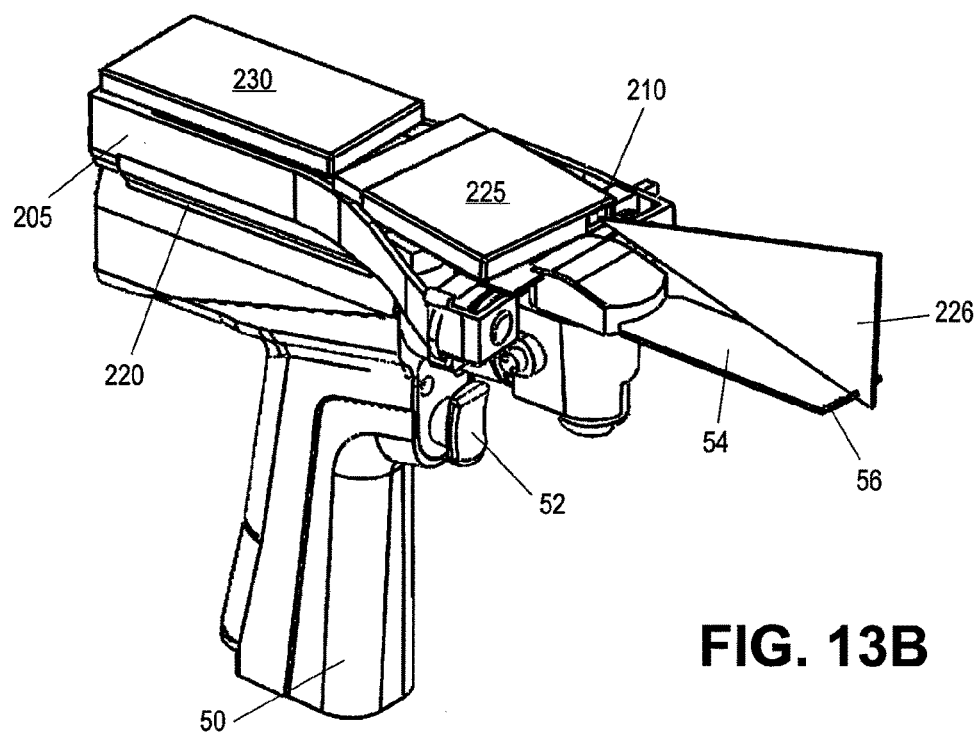
Figure 13C:
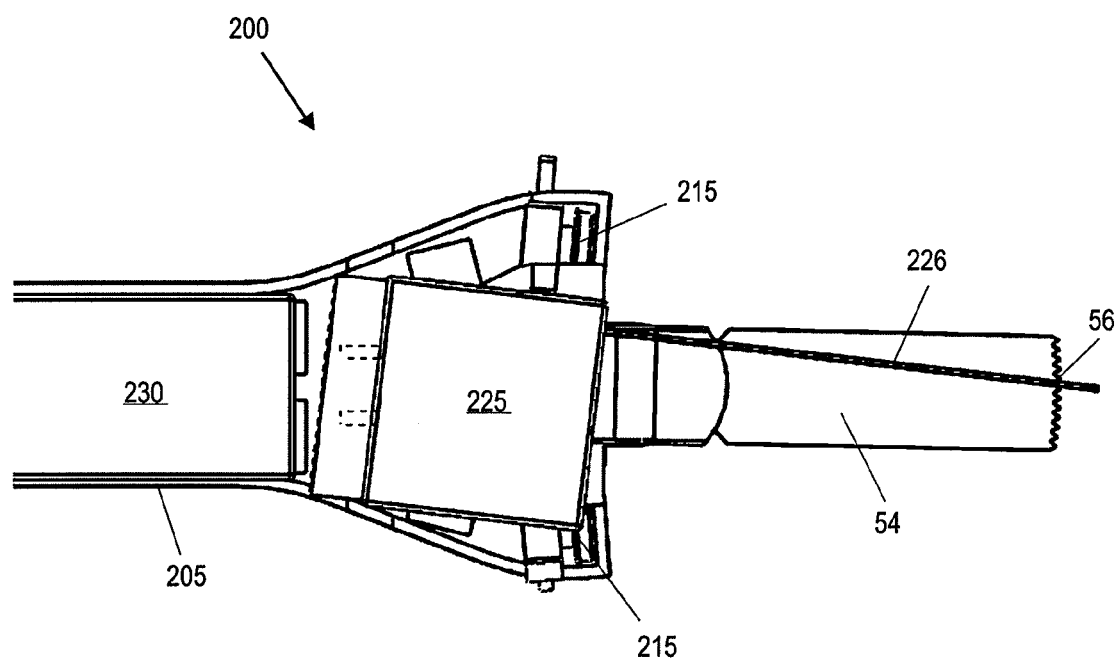

Additional aspects of the projector used with the various OTT embodiments may be appreciated for reference to FIGS. 12A, 12 B, 13A, 13B, and 13C. The impact on projector output based upon projector positioning within the OTT housing is demonstrated by a comparison between FIG. 12A and FIG. 12B. The projector 125 appears to be in a nearly planar relationship relative to the tool 54 as shown in both FIGS. 12A and 13A. However, notice how a portion of the projector output 126 extends beyond and below the tool distal end 56. In contrast, the projector 225 is positioned at an acute angle in relation to the tool 54. Additionally, the projector output to 10 is off to one side when compared to its relative position between the cameras 215. However, the projector output 226 is mostly above the blade 54 and crosses only at the distal end 56. Additional aspects of the projector output to 26 are apparent upon review of the views in FIGS. 13B and 13B. It is to be appreciated that the projector outputs, projector size and orientations described in these embodiments is not limiting to all OTT device embodiments. A suitable OTT projector may be configured in a number of satisfactory ways and placement within the OTT housing may be adjusted based on package size of a desired projector. As is clearly illustrated by the sample outputs of the projector 225, many different projector sizes, orientations and angular relationships may be used and still effectively operated to meet the projector requirements of the OTT CAS processing system. In other words, a wide variety of projector types, output locations and packaging may be used and still remain within the various embodiments of the OTT devices described herein.

Embodiments of the OTT device of the present invention are provided with a variety of imaging, projector and electronic components depending upon the specific operational characteristics desired for a particular OTT CAS system. The illustrative embodiments that follow are provided in order that the wide variety of characteristics and design factors may be appreciated for this part of the OTT CAS system.

Figure 14A:
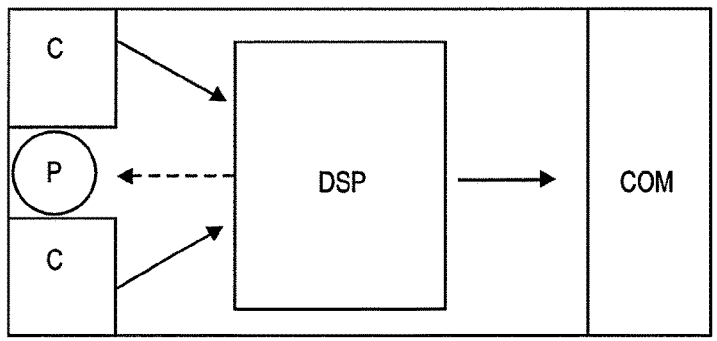
FIGS. 14A, 14B, 15A, and 15B each illustrate schematic views of several different electronic component configurations used by some on tool tracking device embodiments.

FIG. 14A illustrates a schematic of an embodiment of an OTT device. In this illustrated embodiment, there is provided Camera/dsp/processing NaturalPoint Optitrak SL-V120 range Computer: PC—Windows 2000/XP/Vista/7; 1.5 GHz Processor; 256 MB of RAM; 5 MB of free hard disk space; USB 2.0 Hi-Speed port (minimum, faster is better)

COM: DYNADOCK W20 Port Replicator with Wireless USB support;

Projector: Microvision's SHOWWX Laser Pico Projector that are arranged within the OTT housing as shown in the view. This embodiment makes use of what is known as 'smart cameras'—cameras that have the capability of performing localized image processing. This processing can be programmable usually through Field Programmable Gate Arrays (FPGAs). The configuration of the components in this specific embodiment are utilized to provide image processing that occurs both on the OTT devices and on a OTT CAS computer. For example, DSP on the OTT device detects and processes marker data before transferring it to the OTT CAS computer. The configuration greatly reduces processing power required on the host computer while also minimizing the data needed to transmit. It is to be appreciated that the schematic view, while useful primarily to show the type of imaging, data processing and general computer processing capabilities of a particular OTT device or as between an OTT device and a OTT CAS computer, this view may not reflect the actual orientation, spacing and/or alignment between specific components. Electronic communications capabilities (COM) are provided via wired connection or any suitable wireless data transfer mode from and to a computer that is adapted and configured for use with OTT CAS processes, algorithms and modes described herein. The type, variety, amount, and quality of the processing data exchange between the OTT device and an OTT CAS computer (if used) will vary depending upon the specific parameters and considerations of a particular OTT CAS procedure, mode or system utilized.

Figure 14B:
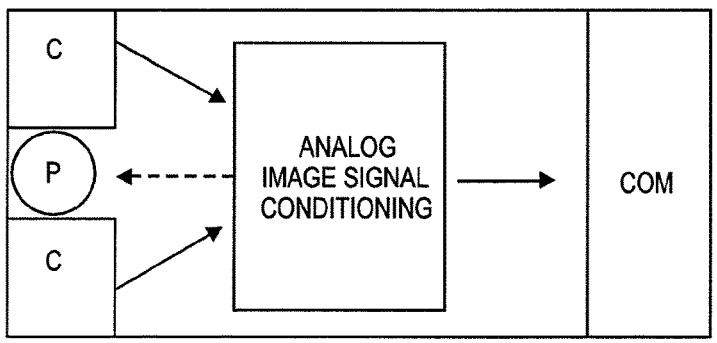

FIG. 14B illustrates a schematic of an embodiment of an OTT device. In this illustrated embodiment, there is provided Camera: Analog camera wired or wireless; eg FPV wireless camera DSP: uCFG Microcontroller Frame Grabber. This is connected to the PC PCI bus and becomes part of the PC.

Computer: Computer: PC—Windows 2000/XP/Vista/7; 1.5 GHz Processor; 256 MB of RAM; 5 MB of free hard disk space; USB 2.0 Hi-Speed port (minimum, faster is better)

COM: Hardwiring or Analog wireless transmitter

Projector: Microvision's SHOWWX Laser Pico Projector that are arranged within the OTT housing as shown in the view. The configuration of the components in this specific embodiment are utilized to provide use of low cost commodity cameras where no image processing for tracking is performed onboard the OTT and the image signal is captured by a dedicated frame grabber that is part of the PC. The frame grabber accepts the captured image and deposits it into PC memory without any overhead processing by the PC. This embodiment results in a smaller, lighter and lower cost OTT device.

It is to be appreciated that the schematic view, while useful primarily to show the type of imaging, data processing and general computer processing capabilities of a particular OTT device or as between an OTT device and a OTT CAS computer, this view may not reflect the actual orientation, spacing and/or alignment between specific components. Electronic communications capabilities (COM) are provided via wired connection or any suitable wireless data transfer mode from and to a computer that is adapted and configured for use with OTT CAS processes, algorithms and modes described herein. The type, variety, amount, and quality of the processing data exchange between the OTT device and an OTT CAS computer (if used) will vary depending upon the specific parameters and considerations of a particular OTT CAS procedure, mode or system utilized.

Figure 15A:
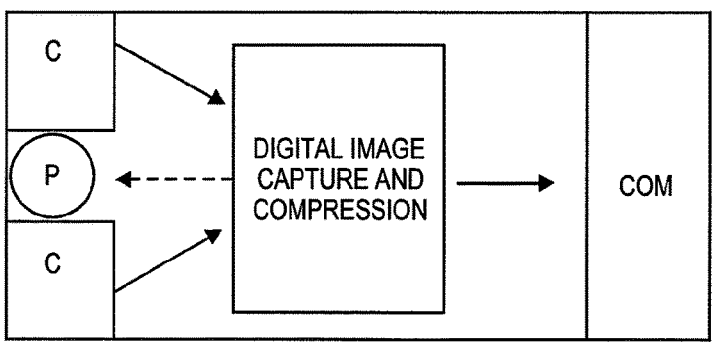

FIG. 15A illustrates a schematic of an embodiment of an OTT device. This embodiment utilizes commodity USB cameras with incorporated electronic circuitry that captures the image from the camera and conditions it to be USB compatible. This output is compressed and then transmitted through wires or wirelessly without further tracking related processing.

In this illustrated embodiment, there is provided

Camera: Microsoft LifeCam

Computer: Dell Precision R5500 Rack Workstation

COM: Carambola 8 devices Core, or DTW-200D (CDMA2000 1X) and DTW-500D (EVDO Rev A)

Projector: Microvision's SHOWWX Laser Pico Projector that are arranged as shown in the view. The configuration of the components in this specific embodiment are utilized to provide a modular solution for providing the electronic OTT components. This embodiment uses commodity low cost cameras and allows the cameras to be used in a modular form where they can be changed or upgraded to reflect advances in technology without disrupting the OTT or the ground based systems.

There is no need to use an on-tool DSP if the OTT CAS computer is optimized for DSP. This embodiment makes it possible to use any of the commercially available image processing libraries. For example, Halcon image processing software takes only about 1 ms to process blobs (bone reference frame LEDs) and compute their centroids. Images can therefore be sent directly from the OTT tool to the OTT CAS Computer to be processed. It is important that the COM will need to be selected to handle higher bandwidth when compared to other embodiments. Similarly, the Computer will need to be selected to handle more burdensome computation.

It is to be appreciated that the schematic view, while useful primarily to show the type of imaging, data processing and general computer processing capabilities of a particular OTT device or as between an OTT device and a OTT CAS computer, this view may not reflect the actual orientation, spacing and/or alignment between specific components. Electronic communications capabilities (COM) are provided via wired connection or any suitable wireless data transfer mode from and to a computer that is adapted and configured for use with OTT CAS processes, algorithms and modes described herein. The type, variety, amount, and quality of the processing data exchange between the OTT device and an OTT CAS computer (if used) will vary depending upon the specific parameters and considerations of a particular OTT CAS procedure, mode or system utilized.

Figure 15B:
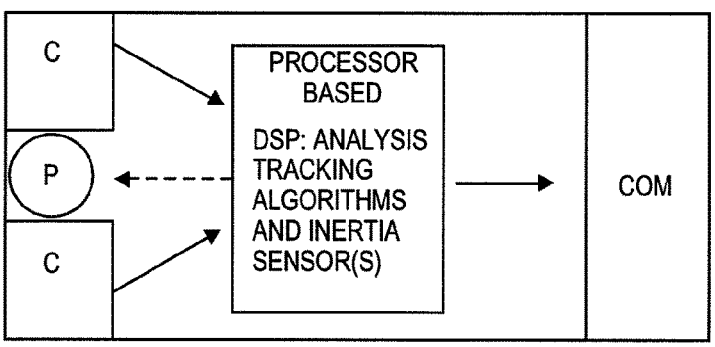

FIG. 15B illustrates a schematic of an embodiment of an OTT device. In this illustrated embodiment, there is provided Camera: Smart camera as in FIG. 15A or USB camera as in FIG. 15C Inertia Sensors: Bosch SMB380, Freescale PMMA7660, Kionix KXSD9

Onboard processor: ARM processor

Computer: Computer: PC—Windows 2000/XP/Vista/7; 1.5 GHz Processor; 256 MB of RAM; 5 MB of free hard disk space; USB 2.0 or USB 3.0 Hi-Speed port (minimum, faster is better)

COM: Standard IEEE 802.11 communications protocol or similar protocol for communication between the OTT borne processor and the ground station PC.

Projector: Microvision's SHOWWX Laser Pico Projector that are arranged as shown in the view. The configuration of the components in this specific embodiment are utilized to provide an embodiment that performs complex processing onboard the OTT device to accomplish most of the body tracking as needed for purposes of OTT CAS procedures. The device is a complete stand-alone tracking device. The OTT device further contains one or more inertia sensors. DSP involves the use of Inertia sensors to predict the location of the fiducials in the 'next frame'. As a result, the computational burden on the DSP on the OTT device is minimized.

It is to be appreciated that the schematic view, while useful primarily to show the type of imaging, data processing and general computer processing capabilities of a particular OTT device or as between an OTT device and a OTT CAS computer, this view may not reflect the actual orientation, spacing and/or alignment between specific components. Electronic communications capabilities (COM) are provided via wired connection or any suitable wireless data transfer mode from and to a computer that is adapted and configured for use with OTT CAS processes, algorithms and modes described herein. The type, variety, amount, and quality of the processing data exchange between the OTT device and an OTT CAS computer (if used) will vary depending upon the specific parameters and considerations of a particular OTT CAS procedure, mode or system utilized.

In addition to the above described details and specific embodiments, it is to be appreciated that alternative embodiments of an OTT device may have electronic components including components with processing capabilities as well as software and firmware and electronic instructions to provide one or more of the following exemplary types of OTT CAS data in accordance with the OTT CAS processing methods, modes and algorithms described herein:

Receive and process visual and IR spectrum image data

Determining coordinates of the centroid of each of the markers within image frame Determining the sizes of all markers within an image frame Reporting the size and the coordinates of one or more fiducials Sub-pixel analysis to determine the location of the centroid within an image frame, a marker placement or selected marker placements Variable and controllable frame rate from 20 to 60 frames per second based on input from central computer or internal instructions or in response to an OTT CAS processing mode adaptation FIGS. 16A, 16B and 16C provide various views of a reference frame 300 for use in a computer assisted surgery procedure. There is a 305 frame having a surface 310 bounded by perimeter 315. One or more active or passive fiducial marker 70 are arranged in a pattern 72 across the surface 310. There is a stem 320 extending from the frame 305 and a coupling 325 on the stem. The coupling 325 is used to join the frame 305 to a base 330. The base 330 has a first surface 335 configured to engage a portion of the anatomy within a surgical field related to the procedure. The base 330 has a second surface 340 to engage with the coupling 325. The coupling 325 and the second surface 340 are engaged in FIG. 16A but are separated in FIGS. 16B and 16C. In the views of FIGS. 16C and 16C at least one registration element is visible on the coupling and at least one registration element is visible on the second surface. In the illustrated embodiment, the registration element 342b is a female feature on the coupling 325 while the coupling element 325a on the second surface 340 is a male feature. The registration elements are sized and positioned to mating cooperation when the coupling 325 and the second surface 340 are engages. It is to be appreciated that a variety of different registration element types and positions may be adapted and configured for providing mating cooperation when the coupling is engaged to the second surface.

The base 330 includes a second surface 335 used to engage the anatomy. All or a portion of the surface may include a serrated edge to assist in engaging with anatomy, particularly bony anatomy about the joint. The base first surface 335 comprises a curvature that is complementary to the anatomical site upon which the base first surface is to be affixed during the surgical procedure. In one embodiment, the bony portion of the anatomy is adjacent to a joint that is the subject of the surgical procedure. The joint may be selected from a knee, a shoulder, a wrist, an ankle, a hip, or a vertebrae. The base 330 includes at least one aperture 337 adapted and configured for a fixation element used to affix the base to a site on the body. The fixation element may be selected from one or more of a pin, a screw, a nail, or surgical staple.

Figure 17:
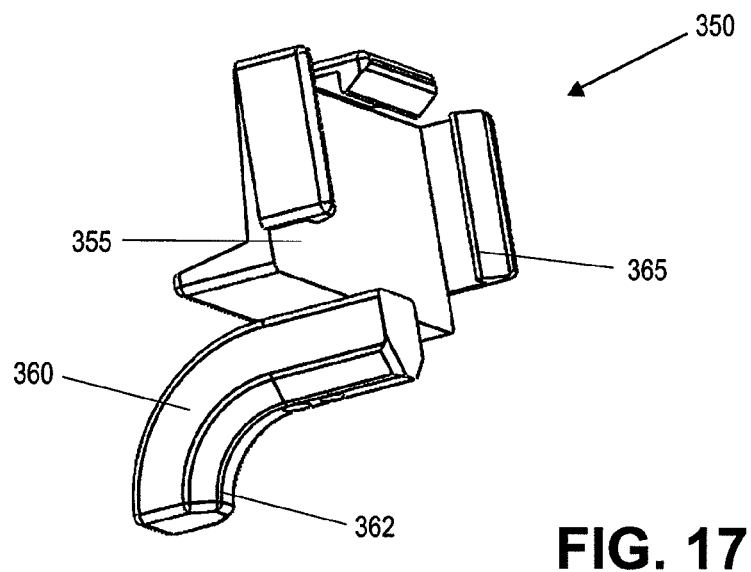
FIG. 17 illustrates an isometric view of a reference frame guide and FIG. 18 illustrates the guide of FIG. 17 attached to the reference frame of FIG. 16A.
Figure 18:
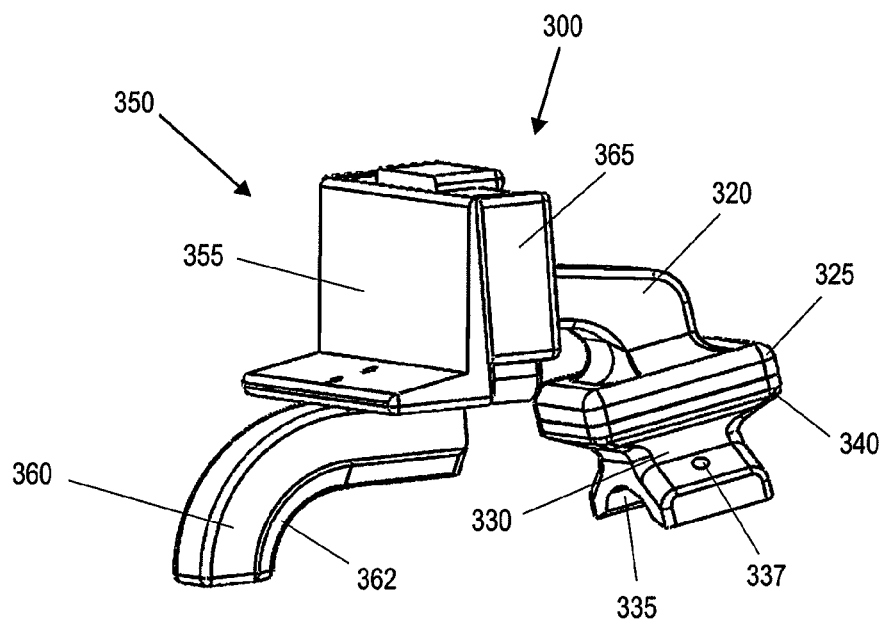

FIG. 17 illustrates an isometric view of the reference frame guide 350. The reference frame guide 350 has a frame 355 and a stem 360 extending from the frame 355. The stem 360 has a curvature or shape configured to engage with an anatomical feature to assist, when the frame guide is attached to the frame 305, the reference frame 300 is placed in a desired position and orientation within the surgical field. The reference frame guide 350 also includes one or more engagement elements 365 along the frame 355 for temporary engagement with the perimeter 315 or a portion of the reference frame 305 to permit proper positioning and adjustment of a base 330 associated with a reference frame 300 attached using the elements 365. FIG. 18 illustrates a reference frame guide attached to the frame 305 of a reference frame 300. In use, the engagement elements 365 may be broken off in order to remove the reference frame from the guide frame during surgical procedure. While illustrated in mating cooperation with reference frame 300, reference frame guide 350 may be adapted and configured to form a mating engagement with reference frames of different shapes and sizes, such as the reference frame 400 in FIG. 24.

Figure 19:
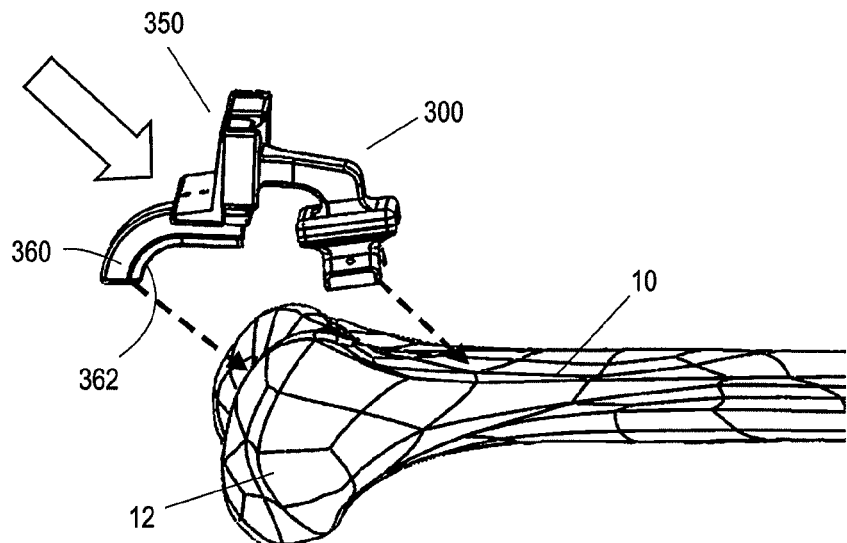
FIG. 19 illustrates the components of FIG. 18 being moved and position for attachment to the anatomy and FIG. 20 is an isometric view illustrating said attachment.
Figure 20:
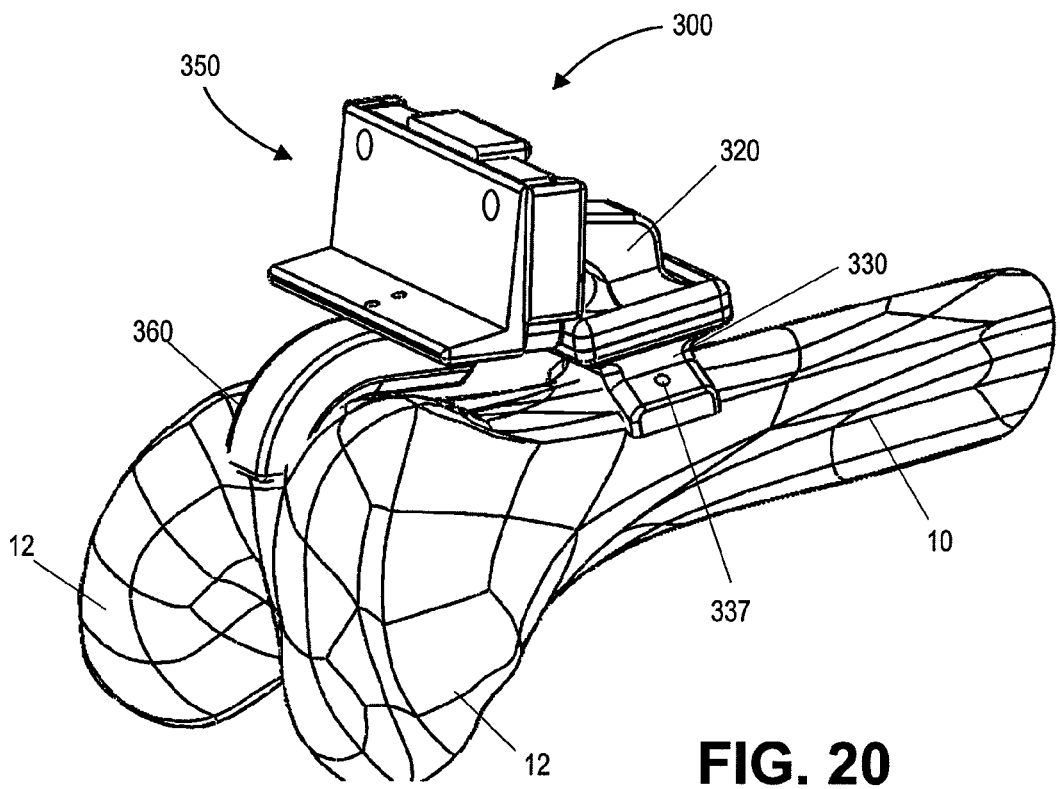
Figure 21:
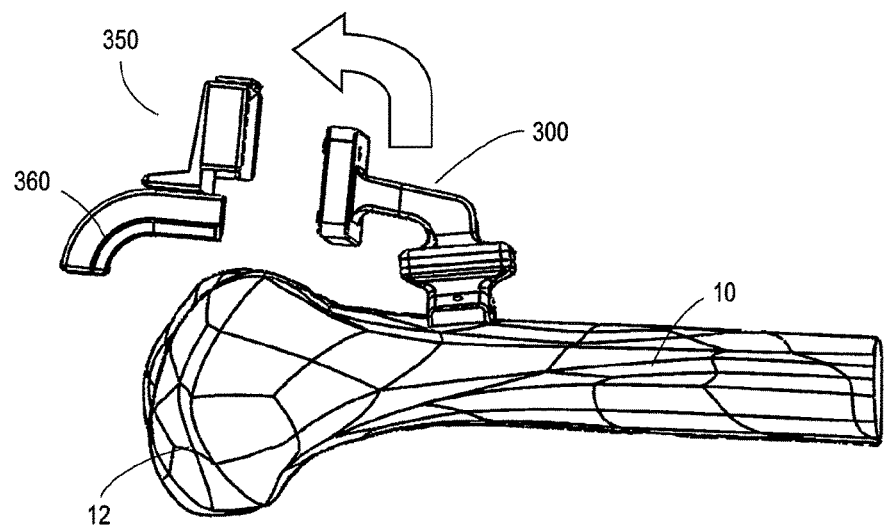
FIG. 21 illustrates the removal of the guide frame and FIG. 22 illustrates the remaining frame in position on the anatomy.
Figure 22:
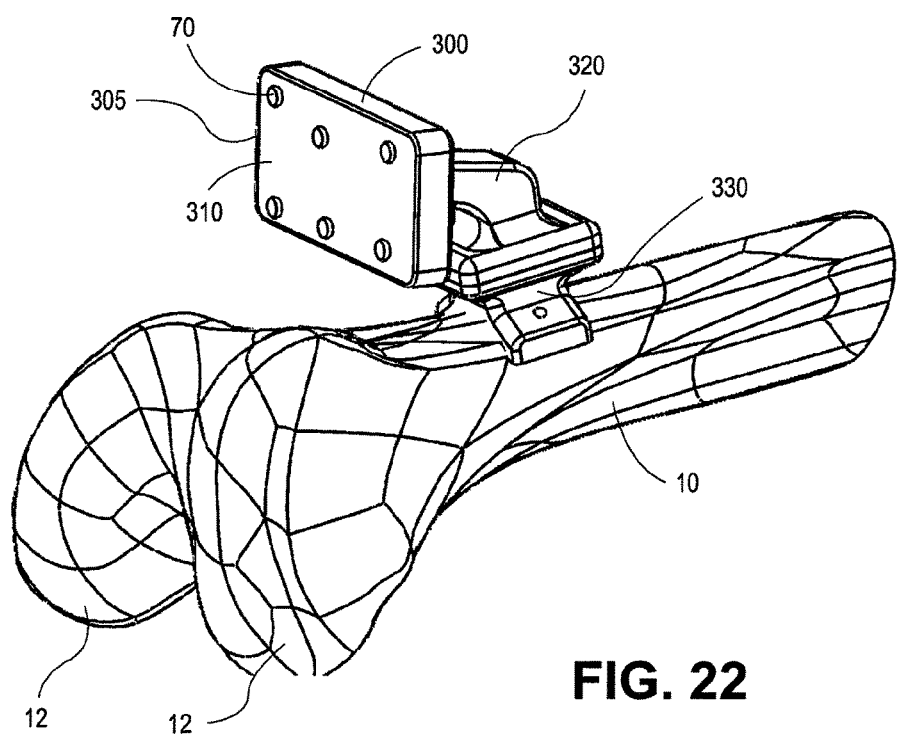

In one particular embodiment, the curvature or shape 362 of the stem 360 is configured for placement of the stem in relation to the condyles in order to provide alignment within the surgical field for the reference frame 300 along the femur. Positioning of the base 330 along the femur 10 is shown in FIGS. 19 and 20. The joint reference frame guide and reference frame structure (see FIG. 18) is positioned (following the arrow in FIG. 19) so as to align the curvature 362 of the stem 360 between the condoyles 12 of the femur 10 in order to place the base 330 in proper orientation on the femur as shown in FIG. 20. Thereafter the reference frame 300 is attached to the femur 10 by joining the base first surface 335 using one or more methods such as and screws or nails applied the aperture 337 or the use of a biocompatible bone cement. Once the reference frame 300 is confirmed in the proper position, the reference frame guide 350 is removed (FIG. 21) leaving only the reference frame in the desired location along the femur 10 in the desired relation to the condyles 12 according to a surgical plan to be implemented (FIG. 22).

Figure 23:
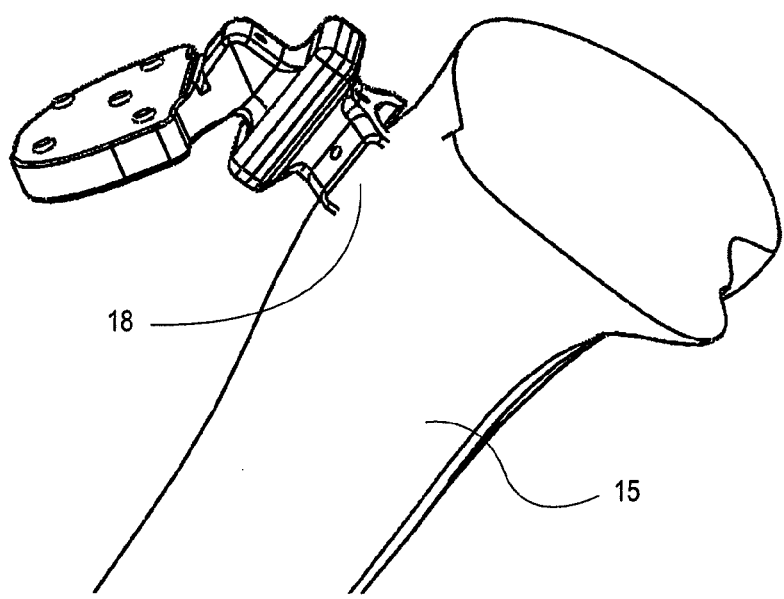
FIG. 23 illustrates another reference frame in position on the tibia.
Figure 25:
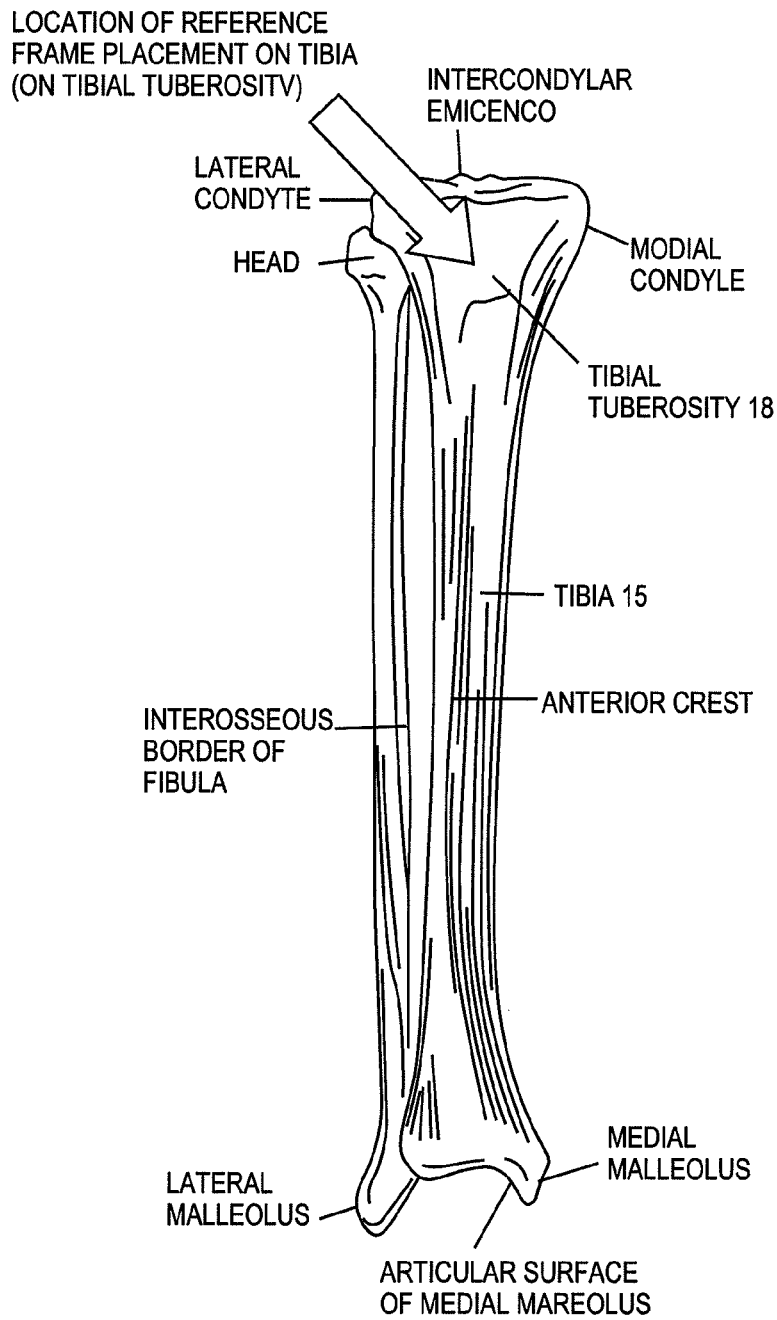
FIG. 25 illustrates an implantation site on the tibia.

FIG. 23 illustrates an embodiment of the reference frame 400 and position along the tibia 15. In this illustrated embodiment the reference frame 400 is attached on or about the tibial tuberosity (shown more clearly in FIG. 25) and secured to the bone using anyone of the several fixing methods described above with regard to the reference frame 300. Additional details of the reference frame 400 may be provided upon review of FIGS. 24A, 24B and 24C. These figures provide various views of a reference frame 400 for use in a computer assisted surgery procedure. There is a 405 frame having a surface 410 bounded by perimeter 415. One or more active or passive fiducial marker 70 are arranged in a pattern 74 across the surface 410. There is a stem 420 extending from the frame 405 and a coupling 425 on the stem. The coupling 425 is used to join the frame 405 to a base 430. The base 430 has a first surface 435 configured to engage a portion of the anatomy within a surgical field related to the procedure. The base 430 has a second surface 440 to engage with the coupling 425. The coupling 425 and the second surface 440 are engaged in FIG. 24A but are separated in FIGS. 24B and 24C. In the views of FIGS. 24C and 24C at least one registration element is visible on the coupling and at least one registration element is visible on the second surface. In the illustrated embodiment, the registration element 442b is a female feature on the coupling 425 while the coupling element 425a on the second surface 440 is a male feature. The registration elements are sized and positioned to mating cooperation when the coupling 425 and the second surface 440 are engages. It is to be appreciated that a variety of different registration element types and positions may be adapted and configured for providing mating cooperation when the coupling is engaged to the second surface.

The base 430 includes a second surface 435 used to engage the anatomy. All or a portion of the surface may include a serrated edge to assist in engaging with anatomy, particularly bony anatomy about the joint. The base first surface 435 comprises a curvature that is complementary to the anatomical site upon which the base first surface is to be affixed during the surgical procedure. In one embodiment, the bony portion of the anatomy is adjacent to a joint that is the subject of the surgical procedure. The joint may be selected from a knee, a shoulder, a wrist, an ankle, a hip, or a vertebrae. The base 430 includes at least one aperture 437 adapted and configured for a fixation element used to affix the base to a site on the body. The fixation element may be selected from one or more of a pin, a screw, a nail, or surgical staple.

Turning now to FIGS. 26A, 26B and 26C, additional aspects of the reference frame designed to be described. With reference to FIG. 26A, the orientation between the frame 305 and the base 300 may be adjusted between a number of preset orientations. Altering the relationship between these two components is accomplished by altering which of a plurality of registration elements available the joint is components are engaged. In one aspect, there are a plurality of registration elements on the coupling and a plurality of registration elements on the second surface. The orientation of the reference frame may be adjusted between a first orientation 382 and a second different orientation 384 based on which grouping of registration elements is used for joining the base 330 to the frame 305. In one embodiment, wherein a portion of the registration elements on the coupling are engaged with a portion of the registration elements on the second surface the result will orient the frame in a first orientation within the surgical field. In another aspect, the mating different registration elements on the coupling with different registration elements on the second surface, the result is that the frame 305 will present in a second, different orientation within the surgical field. In one aspect, the first orientation is a known position used in surgical preplanning. In still another aspect, the second orientation is a known position used in surgical preplanning. Either or both of the first orientation and the second orientation may be used in furtherance of the OTT CAS techniques described herein.

FIG. 26A also illustrates one embodiment of a mount coupling adapted and configured to maintain the relative position and orientation of the coupling and the second surface. In this embodiment a flexible linkage is shown between the two components and is sized shaped and oriented within the reference frame to maintain the orientation of the frame 305 within the surgical field. In other words, the mount coupling is sufficiently rigid that if the frame 305 is bumped during a procedure it will not lose its alignment. Is disposed completely within the structure in use, in another alternative aspect, a mount coupling is provided in so that when the mount coupling is attached to the reference frame the mount coupling substantially or completely surrounds the area of mating contact between the coupling and the second surface.

Figure 27A:
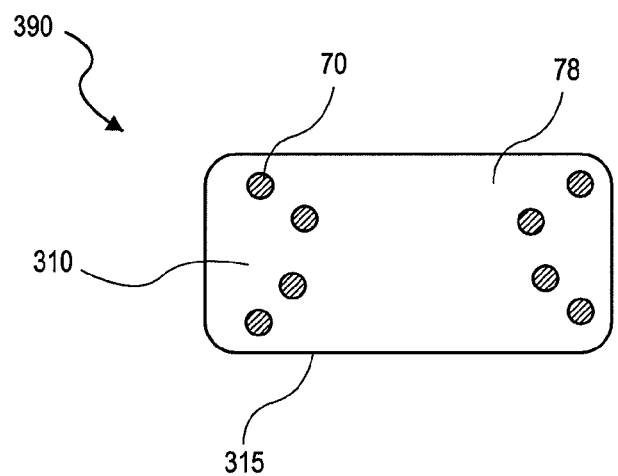
FIGS. 27A and 27B illustrate to alternative reference frame surfaces.
Figure 27B:
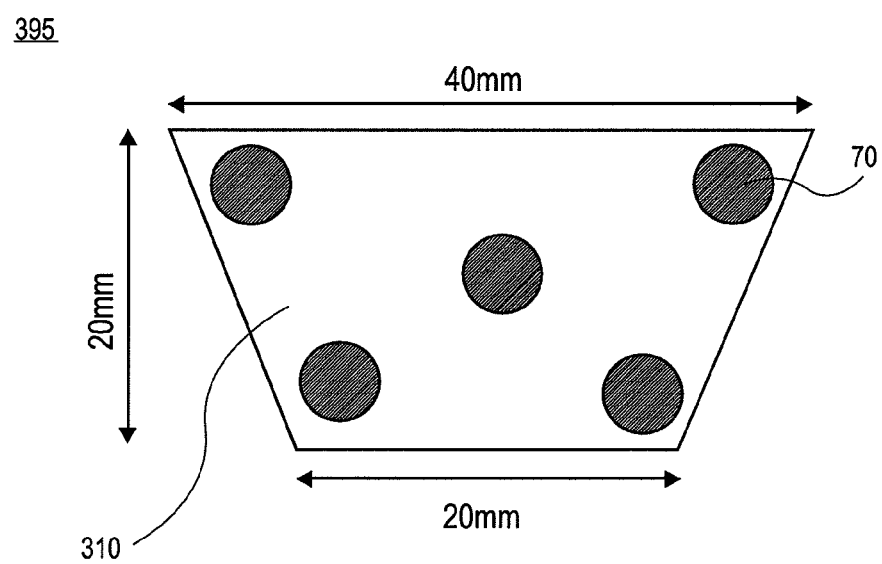

FIGS. 27A and 27B provide alternative reference frame surface shapes as well as alternative fight to show marker patterns. FIG. 27A illustrates a generally rectangular frame 390 of a reference frame having a plurality of fiducial markers 70 arranged in a pattern 78. FIG. 27B illustrates a generally trapezoidal surface shape 310 on the frame 395. A plurality of fiducial markers 70 arranged in a pattern on the surface 305.

Figure 28:
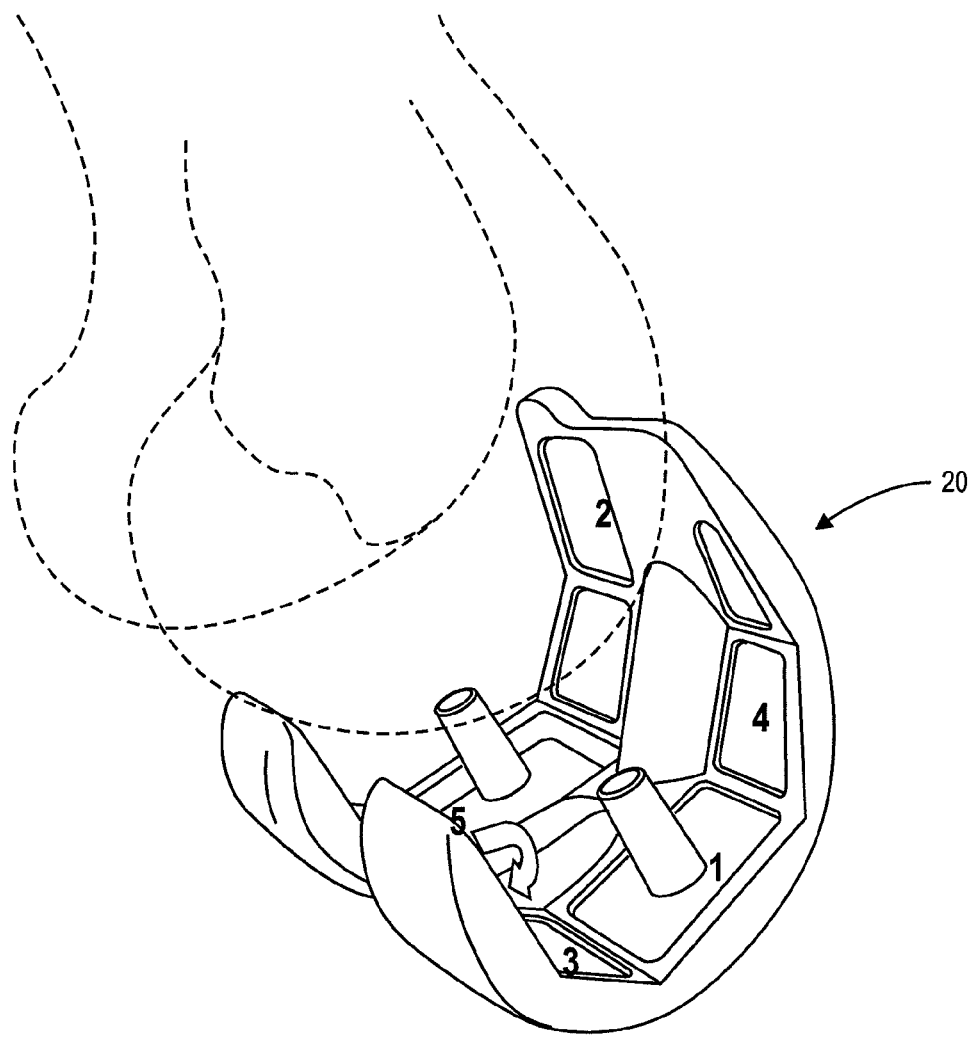
FIG. 28 is an isometric view of an exemplary knee prosthesis.

FIG. 28 illustrates an isometric view of a representative of thesis 20 for use in a total knee replacement procedure. The numbers indicated on the prosthesis 20 are representative of the types of cuts undertaken during knee surgery. FIGS. 29A-29I and 30 illustrate one of the unique combinations of the OTT CAS system described herein. While each of the reference frames described above may be used independently or in conjunction with other anatomical sites or surgical equipment, the reference frames 300 and 400 have particular advantage for the on tool tracking devices and OTT CAS procedures described herein. One challenge of using on tool tracking devices for handheld precut surgery is obtaining relevant tracking information and maintaining a tracking frame of reference during the procedure. By the unique design and placement the reference frames 300 and 400 may be used to provide just this type of dynamic reference frame tracking using the OTT tracking techniques described herein. As shown in the figures that follow in each one of the representative cuts used for implanting the prosthetic 20, the vision system carried onboard the OTT 100 is able to visually identify and register with all or a portion of the reference frame 300 and the reference frame 400. While these particular configurations are illustrative of the capabilities of the OTT CAS system and tools for knee surgery, it is to be appreciated that the reference frames and vision guidance techniques described herein may be adapted to other joints in the body and to other procedures.

FIGS. 29A-29I and 30 each illustrate a representative surgical set up for the placement of a reference frame 300 on the femur 10 and the reference frame 400 along the tibia 15, in particular on or about the tibial tuberosity 18. Is to be appreciated that the illustrated OTT CAS procedure that follows utilizes the reference frames 300, 400—they are not moved but remain in the same position during all of the following OTT CAS process steps. An on tool tracking device 100 is coupled to a surgical tool 50 for the positioning and use of a tool 54 having an active element 56.

Figure 29A:
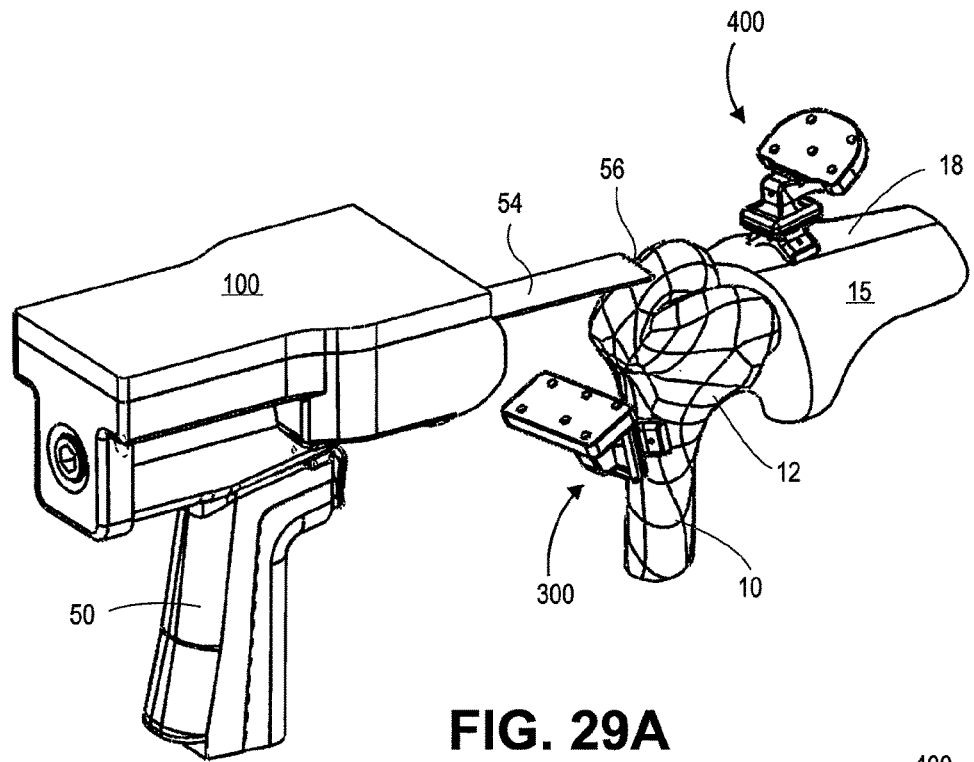
FIGS. 29A-29I and 30 illustrate the various views of an on tool tracking system and associated surgical tool in position for performance of a total knee replacement OTT CAS procedure.

In the illustrative embodiment of FIG. 29A, the OTT 100 is providing guidance for the use an active element 56 for making a distal lateral condoyle cut. During this cut, the cameras carried onboard OTT 100 are capturing, imaging, and providing relative navigation and positioning information based on information received from both reference frames 300 and 400 during all or a substantial portion of the illustrated cut.

Figure 29B:
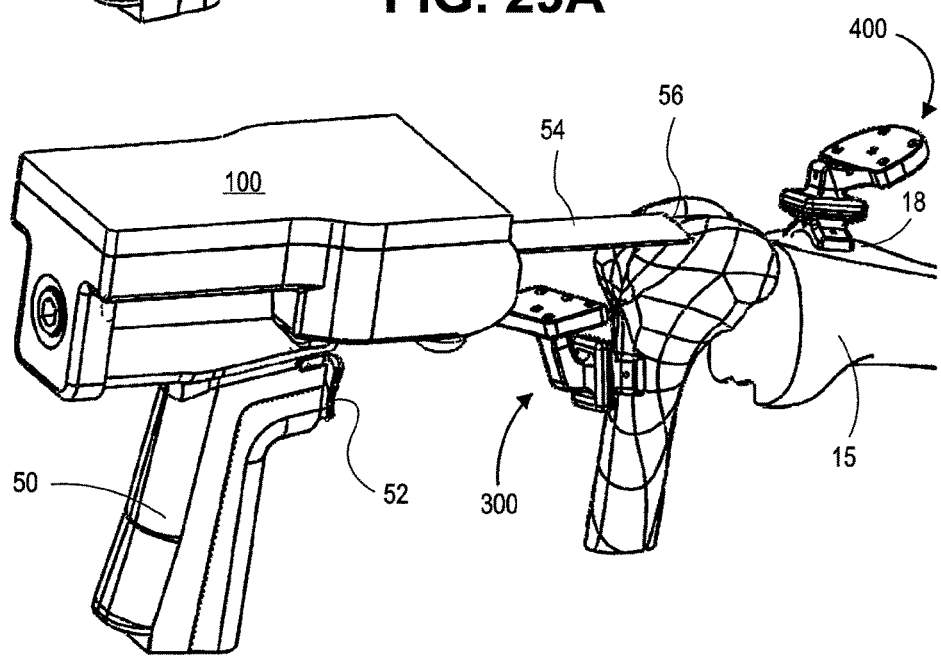

In the illustrative embodiment of FIG. 29B, the OTT 100 is providing guidance for the use an active element 56 for making a distal medial condoyle cut. During this cut, the cameras carried onboard OTT 100 are capturing, imaging, and providing relative navigation and positioning information based on information received from both reference frames 300 and 400 during all or a substantial portion of the illustrated cut.

Figure 29C:
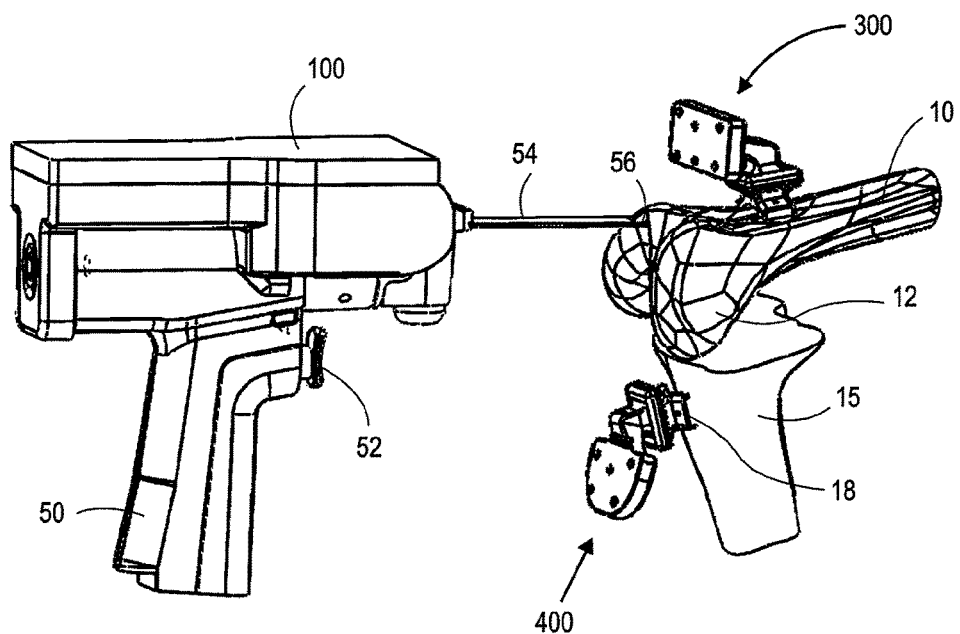

In the illustrative embodiment of FIG. 29C, the OTT 100 is providing guidance for the use an active element 56 for making an anterior cut. During this cut, the cameras carried onboard OTT 100 are capturing, imaging, and providing relative navigation and positioning information based on information received from both reference frames 300 and 400 during all or a substantial portion of the illustrated cut.

Figure 29D:
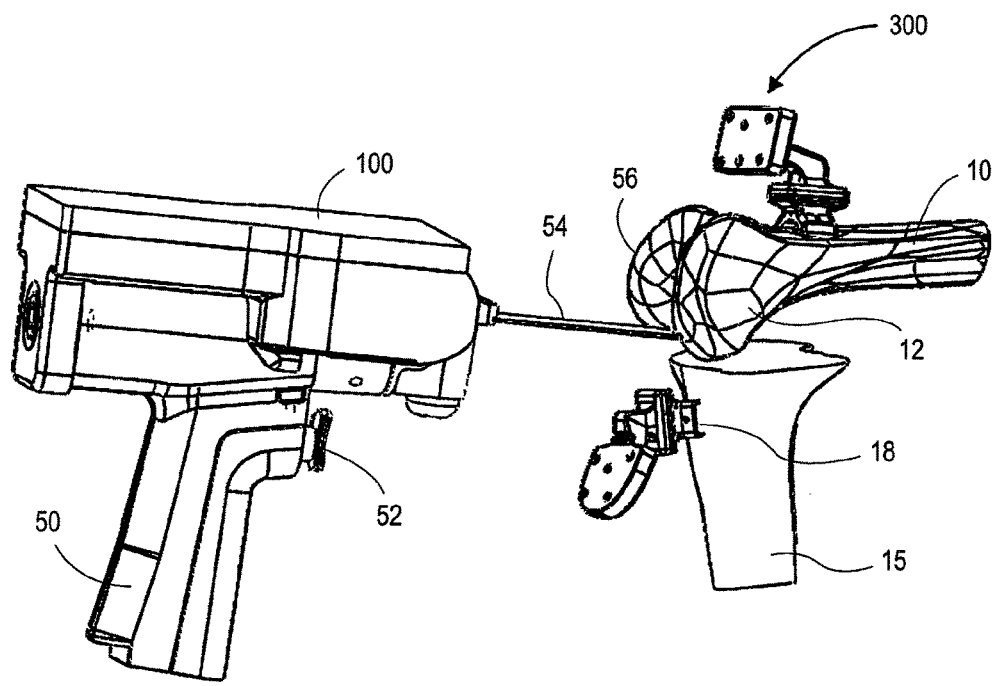

In the illustrative embodiment of FIG. 29D, the OTT 100 is providing guidance for the use an active element 56 for making a posterior lateral condoyle cut. During this cut, the cameras carried onboard OTT 100 are capturing, imaging, and providing relative navigation and positioning information based on information received from both reference frames 300 and 400 during all or a substantial portion of the illustrated cut.

Figure 29E:
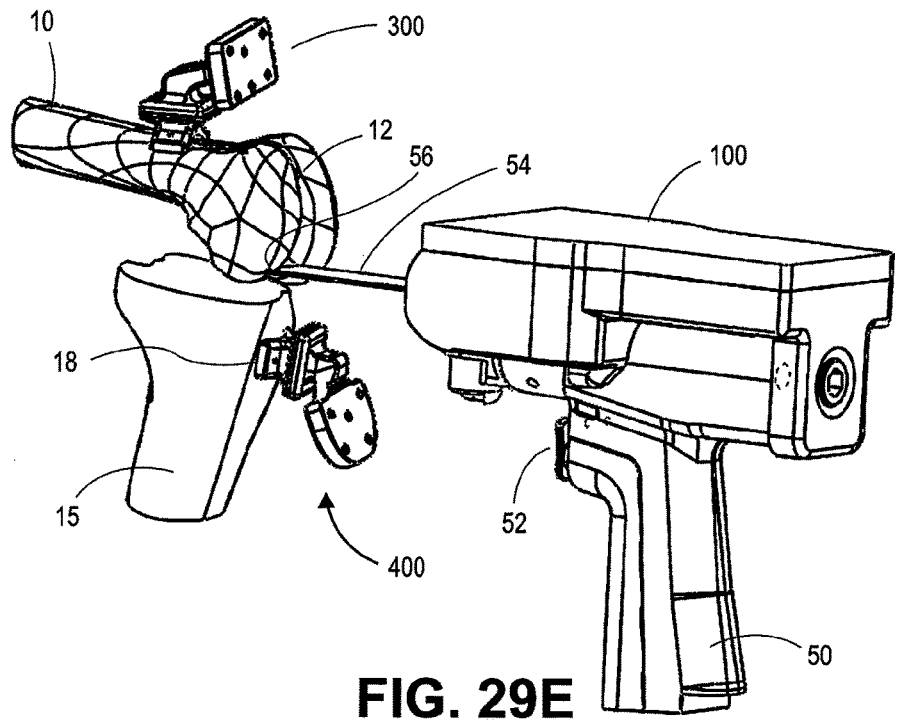

In the illustrative embodiment of FIG. 29E, the OTT 100 is providing guidance for the use an active element 56 for making a posterior medial condoyle cut. During this cut, the cameras carried onboard OTT 100 are capturing, imaging, and providing relative navigation and positioning information based on information received from both reference frames 300 and 400 during all or a substantial portion of the illustrated cut.

Figure 29F:
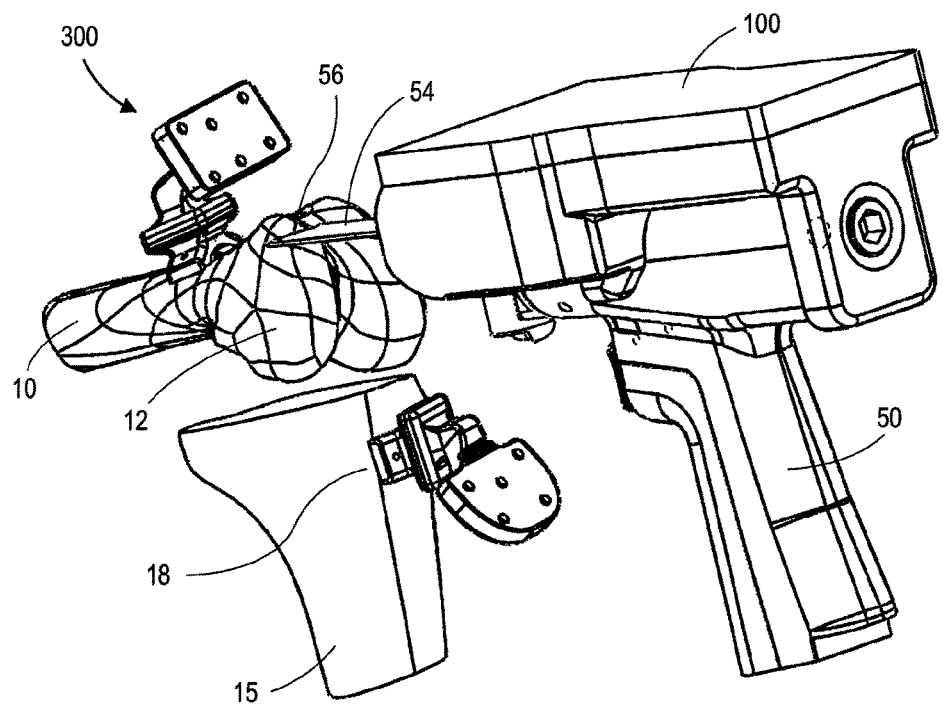

In the illustrative embodiment of FIG. 29F, the OTT 100 is providing guidance for the use an active element 56 for making an anterior chamfer cut. During this cut, the cameras carried onboard OTT 100 are capturing, imaging, and providing relative navigation and positioning information based on information received from both reference frames 300 and 400 during all or a substantial portion of the illustrated cut.

Figure 29G:
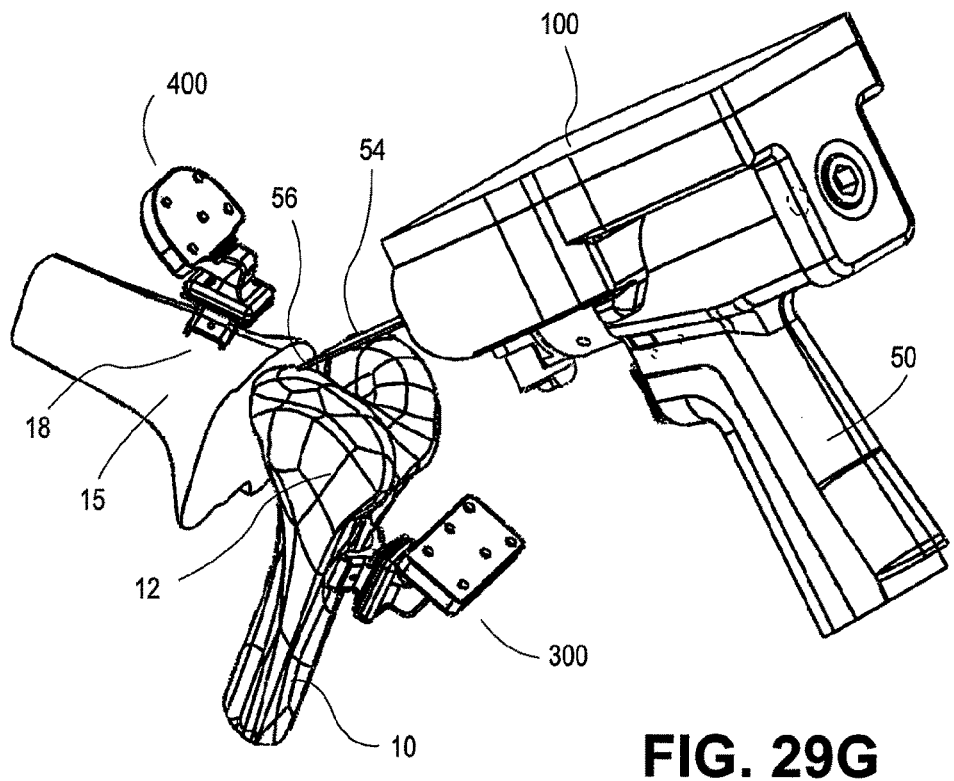

In the illustrative embodiment of FIG. 29G, the OTT 100 is providing guidance for the use an active element 56 making a posterior lateral condoyle chamfer cut. During this cut, the cameras carried onboard OTT 100 are capturing, imaging, and providing relative navigation and positioning information based on information received from both reference frames 300 and 400 during all or a substantial portion of the illustrated cut.

Figure 29H:
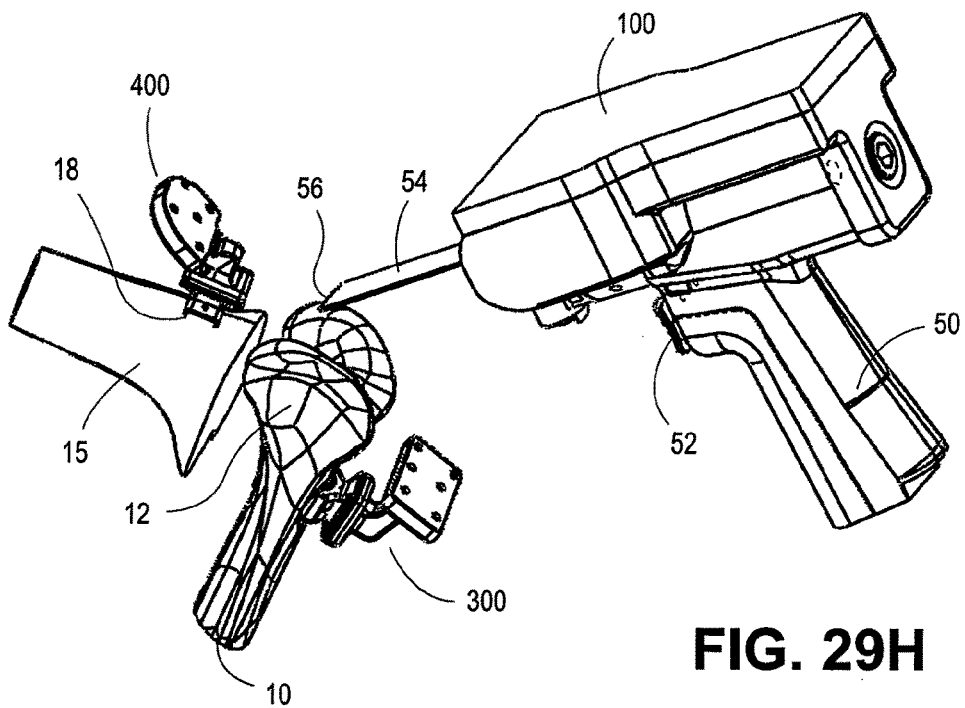

In the illustrative embodiment of FIG. 29H, the OTT 100 is providing guidance for the use an active element 56 making a posterior medial condoyle chamfer cut. During this cut, the cameras carried onboard OTT 100 are capturing, imaging, and providing relative navigation and positioning information based on information received from both reference frames 300 and 400 during all or a substantial portion of the illustrated cut.

Figure 29I:
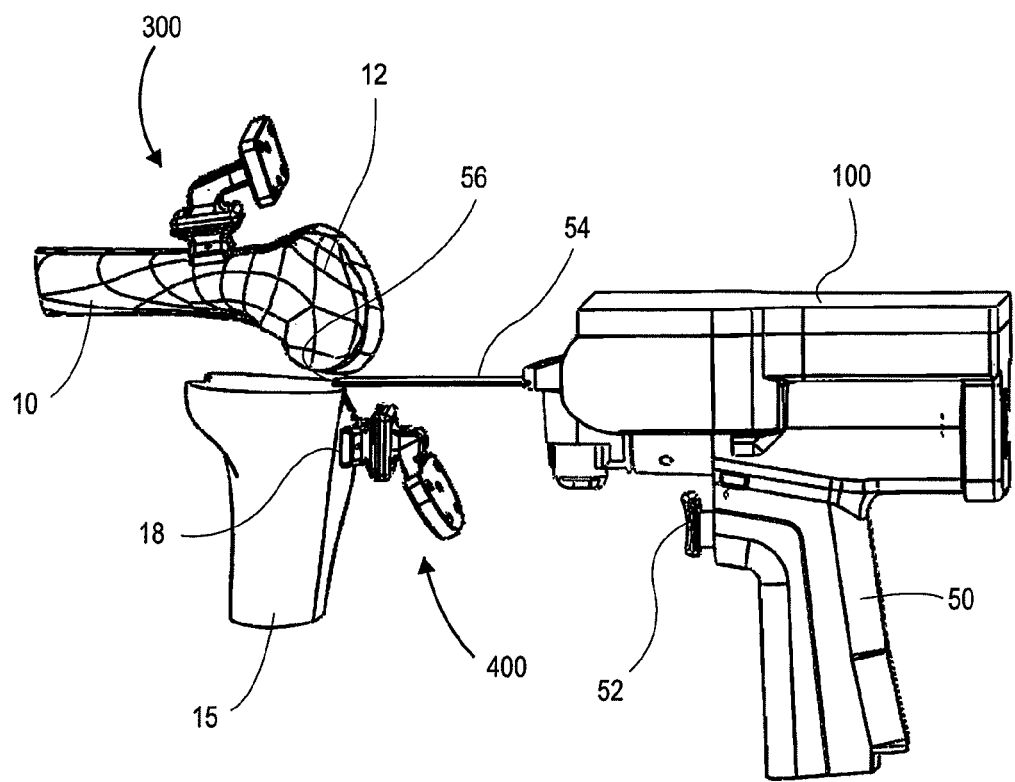

In the illustrative embodiment of FIG. 29I, the OTT 100 is providing guidance for the use an active element 56 making a tibial cut. During this cut, the cameras carried onboard OTT 100 are capturing, imaging, and providing relative navigation and positioning information based on information received from both reference frames 300 and 400 during all or a substantial portion of the illustrated cut.

Figure 30:
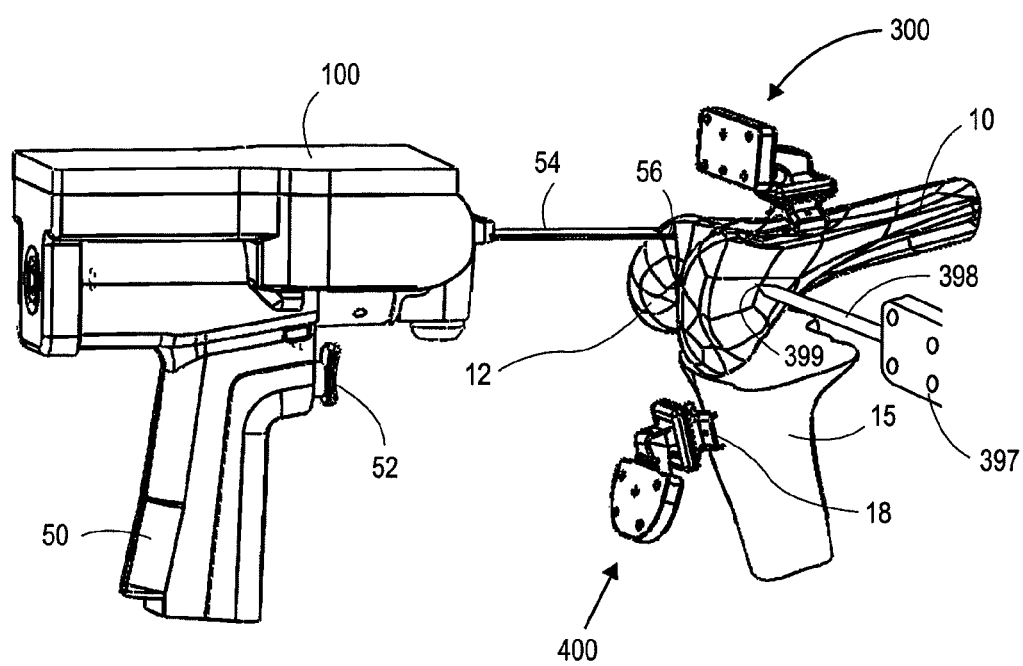

FIG. 30 illustrates an OTT 100 coupled to a surgical instrument 50 having a tool 54 and an active element 56. Reference frames 300, 400 are also shown in relation to a OTT CAS surgical site about the knee. An additional reference frame 397 having a stem 398 and tip 399 is being used for further registration or notation of the surgical field. The registration of the reference frame 397 is being provided by the imaging system of the OTT 100 with a tool. The registration frame 397 is being registered along with one or both of the registration frames 300, 400. While embodiments of the OTT CAS methods described herein by utilize both the reference frames 300, 400, it is to be appreciated that the, because of the improved image based tracking capabilities of the OTT and OTT CAS processing the OTT CAS system have both reference frames available but elect during processing to only use tracking information from one reference frame.

When considering the use of the unique reference frame embodiments described herein, consider the manner by which a view may be preferred by an OTT CAS system user. The OTT CAS system is pre-programmed so that certain views are shown by default for certain cuts. For instance, in the example of resecting a femur in preparation for a femoral prosthetic for a TKR procedure, several surfaces are to be cut, as shown in FIGS. 29 and 30. Each surface may be best viewed from a different perspective during the procedure. When cutting the anterior surface of the medial condyle a first view may be desirable, whereas when cutting the anterior surface of the lateral condyle a second view may be desirable. Accordingly, the system sets a pre-defined first view for viewing the virtual model when the anterior surface of a medial condyle is resected. Similarly, default visual views can be defined for a number of common resection procedures. When the OTT CAS system determines the cut to be performed, the system determines the best match for the cut and displays the default automatically without the intervention of the surgeon. In much the same way the vision based processes performed by the OTT CAS computer may be preselected to use all or a portion of the available tracking information from one or both reference frames, automatically, depending upon the circumstances. In addition, the OTT CAS may guide a user in adjusting orientation of a reference frame within a surgical field to improve guidance information from that frame. The adjustable orientation of the frame while maintaining the registration position of the base is described herein.

It is to be appreciated that any of a number and variety of powered or non-powered tools can be utilized with the OTT CAS systems described herein. For example, in the orthopaedic surgery field, the system can be built upon a single orthopedic power saw such as a Stryker System 6 Precision Oscilating saw. Similarly the system can be used with other power tools commonly used in orthopedic surgery, such as a burr or a drill. In such application, the system could be integrated within the design of the surgical tool, or added as a retrofit. In addition, the system could utilize a tool that does not require any external power source—such as a pointer, a marker or a scalpel. Ideally, the system could accommodate multiple smart tools to be used at different phases of a surgical procedure and make the system robust enough to perform a wide variety of surgical procedures.

The system could be used in other applications outside of orthopedic surgery. For example, it could be used in simulations and simulators for teaching and training surgeons for orthopedic surgery. Alternatively the system could be used for other medical procedures that require precise orientation and manipulation of rigid tissue. The present techniques computer assisted surgery could readily facilitate such dental procedures. The system can also be used in non-medical applications, for example in carpentry, sheet metal work and all other engineering marking and machining processes to guide the user to make a certain pattern of cutting or drilling of materials.

Embodiments of the OTT CAS system described herein eliminates the need for external tracking devices by placing one or more trackers on board the tool. The present invention can completely eliminate the need for an external tracking system or utilize the tracking sub-system to add new tracking data. In either configuration, the tool itself tracks the patient's anatomy, or tracks itself relative to a patient anatomy, as opposed to an external tracker that tracks both to determine the relative position of one to the other. Furthermore, because the components providing input to the tracking system are located on the tool itself, all tracked elements of the system are tracked relative to the tool. As a result, the tracking data produced by the on-tool trackers is very different. The position of the tool, for example, need not be independently tracked because all other tracked objects are tracked from the tool's vantage. The on board tracking system alleviates concerns faced by externally tracked systems, where all components of the system including the surgical instrument are tracked by an external device. Logistically, the present invention allows the operating room to eliminate or at least minimize the need for a separate piece of equipment in the operating room by placing the tracking or the components providing input to the processing part of the tracking system on the tool itself. With the sensors for the tracking on board the tool, this brings another advantage of being closer to the tracked target, and thus higher resolution and accuracy may result as well as less stringent requirements for "line of sight" access between the tracker and the tracked element of other systems.

The tracker-tracking subsystem further comprises one or more tracking elements that are detectable to the trackers on board the surgical instrument. There are a wide variety of tracking elements that can be utilized in the system. For example, reference frames that contain one or more reflective surfaces can reflect infrared or visible light back to the surgical tool. Light emitting diodes can similarly indicate the position of tracked objects back to the surgical tool. Other approaches, such as fiducial points or image recognition, could eliminate the need for external reference frames to be placed on the objects, such as the patient's tissue, that needs to be tracked. In further embodiments, the specific image of the patient's anatomy can serve as the tracking element without the aid of any other reference points.

The surgical instrument tracks the position of the tracked element by means of one or more trackers. In one embodiment, the system utilizes stereoscopic placement of two cameras as the tracker. The cameras are side by side, tilted at a range of angles suitable for stereo-vision, on either side of the saw's blade/drill-bit/burr, etc. For other tools, such as a drill, the cameras can similarly be placed stereoscopically, side by side, on either side of the drill bit or any other tool's end effector.

The placement of the cameras, relative to the end effector of the tool, impacts the operation of the tracker-tracking element subsystem. For example, placement of the camera or cameras far back from the end effector expands the field of view. For applications like joint replacement, or when the tool is in close proximity to the patient's anatomy, a wide field of view is helpful. With an expanded field of view, the tool can find the tracking element more easily. Placing the camera or cameras closer to the tool's end effector constricts the field of view, but adds magnification and resolution useful for applications such as dental surgery. In addition, placement of the camera must take into account the relative position of the other elements of the subsystem. Placing the cameras so their axes are in the plane of the end effector of the tool would minimize the extent to which the end effector blocks the view of the cameras. It is contemplated, however, that the cameras may be placed in any configuration that is deemed appropriate for tracking one or more tracking elements in a surgical procedure. As technology advances, configurations beyond those currently described may be more favorable in regards to particular tools and surgical environments.

The sub system can utilize a wide variety of cameras or systems of cameras. Generally, the system utilizes digital cameras. In addition, the system utilizes at least two cameras to provide stereoscopic vision. It is possible to use analog cameras, provided there was effective means of digital conversion such as the established technology of image format conversion which are sometimes known as 'frame grabbers' or 'capture cards'. Stereoscopic vision, and the ability to gain further information based on the differences in the images from the two cameras, helps the system to better locate the tracking element in three dimensions in terms of position and orientation or pose. Systems could utilize more than two cameras utilizing what is known as "redundancy" to improve the ability to navigate, such as in the cases when some of the tracked elements are not visible to one or more of the cameras and thus two cameras would not suffice in those instances. Additionally, a system could utilize a single camera but would need additional image processing to navigate as accurately as a stereoscopic system.

Alternatively, the subsystem could utilize a different system of trackers and tracking elements. In one alternative, the tracker is a high-resolution camera optimized for image recognition under the visible light spectrum present in standard Operating Room conditions. The tracking element is the patient's anatomy, based on the medical image stored in the surgical plan. In addition, a narrower field of view may also benefit the efficient recognition of the patient's anatomy. Finally, the surgical plan itself may need to incorporate or identify particular anatomical landmarks of the patient to establish functional tracking elements.

Regardless of configuration, the cameras need to have sufficient resolution to accurately track the tracking element to a certain predetermined level of accuracy. For example, a system with a tracking element that is a reference frame with infrared LED's, cameras with 640×480 resolution have sufficient resolution to track the tracking element with surgical accuracy. Systems can utilize additional elements, such as infrared filters, and isolate the tracking element for the cameras. A lower resolution camera, in such a system, can be sufficient to produce highly accurate tracking.

Resolution is not the only characteristic of the cameras that influences the operation of the system. The frame rate is an important consideration, depending upon the particular configuration of the system. For example, a very high frame rate of around 100 Hz (frames per second) would produce minimal latency but would be very burdensome on the image processor. The system would require a powerful processor in order to extract the tracking element from so many captured images in a given unit of time. Alternatively, if frame rate is too low then the system will produce too much latency. If the operator were to move the tool too quickly then the system would not be able to continuously track the tool. The minimally acceptable frame rate should be utilized in the system. For a system that utilizes infrared LED's in the reference frame along with an array of VGA cameras, a frame rate of 30 Hz would produce a system suited to freehand orthopedic surgery.

Together, these examples illustrate a variety of configurations for the tracking element and the cameras that comprise the exemplary camera-tracking embodiments of the tracker-tracking element subsystem. In addition to the accurate placement of the tracking element, the tracking element's location must be extracted from the images captured by the camera. An image signal received from the cameras must undergo digital signal processing (DSP) to convert the image of the tracking element to mathematical coordinates, relative to the tool. The mathematical coordinates are then sent to a computer system and compared against the surgical plan, allowing the computer system to determine if the surgical path is following the intended resection.

Consider that there are several steps to process the raw data from the cameras into the mathematical coordinates. Initially, the system must acquire the image. For the camera detecting the markers (e.g. infrared LED's, reflecting bodies, fiducials, etc.), the system must: determine the coordinates of the centroid of each of each individual marker used in the overall tracking element, determine the sizes of each element, and report the size and shape and the coordinates of each LED to the computer system. Additional operations to process the captured image, such as sub-pixel analysis to determine the location of the centroid can improve accuracy.

For systems that operate at 30 Hz, steps must be completed in approximately 33 ms, and the computer will need to determine the relationship between the individual LED's and calculate the position and orientation of the tracking element. From that data, the computer will have to determine the orientation of the model and the relative positions between the bone and the surgical tool. The signal processing only has the amount of time between two successive frames to perform any needed operations. (For example, for a frame rate of 30 Hz, the processing system has the above mentioned 33 ms period to perform these operations) In one embodiment, the majority of the forgoing steps can be accomplished on the tool itself often by integrated CPU's on the cameras (or other trackers) themselves.

For example, additional processing of images captured by the cameras can be accomplished via a CPU that is integrated into the camera, or on the computer system or some combination of the two. For example, many small cameras have integrated CPU's capable of running digital signal processing algorithms prior to exporting the data signal. The DSP can comprise a simple step, like converting color images to grayscale or complex operations, like cropping the video image to a small box that surrounds the identified LED's. The initial processing makes the final extraction of the tracking element from the images captured on the camera less computationally burdensome and the overall tracking process more efficient.

The camera-tracking element subsystem can either utilize digital cameras with digital image transmission, or with wireless transmission. There is a wide variety of cameras with digital image transmission which are generally termed "IP" or "Wifi" cameras. Many small, low cost solutions can be used, streaming images (which can be synchronized between two cameras) in any format (e.g. Mpeg) and fed to the processing electronics through one of many known digital streaming protocols. Alternatively, analogue Image transmission can used as has been in model airplanes with what is known as First Person View (FPV) technology. This facilitates readily available commodity cameras, with minimal weight and size, small wireless transmission and low cost. After image processing and extraction of the coordinates for the tracked elements, additional processing is necessary to create tracking data sufficient to inform the computer system. The coordinates of the tracked elements are combined with information about the cameras (such as the specifications and calibration data) to further refine the location space of each tracked element. Based on the refined location of each tracked element, the sub system utilizes user-defined definition of clusters for the particular tracking element (sometimes called a reference frame) to detect valid clusters for the tracking element and their position and orientation in space. The data determining position and orientation in space is the formatted for use. For example, the system can place the special coordinates into a matrix that is compatible with the overall definition of the space used in a surgical plan.

The forgoing processing is different from the processing that can occur on the tool and is not image conditioning and spatial extraction. It can be processed through dedicated software that could be in the same computer system where the surgical plan and planned resection is computed or it could happen on an intermediary computer that could be on the tool or separate from both the tool and the computer system.

Additional navigation data can augment the camera-tracking element system. The tool can further contain one or more accelerometers or inertia sensors to determine the orientation and movement of the tool along the surgical path. The accelerometers can provide additional data to the computer system, in addition to the tracking data from the camera or cameras. Alternatively, an external tracking system can augment the on-board tracking of the tool. No such application is required but can serve to augment the tracking capability of the system mainly by 'anticipating' the movement of the user. Systems could further include multiple tracker-tracking element modalities. For example, the system could include an infrared camera and a tracking element with an infrared LED as well as a visible light camera for optical resolution. Tracking information from both could be processed to establish the coordinates of the tool in three dimensions.

As is typical in computer aided surgery, a surgical plan is determined before commencing the desired surgical procedure or prior to performing a step in the desired surgical procedure. The surgical plan is based on intended resections designated by the surgeon on a computer rendition of a patient's anatomy. A computer rendition of a patient's anatomy may be procured through a variety of medical imaging techniques, such as CT or MRI scanning. In addition, a computer rendition of a saw, drill, burr, implant, or any surgical instrument or part thereof may be procured by design specifications (or models) programmed into the computer system. Once a computer rendition of patient's anatomy is accessible through a computer interface such as a display, mouse, keyboard, touch display, or any other device for interfacing with a computer system, the surgeon may manually designate resections for the surgical plan by entering one or more cuts to be performed, a region to be drilled, or a volume of tissue to be removed into the computer system. Alternatively the computer system may be configured to generate the surgical plan based on a set of specified parameters selected by the surgeon. The specified parameters may correspond, for instance, to the shape, size, and/or location of an implant that the surgeon wishes to attach to the patient's anatomy. The computer may accordingly generate a surgical plan comprising the resections necessary to fit the implant to the patient's anatomy. Once the surgical plan is designated by the surgeon, the computer system translates the surgical plan into one or more mathematically defined surfaces defining the boundaries of the intended resections that comprise the surgical plan. Data acquired by the previously described tracker-tracking element subsystem can then be used to compare the instrument's surgical path with the surgical plan in order to determine the deviation of the surgical path.

Next, the surgical plan is delineated as one or more surfaces mathematically defined in an acceptable three dimensional coordinate system such as Cartesian, spherical, or cylindrical coordinates, or other anatomically based coordinate systems. For example, in a surgical plan that uses Cartesian coordinates, a cut may be defined as a specified distance along each of the X, Y, and Z axes from an XYZ coordinate defining the origin. The specified distances along each axis need not be linear. For example, a cylinder representing a region to be drilled in the patient's anatomy may be defined in Cartesian coordinates as a circular surface having a specified diameter located around an origin and protruding for a specified distance from the origin in a direction that is perpendicular to the circular surface. Any cut, series of cuts, or volume of tissue to be removed may be mathematically defined through a similar approach of defining surfaces that delineate the boundaries of the surgical plan that the surgical instrument must follow to complete the designated resections.

As previously noted, the surgeon may manually designate the resections of the surgical plan on a computer rendition of the patient's anatomy. In one embodiment the surgeon can use the computer interface to view and manipulate a three dimensional rendition of the patient's anatomy and make marks representing cuts. The marks made on the three dimensional rendition are then translated into the mathematical surfaces delineating the surgical plan that the surgeon must follow with the surgical instrument.

In surgical procedures utilizing implants such as a total knee replacement surgery, it is advantageous to use the physical specifications of the implant when delineating the surgical plan for better assurance that the implant will fit onto the patient's anatomy correctly. In such an embodiment, the surgeon can use the computer interface to view and manipulate a three dimensional rendition of the patient's anatomy as well as one or more specified implants. For example, the surgeon may be able to choose from a catalog of implants having different physical characteristics such as size, shape, etc. The surgeon may choose the appropriate implant and manipulate the three dimensional rendition of the implant to fit over the three dimensional rendition of the patient's anatomy in the desired alignment. The surgeon can then select an option for the computer system to generate the surgical plan comprising the planned resections required to prepare the patient's anatomy to receive the implant. Accordingly, the computer system may be configured to generate the appropriate mathematical surfaces to delineate the surgical plan by calculating the surfaces at each intersection between the computer renditions of the implant and the patient's anatomy as they have been aligned by the surgeon.

In order to guide the surgeon to follow the surgical plan with the surgical instrument there must be a means for comparing the path of the surgical instrument with the planned resection. The tracker-tracking element subsystem may accordingly track the three dimensional location and orientation of the mathematically defined surfaces of the surgical plan relative to the tool. In one embodiment, the mathematical surfaces are referenced by the tracking element located at a fixed position on the patient's anatomy. For better accuracy the tracking element may be fixed to rigid tissue at an easily identifiable location. Doing so will simplify registration of the patient's anatomy with the tracking system and will avoid unwanted error that may be caused by unpredictable movement of soft tissue. Once the patient's anatomy is registered with the tracking system, the mathematical surfaces defined in the computer system can be tracked based on their coordinates relative to coordinates of the tracking element's fixed position. Since the tracking system is located on the surgical instrument, tracking data collected by the tracking system regarding the location and orientation of the patient's anatomy and the corresponding mathematical surfaces of the surgical plan are relative to a defined reference point on the surgical instrument. Accordingly, during the surgery, the computer system may use the tracking data to make iterative calculations of the deviation between the surgical path followed by the surgical instrument and the surfaces of the surgical plan. Errors in alignment between the surgical path and the surgical plan as well as corrective actions may be communicated to the surgeon by an indicator such as a graphical notification on a computer screen, LCD, or projected display, a flashing light, an audible alarm, a tactile feedback mechanism, or any other means for indicating deviation error.

In one aspect, an indicator is a system to provide guidance to the surgeon on how to align the surgical path to achieve the intended resection of the surgical plan. In one embodiment, the indicator is an element of the computer system used to provide information to the surgeon in the operating room. U.S. patent application Ser. No. 11/927,429, at paragraph [0212] teaches the use of an operating room computer to guide the surgeons operation of a surgical tool. One means of indication taught in the '429 patent is the actuation of the surgical instrument. As the surgeon's surgical path deviates from the intended resection, as detected by the on-board camera-tracking element subsystem, the computer system will communicate with the surgical tool to slow or even stop the tool from operating. In such a system, the actuation of the surgical tool is the means by which the surgeon receives indication from the computer assisted surgery system as further taught in the '429 application at paragraph [0123].

In another embodiment, the computer system could indicate when the surgical path deviates from the intended resection via an external display. The computer system can display a three dimensional rendition of the surgical tool and the patient's anatomy. Overlaid onto that image is a three dimensional rendition of the surgical plan. The computer system updates the relative position of the surgical tool and the patient's anatomy, as determined by the camera-tracking element sub system, and overlays the intended resections. The surgeon can then utilize the display to align the surgical path with the intended resection. Similarly, the relative position of the surgical tool and the patient's anatomy can be displayed on other screens, such as a personal eyeware display, a large projected display in the operating room, a smartphone or a screen attached to the tool. The combination of an external screen, such as the one on the computer system, and other screens, such as a screen on the tool itself, may provide the surgeon with an optimal amount of information. For example, the screen on the computer system can provide the surgeon with a global overview of the procedure whereas the screen on the tool can provide particular guidance for a specific resection or step in the procedure.

A screen on board the surgical tool is taught in the '429 application at paragraph [0215]. The on board screen could display the same kind of image as described above on external display. An exemplary implantation in the context of an OTT device is shown and described in FIGS. 52A and 52B. The on board screen could display a simplified depiction of the alignment of the surgical path and the intended resection. In one embodiment, the simplified display is comprised of three lines. The surgical path is depicted by two lines, one small and one large. The small line depicts the distal end of the surgical path while the wider line depicts the proximal end of the surgical path. The third line depicts the intended resection. The first two lines are calculated from the navigated position (location and orientation) of the surgical tool. The computer system compiles all three to display on the screen on the surgical tool. The display shows both the proximal and distal parts of the surgical path, indicating to the surgeon its relative position in three dimensions. When the surgical path is aligned with the intended resection, all three lines are aligned. The indicator shows the surgeon how to correct the position of the tool in three dimensions.

In one embodiment, the display is optimized to provide guidance for navigating a saw. The surgical path is depicted by lines, which roughly correspond to the shape of the cut that a saw makes. In another embodiment, the simplified depiction could be depicted by two circles: a small circle depicting the distal end of the surgical path and the larger depicting the proximal end. A second shape that is roughly equivalent in size, such as a cross or diamond, depicts the intended resection. As previously described, the surgeon can align the surgical path to the intended resection by lining up the shapes. The circles depict the surgical path of a different tool, like a drill. In this manner, the system can provide guidance for a wide variety of surgical tools. In one embodiment, the position of all of the elements described in the indicator should be updated, by the computer and tracking sub systems, at a rate that is faster than human reaction time.

One limitation of surgical displays is that they divert the surgeon's attention away from the patient. One solution is to project the indication information directly onto the part of the patient's body where the procedure is taking place. Any variety of projectors could be placed onto the tool and display any of the indication methods onto the patient. In one embodiment, an on board Pico projector could display the three line simplified approach described above. In many respects, the third line would be enormously helpful as it would depict, precisely onto the patient, where the intended resection would start relative to the rest of the patient's anatomy. In addition, the indicator can provide more direct guidance as to how to correct the surgical path for alignment with the intended resection and project the guidance information directly onto the patient. For example, the projector can depict an arrow that points in the direction the surgeon needs to move to correct the surgical path.

There are several challenges to accurately project the indication information onto the patient anatomy. Foremost, for an onboard, on-the-tool approach, the projection platform would be constantly in motion. In addition, the surface that the projector is projecting on is not flat. To resolve the second question the system utilizes information obtained during the surgical planning. First, the system knows the geometry of the surface of the patient's anatomy. The surgical plan contains a medical image of the patient, such as a CT scan, from which it can extract the geometry of the surface that the indicator will project on. The system accordingly projects guidance information so that it is properly seen by the surgeon viewing the projected information on the surface of the patient's anatomy For example, if the system is to indicate where the surgeon should cut with a saw, by utilizing a straight line, then the system can bend and curve the line so that, when projected onto the patient's anatomy, it will appear to be straight. Utilizing that approach, the indicator can project the three line simplified depiction of alignment taught above.

Similarly, the system also calculates the relative position of the tool by means of the tracking system. With that information, the system can continuously modify the angle of projection to ensure that the indicator projects to the proper position of the intended resection on the patient's anatomy. The indicator can use a wide variety of projectors such as a mini standard-LED projector or a laser-scanning pico projector system. Notwithstanding, nothing in the forgoing prevents the utilization of a projector that is not on board the tool or used in any other form of computer-assisted surgery. For example, an externally tracked system could include a separate projection system that would similarly project indication information onto the patient's anatomy.

In addition to a screen or a projector on board the saw, the system can utilize a smartphone or tablet computer, such as an Apple IPhone 4G, to provide indication to the surgeon.

An indicator that uses a smartphone or tablet computer has the further advantage of a removable screen. Additionally, just as the on board screen, the smartphone can display renditions of both the tool and the patient or a simplified image, such as the two line embodiment. A different simplified display could provide indication when the surgical path and the intended resection are aligned and direction when they are misaligned. For example, if the surgeon is approaching the resection too low, then the screen can depict an arrow pointing up. The arrow can be rendered in three dimensions, providing further indication to the surgeon.

For simplified indicators, the display need not be as robust as a smartphone or other high-resolution screen. A bank of LED's, for example, could display either the three line or arrow indication previously described. The Indication method need not be visual. The system could audibly indicate to the user when the surgical path deviates from the intended resection, as further described in the '429 application at paragraph [0122].

As detailed above, computer assisted surgery proceeds from a computer-based anatomical model such as those based on images and reconstruction obtained using any known medical imaging modality, or from anatomical models generated through morphing or other known processes for rendering anatomical or bone models for use in computer aided surgery with the aid of computer-based anatomical models, a surgical plan is developed to be implemented for a specific patient and procedure. Surgical preplanning includes a number of steps such as obtaining pre-surgery image data, surgical planning for the specific procedure to be undertaken, adaptations of the plan for patient specific anatomy or condition and, if appropriate, to any specific prosthesis, devices, implants, or other structures to be placed in, joined to or used at a chosen 3D alignment during the CAS procedure. With this general pre-surgical planning information in hand the surgeon moves to the patient specific intraoperative planning to be implemented at the surgical site. The patient specific intraoperative surgical plan will be adapted to address the specific site or specific procedure such as any orthopedic procedure or minimally invasive procedure that may be enhanced through the use of computer assisted surgery. For example a specific joint may be aligned for some form of repair, for partial replacement or for full replacement. It is to be appreciated that the techniques described herein may be applied to other joints such as the ankle, hip, elbow, shoulder or for other portions of the skeletal anatomy (e.g. osteotomies or spine surgery procedures) that would benefit from the improvements to computer aided surgery described herein. Examples of skeletal anatomy that may benefit from these techniques include, without limitation, vertebrae of the spine, the shoulder girdle, bones in the arm, bones in the leg, and bones in the feet or hands.

By way of a non-limiting example a total knee arthroplasty will be used as a specific example. For purposes of discussion the total knee arthroplasty will normally include five surgical cuts for the femur (on a CR or PCL retaining and eight cuts on a PS or PCL sacrificing) and one or more cuts for the tibia each of them described below in greater detail. It is to be appreciated that these cuts may be modified to emphasize a particular aspect or aspects of a portion of a surgical procedure or step. For example, the specific geometry, orientation, or feature of a prosthetic device for a particular procedure may lead to modifications in certain aspects of the surgical plan. In another example, a particular procedure or prosthesis may benefit from a specific type of cut, tool, or surgical approach. Any of these factors may also be used to adjust the way that the computer aided surgery proceeds according to the embodiments described herein. By way of a non-limiting example, the computer aided surgery system may select the surface (e.g. plane) of cut as the most important information to be presented to the surgeon immediately prior to or during a computer aided surgery step. In still further aspect, and OTT CAS will permit the user to select or base surgical step decisions using 2-D, 3-D or other output information related to a representation of either the surgical tool being used or the resulting use of that tool on the anatomy. For example, if the surgical tool is a saw then the user may select from rectangular shapes generally sized to correspond to the profile of the saw, or to one or more surfaces (in this specific example a plane) that correspond to the resulting cuts formed in the anatomy by the saw. In an additional example, the surgical tool includes a drill and the user is provided with or the system basis processing decisions using circles corresponding to the size of the drill, cylinders related to the anatomical impact of the use of the drill, as well as other factors that might represent the engagement of the drill cutting tip to the anatomy. In still another example, the surgical tool includes a reamer or other spherically shaped tool. In this example, the system or the user is provided with circular, cylindrical, hemispherical, or spherical representations that are likewise used for display and feedback to the user or as part of processing decisions used within the OTT CAS system. In a final example, the surgical tool includes a flat filing blade, whereby the representation will again be a flat surface (or thin rectangular block) depicting a certain thickness of filing action which would result upon contact to the anatomical surface.

In the embodiments that follow, an on-tool tracking system (OTT) embodiment is used to acquire, perform some data-processing on board, and provide real-time data regarding the surgical procedure to the computer-aided surgery computer, and to receive commands from the latter to set its own motor speed, attenuate speed or even stop to prevent unintended cutting. The on tool tracking system is used to provide a variety of data for use by the computer aided surgery system. One form of data is imaging data from imaging sensors provided by the on-tool tracker. The data provided by these imaging sensors include for example stereoscopic images, which once processed, can be used for tracking and information to be projected onto the surgical field by a standalone or an embodied projector or any type of projector provided for use with the on tool tracking system. Other data provided by the imaging sensors includes, reference frame location, orientation, alignment or other physical attribute of a reference frame used for defining the surgical field. One or more reference frames that may be positioned around the field, around the joint, around the knee, or sized and shaped in relation to a surgical field where the reference frame is visible during at least a portion of all or substantially steps of a surgical procedure. (See, for example, reference frame embodiments described with regard to FIGS. 16-30. Still further, data may be selected only from a relevant reference frame or portion thereof based upon the dynamic, real time assessment of a CAS procedure or CAS step.

For example, in a CAS procedure where two frames are present, both may be used at the beginning of a cut and then the system shifts to using only one reference frame used during the cut. In a similar way, the system may use less than all the fiducial markers available on a specific reference frame during a procedure in furtherance of the mode adjustments described below. Fewer fiducials to process may permit faster updates or reduced image processing computer cycle time. As shown and described herein, the reference frames may have the same shape or different shapes and may contain any of a variety of fiducial markers in any of a variety of suitable arrangement for detection by a visual or an infrared tracking system in the OTT. Still further data available from the imaging sensors includes scene information such as anatomical configurations of real or artificial anatomy or structures, markers positioned on the patient, additional targets positioned around the surgical field such as pointers, markers or the instrument being used in the field such as a saw, drill, burr, file, scene information refers to image capture, image processing or camera adjustments to select and process a portion of a frame, adjust a camera to zero in on or focus or zoom to a portion of interest in the surgical field based on real-time dynamic CAS procedures and consideration of a CAS surgical plan, reamer or any other surgical tool to which the on tool tracking system is mounted.

When resecting the various portions it may be desirable to modify the view of the virtual model displayed on the OTT monitor. For instance, when cutting along a first plane it may be desirable to view the virtual model from a first perspective, and when cutting along a second plane it may be desirable to view the virtual model from a second perspective. Accordingly, the OTT CAS system tracks various data regarding the status of a procedure, including, but not limited to the following: the position of the surgical tool relative to the tissue to be resected and the orientation of the surgical tool relative to the tissue to be resected. Based on the position and orientation of both the tissue and the surgical tool, the system calculates which surface is about to be cut during the procedure and update the OTT monitor accordingly.

Further, the OTT CAS system can be configured to account for the preference of each user as well as the characteristics of the instrument using the OTT device. Specifically, a surgeon may desire a different view than the default view for a particular resection step or cutting plane. The system allows the surgeon to override the default selection and specify the view for a particular cut. The system stores the information regarding the desired view for the particular cut for the particular surgeon and uses the view as the default view in the future when the system determines that a similar cut is to be made. The system tracks the user preference based on the user logged into the OTT CAS system.

In addition to the types of data described above, the on tool tracking system may also provide other kinds of data such as output from one or more sensors on the on tool tracker. Exemplary sensors include position sensors, inclinometers, accelerometers, vibration sensors and other sensors that may be useful for monitoring, determining or compensating for movements of the tool that is carrying the on tool tracking system. For example, there may be sensors provided within the on tool tracking system to compensate for noises or vibrations generated by the tool so that the noise and vibration may be compensated for i.e. cancel out of the imaging data or other OTT data being transmitted to the computer aided surgery system computer. In still another example, an accelerometer or motion sensor may be provided to produce an output to the computer aided surgery system used in predicting the next frame or estimating where relevant information in an imaging frame may be located based on the movement of the tool and a tracking system. In still another aspect, sensors carried on board the on tool tracking system may be used to detect, measure and aid in canceling unwanted movement that may interfere with, impair the quality of or complicate CAS or OTT image processing. Specific examples of this type of feedback include sensors to detect and aid in the cancellation of hand shaking or movement by the user. In still another example sensors may be provided to detect and aid in the cancellation or compensation of unwanted movements or other interference generated during active surgical steps.

In other variations, image capture, processing and camera adjustment may also be used in or become the subject of compensation techniques, including to dynamically optimize the field-of-view and volume-of-interest. In one example, a camera provided on the OTT contains an auto focus capability that, under instructions from the CAS computer and the various factors described herein, will dynamically adjust the camera and view to zoom, track, pan or focus on a frame, a portion of a frame or a natural or artificial feature. In another aspect, the imaging portion of a camera on the OTT is provided with a suitable on board movement system to tilt or adjust the lens to direct the lens to one or more features under the direction of the CAS computer. This tilting lens may be used in conjunction with the dynamic lens above or with a lens having fixed (i.e., not adjustable characteristics). In one aspect, a micro mechanical base supporting the camera lens is adjusted according to the instructions from the CAS computer. It is to be appreciated that while the lens/camera adjustment may be done internally with a MEMS structure, it may be done external to as well. For example, a camera in a housing may be carried by a dynamic stage (x-y-z or x-y motion for example) where the state receiver instructions from the CAS computer to adjust the camera position in accord with the OTT CAS processes described herein. Still another form of compensation provides for image processing or other adjustments for OTT-tool orientation such as top mounted OTT, left side mounted OTT or right side mounted OTT. Still further, the various aspects described above for controlling the field of view (including either or both of the horizontal and vertical field of view alone or in any combination) along with adjustments to a volume of interest within the surgical field may be accomplished dynamically and optimized in real time utilizing the instructions contained within the OTT CAS system, the CAS mode select processing sequences and/or any of the specific CAS mode algorithms including vision based algorithms or specific mode algorithms.

Another example of settings and compensation techniques include the implementation and switching on/off of infrared filters placed in front of the camera lens so that the imaging can be of infrared only or emitted or reflected by the reference frame markers to cut-out white light noise and to ease image processing and marker detection.

It is to be appreciated that these aspects of compensation may be implemented mechanical components, electrical components or with software, each alone or in any combination.

For purposes of discussion and not limitation the data from the on tool tracking system will be categorized as imaging data and sensor data to capture the broad categories described above. Using system resources provided either on the on tool tracking system itself or provided by the computer-aided surgery computer, the data is processed to provide an output for use by the computer aided surgery system. The desired output of data processing comes in a number of different forms depending upon the specific processes being evaluated and as described in greater detail below. For purposes of this overview, one may consider that the data output obtained from the on tool tracking system may include such things as the orientation of the on tool trackers in the surgical field, the position of the tools or the on tool trackers in relation to the surgical field, information regarding the surgical field such as physical changes to the anatomy undergoing surgery, movement of the OTT tracked tool within the surgical field, displacement of the tool within the surgical field, apparent progress of the surgical step being tracked and other information related to the initiation, progress or completion of a surgical step or a computer aided surgical procedure.

The output of the on tool tracker, in whatever form suited to the particular computer aided surgical procedure undertaken, is next compared to the step, or procedure undertaken according to the surgical plan. The result of this comparison produces an output back to the on tool tracker that gives information related to the plan, step, or progress with in a step of the surgical plan. In general, this output is manifested for the user as the result of a projected image from a projector on board the on tool tracker, but it can also include audio feedback, changes/messages in a computer screen if available, actions on the cutting tools (e.g. changes of cutting speed, direction and stopping), etc. It is to be appreciated that the output from this projector (as example) may be adapted based on a number of considerations such as the available surgical field upon which an image may be projected, the likely position and orientation of the on tool tracker and its tool to the surgical field, and the likely challenges of making the projected image visible to the user. As a result, the onboard projector is capable of projecting images in a variety of configurations based upon the dynamic, real-time circumstances presented during the surgical procedure. Moreover, the on tool tracking system may be provided with additional illumination sources to enable the system or the user to obtain image data in the visible spectrum, infrared spectrum, or in any other spectrum suited to image processing using the on tool tracking system. In still further aspects, one or more of the CAS mode processing methods described herein may be modified to incorporate the use of any of a variety of pattern recognition, computer vision, or other computer-based tracking algorithms in order to track the location and orientation of the OTT instrument in space relative to the surgical site, or relative to other instruments near the surgical site, and progress of an OTT CAS surgical step, without or substantially without the use of reference frame-based tracking information. In other words, the embodiments of an OTT CAS method include the use of visual information obtained from the trackers or cameras on board the OTT for the purpose of identifying, assessing, tracking, and otherwise providing the CAS data sufficient for the purposes of providing appropriate CAS outputs for the user to complete one or more CAS processing steps. In one aspect, a portion of the anatomy within the surgical field is marked or painted for the purpose of enhancing vision based tracking and vision based algorithm processes. As a result of being provided information from the projector of the on board tracking system, the user may respond to that information by making no change to his actions or by adjusting, as warranted under the circumstances for the step or procedure, one or more of the operation, placement, orientation, speed, or position of the tool in the surgical field. The information from the projector may be provided alone or in combination with other OTT components or feedback or indications such as tactile or haptic feedback.

Next, the continued action or change of action by the user is detected by the on tool tracking system and the process of providing data processing data and providing it for comparison and evaluation by the computer aided surgical system continues.

Against this general overview is to be appreciated how, in use, embodiments of the on tool tracking enabled computer aided surgery system described in herein monitors and evaluates one or more of the position, movement, use, predicted movement of an instrument using the on tool tracker against the planned computer aided surgery procedure and produces appropriate computer aided surgery outputs to the user based at least in part on a real-time computer aided surgery assessment by the computer aided surgery system.

Figure 31A:
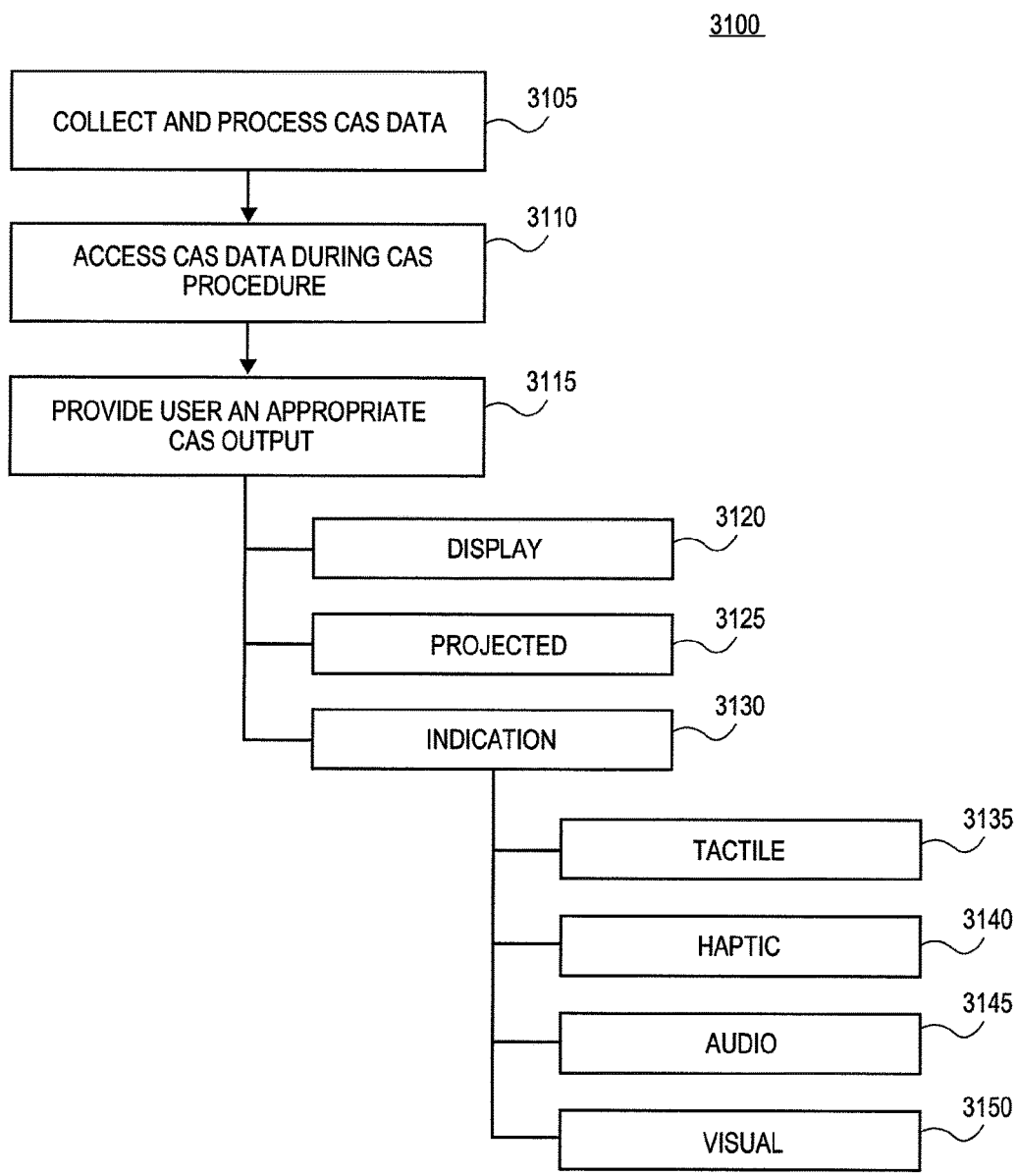
FIG. 31A is a flowchart representing an exemplary OTT CAS method.
Figure 31B:
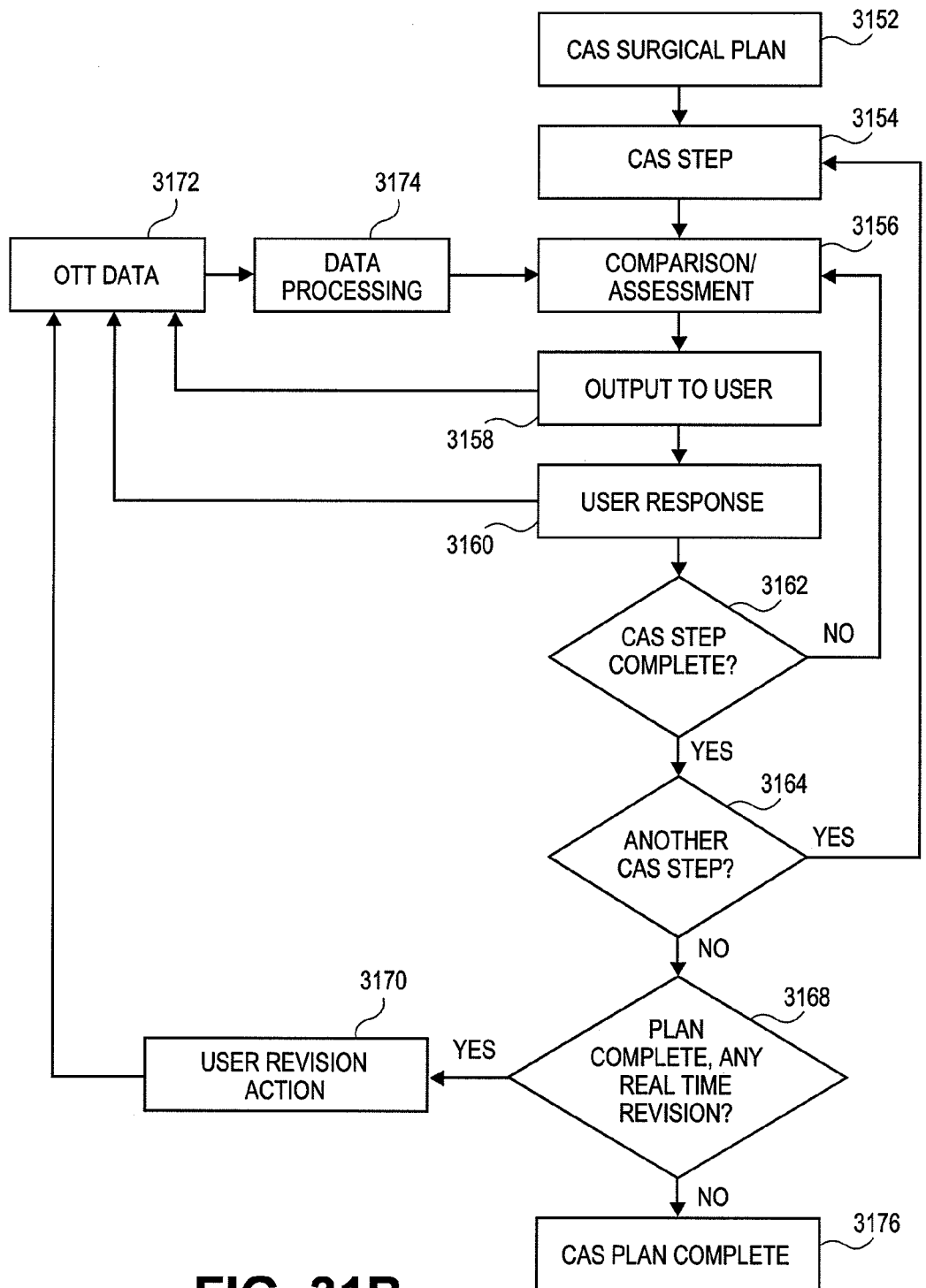
FIG. 31B be is a flowchart providing additional details of the processing steps performed using the method described in FIG. 31A.

Turning now from the general overview to more specific discussions of how computer aided surgery is modified by the use of the on tool tracking system described herein. FIG. 31A illustrates a general process flow of information for computer assisted surgery. FIG. 31B similarly represents the general step wise approach used during the actual delivery of the computer assisted surgical plan. These two flow charts will be used to provide a general frame work for the improvement to computer assisted surgery according to embodiments described herein.

With reference to FIG. 31A, information obtained by the system is processed. This can include information from a variety of sources located within the surgical field or from instruments used during surgical procedure in a continuously running feedback loop. Next, the information that has been obtained and processed is assessed using an appropriate computer assisted surgery algorithm. Finally, an output is produced from the assessment to aid the user in performance of the surgical procedure. The output produced may include one or more of the display, a projected image, or an indication. Indications may include, for example, a tactile feedback signal including for example temperature variations, a haptic feedback signal with forces or vibration of different frequency and/or amplitude, remote or onboard control of the instrument's motors or actuators with regards to their speed, direction, brake and stopping, an audio signal or visual signal provided to the user in a manner appropriate to the circumstances and use of the on tool tracking system and the instrument attached thereto.

While similar to the conventional computer aided surgery in some respects, the systems and techniques described herein are different and provide unique advantages over conventional computer assisted surgery systems and methods.

The on tool image and projection module is adapted and configured with a number of different characteristics based upon the type of computer assisted surgery being undertaken. OTT position in relation to surgical field during expected use for a CAS procedure, orientation of projector to the tool being guided, shape and surface condition (i.e., rough presence of blood or surgical debris) of the surface in the surgical field being projected on, horizontal field of view accommodation, vertical field of view accommodation are just a number of the considerations employed in the embodiments described herein.

Still other embodiments of the computer aided surgery system described herein compensate for variations and alternatives to the component selection and configurations resulting from the above described features. One exemplary compensation relates to camera adjustment or image adjustment (discussed above) for the surgical step or field adjustment based on a particular computer aided surgery technique. Another exemplary compensation relates to the actual projector position on a particular embodiment. The projector position of a particular embodiment may not be on the centerline of the device or in an optimum position based on horizontal or vertical field of view or may be tilted in order to address other design considerations such as making a device smaller or to accommodate other device components. One form of compensation for this aspect is for the projector output to be adjusted based on the actual projector location. This type of compensation is similar to keystone adjustments for a projector output. The projector provided on board the on tool tracking system may have its output compensated for the expected or actual portion of the surgical field where the projector output will display. During the surgical procedure the surgical site is likely not to be flat and so would not faithfully reflect the intended image from the projector. However, since the geometry of the target anatomy (e.g. bone surface) is known, the image to be projected by the projector can be changed by software to compensate such that when projected on the non-flat surface, it would appear clearer as intended to the user. The target anatomy surface for projection may vary in shape, orientation, curvature or presence of debris, blood and still further, the output of the OTT projector may be adjusted based on real time factors such as these detected by the OTT vision system and object detection techniques. When the cutting has started, there would be a new source of 'unflatness', namely, the interface between the original native surface of the bone, and the new surface introduced by the cut. This can be calculated (and compensated for) during cutting by logging where the cut was made, or assumed to be the desired ideal/planned surface, or digitized (e.g. with the pointer) after each cut.

Still further differences between the OTT surgical technique and conventional computer assisted surgical techniques include the types and manner of providing outputs or receiving inputs from the on tool tracking system or the user. Sensors and systems to provide tactile, haptic or motion feedback may be used as well as a variety of indicators such as alarms, visual indicators or other user inputs specific to the capabilities of a specific OTT system.

FIG. 31B relates the general OTT enabled CAS process with added details to call of additional aspects of the OTT CAS system. When the procedure begins, the user has a selected surgical tool with the on tool tracking system mounted thereto in either top mount, right side mount, left side mount or bottom mount as determined by the user and the OTT CAS plan. The tool with attached OTT is identified to the system through a tool registration procedure such as the tool transmitting an identification signal or a self-registration process or other suitable registration process. The pre-surgical planning steps, as needed, are completed according to the procedure to be undertaken. Beginning with the computer aided surgery surgical plan, the user initiates a computer aided surgery step. As a result of the use of the on tool tracking system, on tool tracking data is generated. The on tool tracking data is processed and then provided to the computer system that compares and assesses the planned surgical step information to that received from the on tool tracking data. As a result of this comparison and assessment of the on tool tracking data, an appropriate output is provided to the user or to the OTT's on board motor control circuitry as a motor or actuator control signal to slow, stop or reverse the instrument or let it continue at the speed desired by the user through the manual onboard hand trigger. This output is detected and acted upon by the on tool tracking system which provides additional data that is again provided to the tracking computer. Next the user responds to the output provided and either continues the current action, or changes the use of the tool being tracked by the on tool tracking system. The users response, whether involving action or not, is detected by the on tool tracking and becomes additional data input to the surgical computer. These processes continue as the computer system processes the progress of the step against the surgical plan. If the answer to step completion is no, comparison of data and output to the user continues. If the answer to step completion if yes, then the user may initiate the next surgical step or the surgical planning computer may provide an output to the user to notify him that one step is completed and any one of other remaining other steps can be undertaken. The sequence of CAS steps to be performed are totally up to the user, except in situations where one step cannot be performed without a prerequisite other step(s) identified in the set surgical plan. The control is totally in the hands of the user, with the computer being only (optionally) suggestive of what steps can be done, or (optionally) prohibitive of what steps cannot be done. These processes continue in accordance with computer aided surgery procedures until the plan is delivered. If the plan is complete, the use may determine whether any real-time revision of the surgical area is to be undertaken. The revision process may also be tracked and monitored to provide information to the user. If no revision is required or the CAS plan is completed, then the CAS plan is completed.

Figure 32:
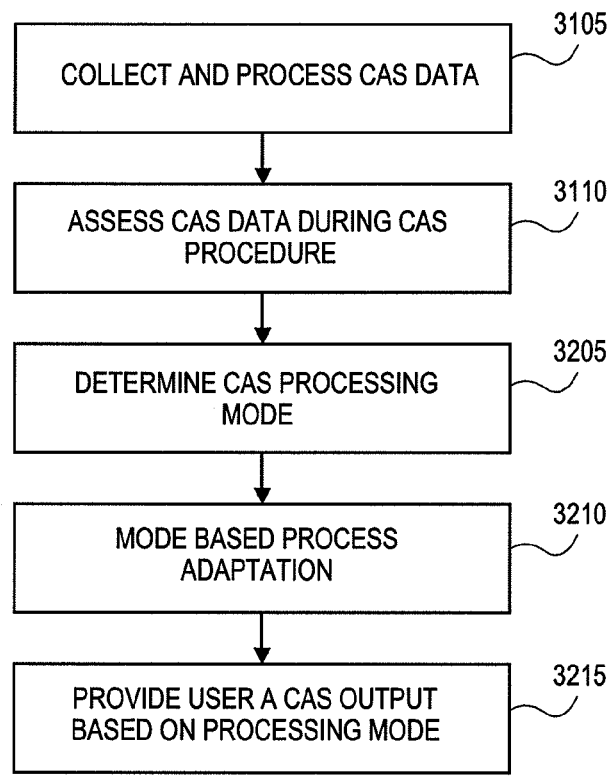
FIG. 32 is a flow chart providing exemplary additional details of the processing steps used for determining a CAS processing mode.

FIG. 32 provides a flowchart that will be used to describe still another improvement to computer aided surgery provided by embodiments of the on tool tracking system described herein. As before, the system will collect and process computer aided surgery data. Next, the computer aided surgery system will assess the CAS data during the CAS procedure. As a result of this assessment, the CAS computer will determine the CAS processing mode. Thereafter, mode based processed adaptation will be applied to the data used in the CAS process. Finally, the OTT CAS system provides a user or the instrument motor/actuator a CAS output (or speed and motor direction set-point) based on the processing mode.

Figure 33:
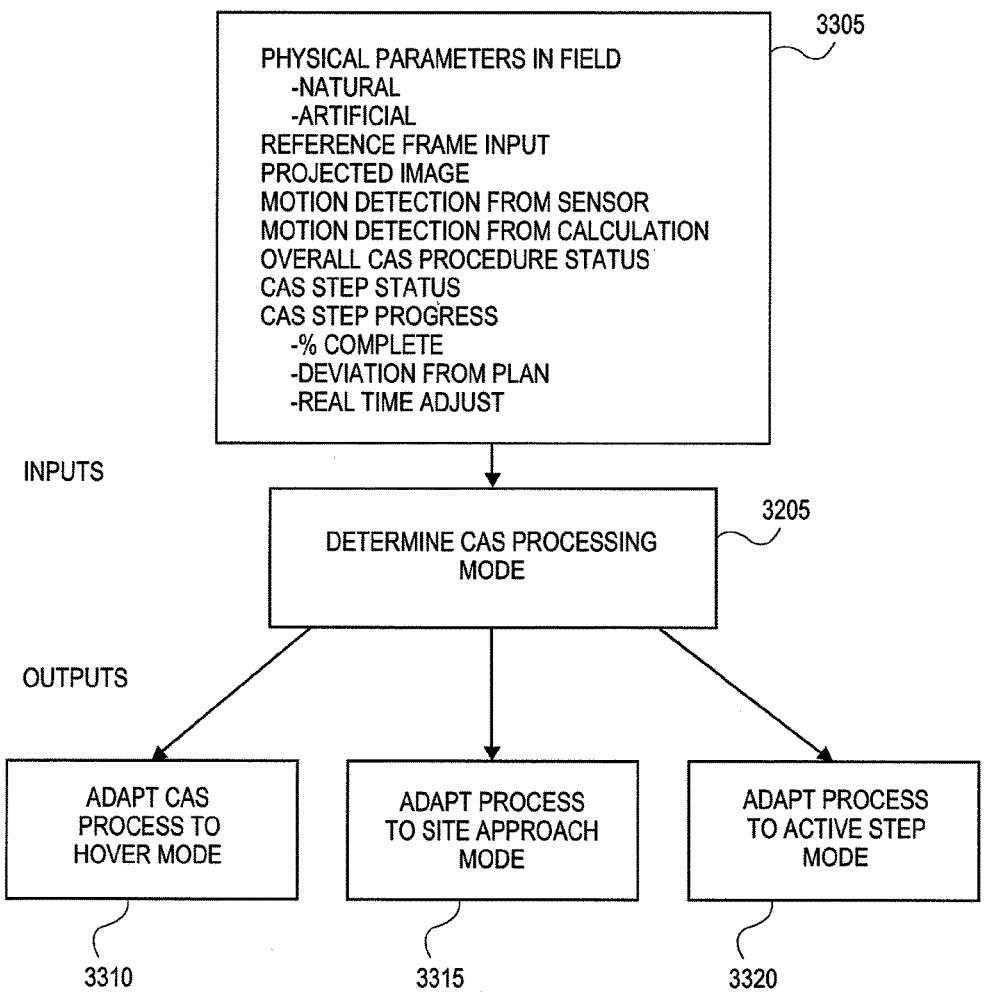
FIG. 33 is a flowchart diagramming a number of factors considered as inputs for determining a CAS processing mode as well as a representative outputs.

Mode selection relates to the OTT CAS system ability for a dynamic, real time assessment and trade off of a number of aspects of the CAS operation including the need to update the user, processing rates, cutting instrument motor control/actuation instantaneous speed and prospective response times and requirements to obtain improved or different data, relative importance of portions of data based upon CAS step progress or interaction with the patient or other factors relating to the overall responsiveness of the OTT CAS system. Additional aspects of the step of determining the CAS processing mode described above in FIG. 32 may be appreciated with reference to FIG. 33. FIG. 33 relates to the inputs considered by the system to determine the processing mode and the result of that determination. Exemplary inputs used by the OTT CAS system for determining processing mode include, by way of example and not limitation, one or more of the following: speed or motion of the tool or its motor/actuator speed, input or indication from a tool monitoring device, voice input or indication from user, physical parameters in the surgical field, including natural or artificial parameters; reference frame input; projected image; motion detection from sensors; motion detection from calculations; overall CAS procedure status; CAS step status; user input (e.g. CAS screen, motions sensor, gesture recognition, etc.); CAS step progress including, for example, percentage complete, deviations from plan, real-time adjustments. As a result of the determination step performed by the OTT CAS computer a processing mode will be selected based on the real-time circumstances and evaluation of the surgical procedure as made by the algorithms of the CAS for OTT computer. Criteria used by the OTT CAS computer for determining mode include such factors as the physical proximity of the surgical tool to the patient anatomy, actions being undertaken by the user, sensor inputs of tool motion, predicted tool motion, speed of tool motion, speed of the tool's motor or cutting actuator and other factors related to the placement, orientation, or use of a surgical tool within the OTT image field. By way of non-limiting example, CAS processing modes may include a hover mode, a site approach mode, and an active step mode. In general terms, hover mode refers to those circumstances during an OTT CAS procedure when the on tool tracker and tool is near or within the surgical field without contact between the tool and the patient. In general terms, site approach mode refers to those circumstances during an OTT CAS procedure when the on tool tracker and tool is within the surgical field and in contact with patient, but without the tool actively engaging the patient anatomy to perform a surgical step such as sawing, cutting, reaming, drilling, burring, shaving, filing and the like. In general terms, active step mode refers to those circumstances during an OTT CAS procedure when the on tool tracker and tool is engaged with the patient anatomy to perform a surgical step such as sawing, cutting, reaming, drilling, burring, shaving, filing and the like. As a result of the determine CAS processing mode decision, the OTT CAS computer will adapt the CAS processing mode to or between: hover mode, site approach mode, or active step mode as is appropriate under the circumstances.

Figure 34:
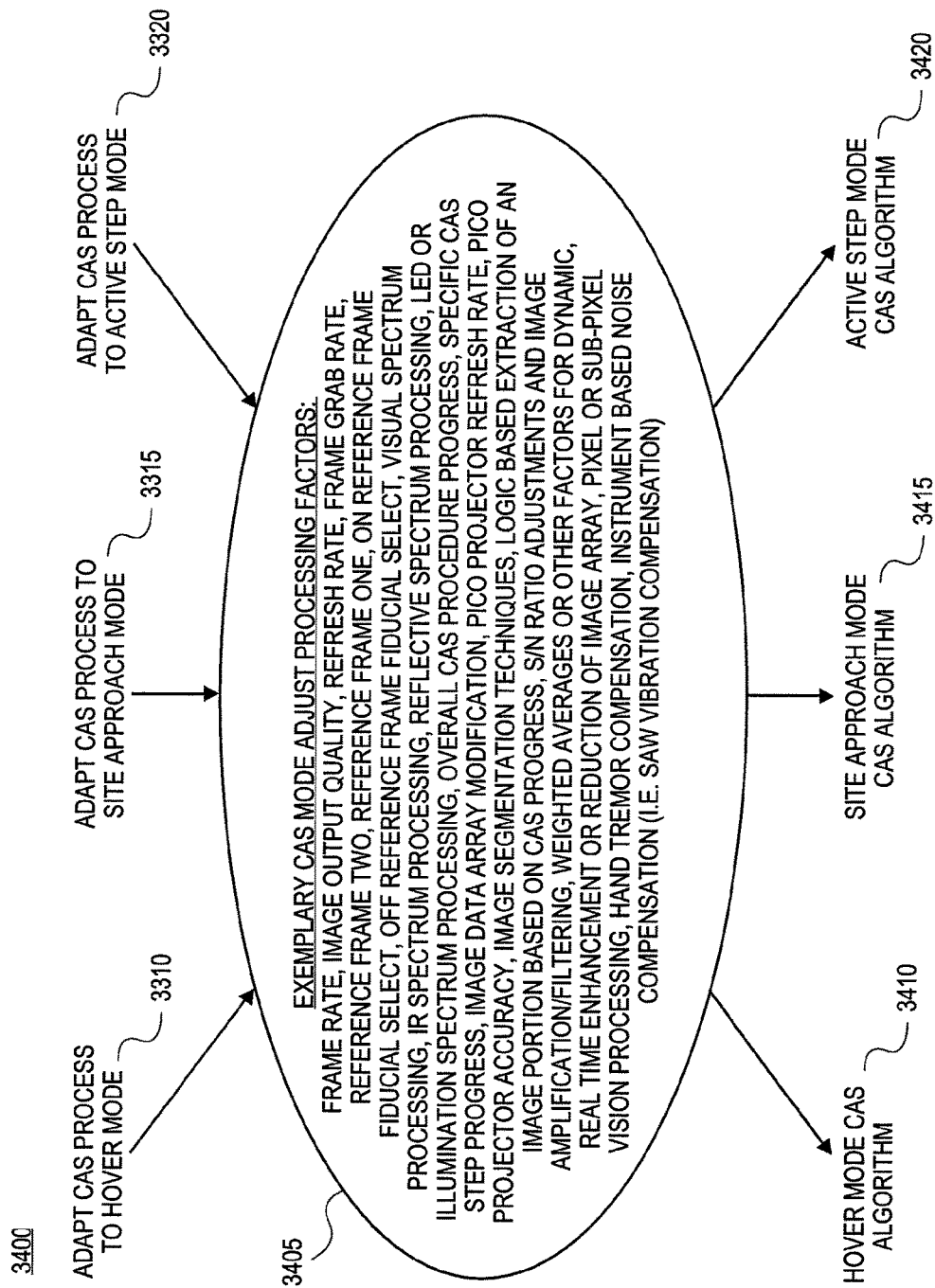
FIG. 34 is a flowchart representing the exemplary OTT CAS mode adjust processing factors used to determine the process loads for a hover mode, a site approach mode and an active step mode.

Step of adapting the CAS process to a particular mode as described above with regard to FIG. 33 is further described with reference to FIG. 34. In general terms, the OTT CAS computer is adapted and configured to adapt the CAS process mode based on adjustment factors to produce a particular mode processing algorithms. By way of example, the various mode adjust processing factors are shown in FIG. 34. Based on the processing inputs as detailed in the flowcharts above, the OTT CAS computer will adjust the processing steps undertaken for OTT CAS based on one or more of or combinations of or variations of the following CAS mode processing adjustment factors: camera frame size and/or camera orientation (if camera software or firmware provides for such adjustment); adjustments to camera image outputs to modify a size of a region of interest within a horizontal field of view, the vertical field of view or both the horizontal and the vertical field of view of the camera; drive signals for adjustable camera lens adjustment or positioning; image frame rate; image output quality; refresh rate; frame grabber rate; reference frame two; reference frame one; on reference frame fiducial select; off reference frame fiducial select; visual spectrum processing; IR spectrum processing; reflective spectrum processing; LED or illumination spectrum processing; surgical tool motor/actuator speed and direction, overall CAS procedure progress; specific CAS step progress; image data array modification; pico projector refresh rate; pico projector accuracy; image segmentation techniques; logic-based extraction of an image portion based on a CAS progress; signal-to-noise ratio adjustment; image amplification and filtering; weighted averages or other factors for dynamic, real-time enhancement or reduction of imager rate, pixel or sub-pixel vision processing; hand tremor compensation; instrument-based noise compensation (i.e. saw vibration compensation). Put another way, the various factors listed above may be grouped into the various ways of providing adjustments of the camera based on those adjustments that can take place within the camera such as in the software or firmware or operating modalities provided by the camera electronics themselves on the one hand. And on the other hand, on a broader scale, the overall adjustment of the camera in its housing in relation to the OTT housing. In this way camera movement speaks of a more general shifting of the entire camera body or the camera lens itself rather than internal electronic modifications or adaptations of camera output based on electronic processing of camera image information. For within camera variations these are such things as focal point, zoom, exposure, aperture and other camera based modifications that will adjust the cameras output as part of an imaging adjustment In one specific example, one or more of the above features are used to produce a hover mode CAS algorithm that is used during hover mode processing adaptation. In one specific example, one or more of the above features are used to produce an approach mode CAS algorithm that is used during approach mode processing adaptation. In one specific example, one or more of the above features are used to produce an active step mode CAS algorithm that is used during active step mode processing adaptation.

Figure 35:
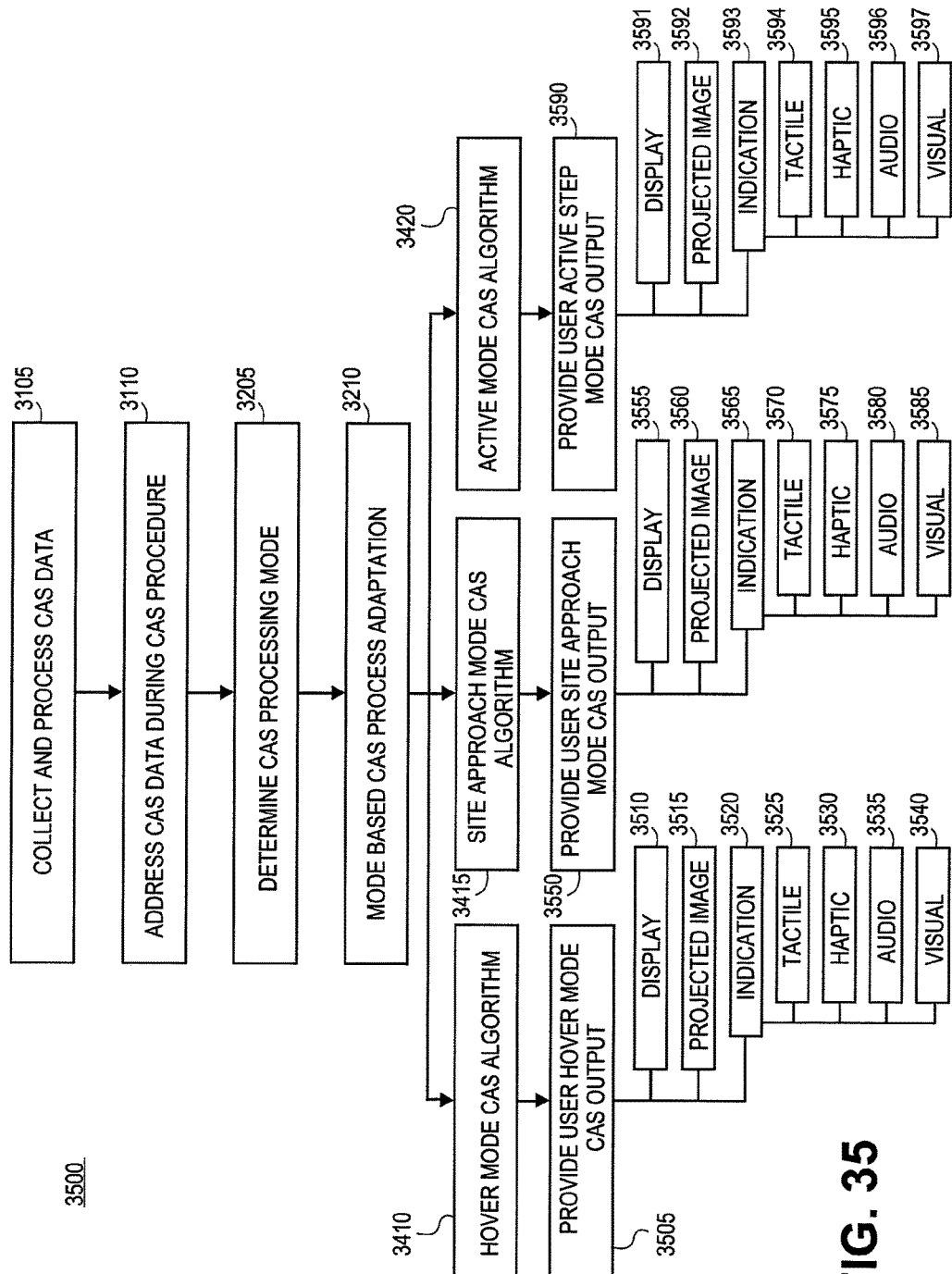
FIG. 35 is a flowchart representing an exemplary OTT CAS process including the result of an OTT CAS process adaptation and the resultant mode algorithm and modified outputs thereof.

FIG. 35 illustrates a flowchart of an exemplary OTT CAS process building upon the steps described above. Collect and process CAS data. Assess CAS data during a CAS procedure. Determine CAS processing mode. Undertake mode based CAS assess adaptation. Based on the result of the mode based determination, if hover mode, apply hover mode CAS algorithm to processing. Provide the user with hover mode CAS outputs, or provide the OTT motor control circuitry with speed control commands/signals. Exemplary user outputs include hover mode display outputs, hover mode projected image outputs, hover mode indications such as tactile, haptic, audio and visual indications adapted to the processing steps used in the hover mode. Based on the result of the mode based determination, if site approach mode, apply site approach mode CAS algorithm to processing. Provide the user with site approach mode CAS outputs. Exemplary outputs include approach mode display outputs, approach mode projected image outputs, approach mode indications such as tactile, haptic, audio and visual indications adapted to the processing steps used in the approach site mode.

Based on the result of the mode based determination, if active step mode, apply active step mode CAS algorithm to processing. Provide the user with active step mode CAS outputs. Exemplary outputs include active step mode display outputs, active step mode projected image outputs, active step mode indications such as tactile, haptic, audio and visual indications adapted to the processing steps used in the active step mode.

Figure 36:
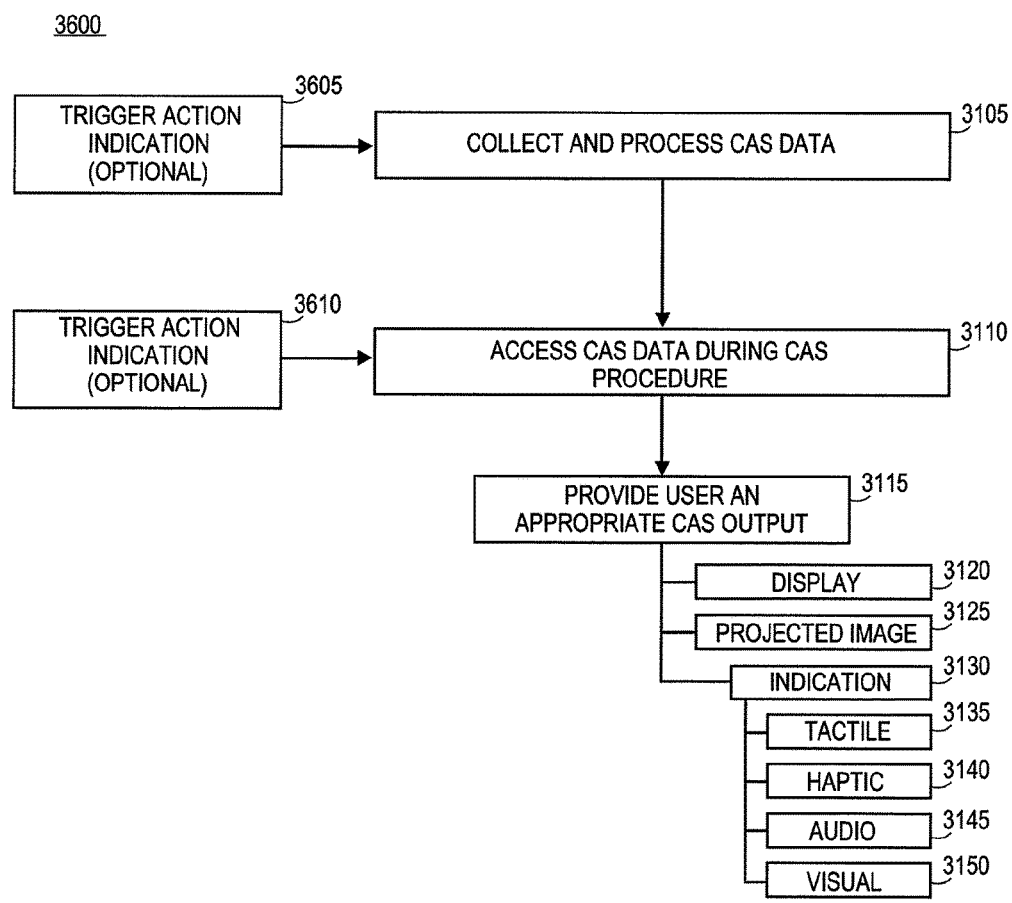
FIG. 36 is a flowchart representing an exemplary OTT CAS process including modification of any of the above described OTT CAS processes to include associated surgical tool operational characteristics, parameters or other data related to the use of an active element in any OTT CAS process or procedure.

FIG. 36 illustrates a flowchart amid exemplary OTT CAS process based upon those described above but using a unique trigger action indicator tool monitor or tactile or haptic feedback to further provide benefits to users of an OTT CAS system. Various alternative embodiments of the trigger action indicator are provided below with regard to FIGS. 37A-52B. As before, the OTT CAS process proceeds by collecting and processing CAS data. In one alternative aspect, the collection and processing may also include an indication from the trigger action. Next, following the processes described above, the OTT CAS system will assess CAS data during a CAS procedure. Here again, a trigger action indication may also be applied to this step and assessed along with other CAS data. Thereafter, the user will be provided with an appropriate CAS output based upon the use of one or more trigger action indicators as described above. The appropriate CAS outputs may include a display, a projected image, or any of a number of indications such as tactile indications, haptic indications, audio indications or visual indications as described above or as are typical in CAS procedures.

Against this backdrop of the various aspects of OTT CAS processes, the following examples are provided.

It is to be appreciated that OTT CAS mode may be detected and determined by many factors (e.g., reference frame(s), positions, relative motion, etc.). Additionally, in the context of a surgical procedure, there is also benefit in relating the defining attributes of an OTT CAS mode based on tool/target proximity or use. Consider the following examples of: A) Hover: both tool and target within surgical field, but no contact; B) Approach: Both tool and target within surgical field AND they are in contact; and C) Active step mode: Both tool and target within surgical field AND they are in contact AND there is active engagement of tool with tissue. In one aspect, the OTT device electronics incorporates this mode selection functionality in a 'smart views' module. This module is provided within the main CAS system computer or within the OTT device where electronics including software and firmware implement all or a substantial part of the modes detection algorithms, and triggers the different events of the OTT CAS mode selection functionality.

In some additional aspects of OTT CAS mode control, one or more of the following variations or alternatives may be incorporated:

1. Due to the temporal/special resolution on an OTT CAS system and CAS system generally, some embodiments of the Approach mode may be considered appropriate when tool and target are within a given user-preselected (settable) distance envelope. The distance envelope may be designated in a measurement range. One exemplary range may be between 10 mm to 0 mm as determined by the OTT CAS system. In other aspects, the Approach mode may be delineated by the OTT CAS system determining that there is likely contact between an active element of a surgical tool and the anatomy within the OTT CAS surgical field.
2. In some aspects, an OTT CAS mode is provided with a 'hysteresis' factor. This OTT CAS hysteresis factor is selected to include the types of circumstances or CAS conditions that, if satisfied such as continuously for a pre-determined time period, will result in that CAS mode being maintained. In other words, the parameters of the OTT CAS mode hysteresis must be met continuously during a period of time to 'lock into the mode' or maintain that OTT CAS mode. As used herein, continuously is meant to be within the context of the time domains of OTT processing times and sample rates and is not intended to denote the absolute non-interruption of the conditions monitored. By way of similar example, the hysteresis or some of the hysteresis conditions have to NOT be met continuously during a period of time to 'un-lock' or permit adjustment of the OTT CAS mode. The use of OTT CAS mode hysteresis factors improves the system response to transients, avoids or reduces the likelihood of the system to jump from one OTT CAS mode to another inappropriately and improves usability of the system since the user is likely to see more stable OTT CAS outputs as the system will be providing those outputs from a single OTT CAS mode.
3. During some OTT CAS steps, there are activities performed by the user that may not require use of the projector, may require different input-output (JO) devices (e.g. during implant location assessment it may not be possible to project information on the bone), and/or may not have a defined target-tool relationship (e.g. knee range of motion assessment only requires seeing tibial and femoral reference frames). It is to be appreciated that the OTT CAS system may also receive inputs from other sources and there are OTT CAS outputs where no projector output is provided or utilized.
4. In general, the processing algortihms and OTT CAS mode factors are selected based on the probability or likelihood that, as for such things as the relative motion for bones, instruments, implants, etc. will be decreasing as the OTT CAS mode progresses from Hover to Active. The one exception to this general process assumption is when the OTT CAS device or system is used for the process of an assessment of a range of motion for an involved joint within the surgical field or for that joint that is the objective of the OTT CAS procedure or step.

OTT CAS Mode Examples

Bone registration:

Objective: Finding out the geometrical relation between the origin of the reference frame and the origin of the bone model.

Procedure: Digitization of points on the surface of the bone with a tool (e.g. navigated pointer), and processing of these points against pre-determined geometry data of the bone model How the OTT CAS system identifies this task:

Pointer's AND bone's (either tibia or femur) reference frames (RFs) are visible to OTT.

Initiation of the task:

The OTT CAS system recognizes both reference frames coexisting in the scene (for at least a minimum period of time suited for this registration)

An additional 'guess' factor is the stage of the procedure because for example, cutting cannot be done until the bones are registered.) In this case, the trigger for this event may be the OTT device is maintained in position to keep two reference frames within the field of view until a bone registration process is completed. This trigger can optionally be confirmed by the system computer prompting the user to confirm and they respond.

The information obtained during OTT device bone registration may be annotated or overwritten if needed by user's input (touch screen, voice command, touching with the pointer on a specific divot on the bone's reference frame, etc.)

OTT CAS Modes

Hovering:

Range Condition: OTT device is too far away from the RFs, or the 2 RFs are too far apart. The range to trigger this condition is settable during the calibration/tuning of the system, or by user preferences, and is specified as a distance threshold between the cameras to the target anatomy reference frame beyond the optimum FOV (in our embodied case greater than 200 mm).

Tracker: Lower refreshing rate

Projector: May not project any image on the bone (as the bone location is not yet defined), but can project elementary helpful information such as confirming this mode/status etc. on any reflective surface which happens to be in the way. Low refreshing rate, limited by the trackers.

System: Monitors the pointer's tip and the bone's RF location in 'world' coordinates. Drives tracker, projector, and other IO devices.

Approach:

Range Condition: Medium OTT/RFs and RF/RF distances. The range to trigger this condition is settable during the calibration/tuning of the system, or by user preferences, and is specified as a distance range from the target anatomy reference frame such as 100-200 mm.

Tracker: High refreshing rate, optimizing pointer and bone RFs readings (e.g. ignoring or disregarding other RF's)

Projector: As above, may not project any defined image (as the bone location is not yet defined), but can project a solid screen that changes colors (e.g. red, yellow and green) based on 'readiness' to start collecting registration points.

System: Monitors the pointer's tip and the bone's RF location in 'world' coordinates. Drives tracker, projector, and other IO devices.

Active:

Smaller OTT/RFs and RF/RF distances. For example, less than 70-100 mm distance from the target reference frame, again settable by user preferences as above.

Tracker: High refreshing rate, optimizing pointer and bone RFs readings

Projector: As above.

System: Monitors the pointer's tip and the bone's RF location in 'world' coordinates. Records pointer's tip location for each digitized bone. Drives tracker, projector, and other IO devices. Monitors progress of the registration process, and when finished it calculates the final registration matrix.

May or may not require additional IO device (e.g. touch screen)

OTT CAS considerations for transitions between modes:

Mode shift is based on distance thresholds.

If there is no bone registration information then it is not possible to determine bone-pointer 'contact' or 'closeness'. The system alternatively looks at a nominal distance between the pointer (which IS registered) and the bone's reference frame (instead of the bone itself). The resulting nominal distance may then be used to estimate or assume approximate registration based on the nominal position in which that (bone) reference frame is usually recommended to be placed (see picture sheet 18-23). Another alternative is to (optionally) simply use any old registration information by the system (of another default bone or one from a previous patient or surgery) to make the approximate registration for the purposes of determining what "mode" the system should be in. The availability of this option is also settable/selectable by the user.

Or by user's input.

End of the task:

All registration landmarks have been visited and pointed (registration process is fully completed).

OR the system ceases to see the pointer's RFs (for at least a minimum period of time)

Alternatively, the process could be complemented or overwritten by user's input (touch screen, voice command, touching with the pointer on a specific divot on the bone's reference frame, etc.)

Bone cutting/drilling:

Objective: Re-shaping the bone with a tool (usually a powered, smart instrument such as a saw, drill, burr, file, etc.) to allocate and implant.

Procedure: Following the system's direction, the user cuts/drills (usually) one surface at a time. This particular activity applies to different individual 'target surfaces' on each bone, one per cut/hole to be performed, so the system will maintain such reference when using or processing locational or orientational errors of the tool relative to the bone. Different tools have different active elements (e.g. cutting tips), and so the different active elements of each tool shapes result in different 2D and 3D modification of the anatomy when the tool or tool active element interacts with the anatomy in the surgical field. As such, the guidance for each tool will vary with the type of tool and active elements in use during an OTT CAS process step.

How the system OTT CAS system identifies this task:

OTT detects at least one bone's reference frame (RFs).

The named bone is registered.

The reference frame of the bone being cut is within a user selectable maximum distance (say, for example only, less than 200 mm).

Initiation of the Task:

The system recognizes both RFs coexisting in the scene (for at least a minimum period of time)

This could be complemented or overwritten by user's input (touch screen, voice command, touching with the pointer or the cutting instrument on a specific divot or mark on the bone's reference frame or the bone itself, etc.)

Modes

Hovering:

OTT is too far away from the bone. For example, more than 200 mm (values settable by the user).

Tracker: Lower refreshing rate

Projector: May not project any image (the bone could be out of the projector's sight) or may just display rough shapes (e.g. arrows to indicate in what direction to move the instrument—e.g. saw, drill, etc.—to align it with the bone). Optionally, the projector output is modified to simply show different colors as in the previous example. Low refreshing rate, limited by the tracker's refresh settings.

System: Monitors the tool location and orientation relative to the bone (i.e. in bone's coordinates). Drives tracker, projector, and other IO devices. Communicates bi-directionally and drives smart instruments.

Approach:

OTT is at medium distance to the bone. For example, between 100 mm and 200 mm.

Tracker: High refreshing rate, optimizing pointer and bone RFs readings.

Projector: Shows alignment aids (colored text, lines, circles, arrows, etc.) corrected for bone geometry at medium refreshing rate.

System: Monitors the tool location relative to the bone (i.e. in bone's coordinates) and calculates roll, pitch, yaw, and distances deviations. Drives tracker, projector, and other IO devices. Communicates bi-directionally and drives smart instruments.

Active:

OTT is close to the bone. For example, between 70 mm and 100 mm.

Tracker: High refreshing rate, optimizing pointer and bone RFs readings.

Projector: Shows alignment aids (colored text, lines, circles, arrows, etc.) corrected for bone geometry at high refreshing rate.
System: Monitors the tool location relative to the bone (i.e. in bone's coordinates) and calculates roll, pitch, yaw, and distances deviations. Drives tracker, projector, and other IO devices. Communicates bi-directionally and drives smart instruments at higher speed.
Transition between modes:
Transition may be based on distance thresholds.
Transition based on user input.
End of the task:
User moves on to another task
All cuts and refinements are fully completed.
In one alternative, the OTT CAS system ceases to see the bone's RFs (for at least a minimum period of time)
This step could be amended, complemented or overwritten by user's input (touch screen, voice command, touching with the pointer on a specific divot on the bone's reference frame, etc.)
Assessment of bone cut:
Objective: Evaluating a new surface (e.g. plane, cylindrical hole, etc.) orientation, surface roughness, depth, etc.
Procedure: Total or partial digitization of the surface (e.g. touching/traversing it with a navigated pointer), assessing a cut location and orientation with a 'surface monitor' (a navigated tool with a flat surface that sits on the flat cut), gaging the depth of a hole with a navigated pointer, etc.
How the OTT CAS system identifies this task:
OTT sees at least one bone's reference frame (RFs) as well as the assessing instrument's (surface monitor or pointer) RF.
The named bone and the instrument have been registered.
At least a cut has been performed.
The bone being cut is within a maximum distance 'D'.
Initiation of the task:
The system recognizes both RFs (bone and instrument) coexisting in the scene (for at least a minimum period of time), while the conditions above are fulfilled.
This could be complemented or overwritten by user's input (touch screen, voice command, touching with the pointer or the cutting instrument on a specific divot or mark on the bone's reference frame or the bone itself, etc.)
Modes
Hovering:
OTT is too far away from the RFs, or the 2 RFs are too far apart.
Tracker: Lower refreshing rate.
Projector: May not project any defined image (as the bone can be out of projector's sight), or it can project a solid screen that changes colors (e.g. red, yellow and green) based on 'readiness' to start the process. Low refreshing rate, limited by the tracker's.
System: Monitors the tool location relative to the bone (i.e. in bone's coordinates). Drives tracker, projector, and other IO devices.
Approach:
OTT is at medium distance to both RFs AND medium bone-tool distance.
Tracker: High refreshing rate, optimized for instrument and bone RFs readings.
Projector: May not project any defined image (as the bone can be out of projector's sight), or it can project a solid screen that changes based on 'readiness' to start the process. Medium refreshing rate.
System: Monitors the tool location relative to the bone (i.e. in bone's coordinates). Drives tracker, projector, and other IO devices.
Active:
OTT is at medium/close distance to both RFs AND small bone-tool distance.
Tracker: High refreshing rate, optimized for instrument and bone RFs readings.
Projector: May not project any defined image (as the bone can be out of projector's sight), or it can project a solid screen that changes based on process status (start to end of data collection). High refreshing rate.
System: Monitors the tool location relative to the bone (i.e. in bone's coordinates). Records pointer's tip location for each digitized point or surface monitor location and orientation. Drives tracker, projector, and other IO devices. Monitors progress of the assessment process, and when finished it calculates, records and displays the calculated parameters.
May or may not require additional IO device (e.g. touch screen)
Transition between modes:
Simply based on distance thresholds.
Or by user's input
End of the task:
Assessment process is fully completed.
Optionally, the OTT CAS system ceases to see the instrument's RFs (for at least a minimum period of time)
This could be complemented or overwritten by user's input (touch screen, voice command, touching with the pointer on a specific divot on the bone's reference frame, etc.)
Assessment of implant fit and alignment
Objective: Comparing the actual location of the implant (or trial) on a bone, relative to where it was expected to be according to plan. This can happen during trial, and before/during/after implant cementing or locking.
Procedure: An implant (e.g. femoral component, tibial tray, etc.) gets a RF attached, and is tracked in 'bone' coordinate system. At any given time the system can display/record its position (relative to the bone), and instant errors (if any) compared to where it was supposed to be.
How the system identify this task:
OTT sees at least one bone's reference frame (RFs) as well as the corresponding implant's RF.
The named bone and the implant have been registered.
All cuts have been performed.
The bone being and implant are within a maximum distance 'D'.
Initiation of the task:
The system recognizes both RFs (bone and implant) coexisting in the scene (for at least a minimum period of time), while the conditions above are fulfilled.
This could be complemented or overwritten by user's input (touch screen, voice command, touching with the pointer or the cutting instrument on a specific divot or mark on the bone's reference frame or the bone itself, etc.)
Modes
Hovering:
OTT is too far away from the RFs, or the 2 RFs are too far apart.
Tracker: Lower refreshing rate.
Projector: May not project any defined image (as the bone can be out of projector's sight), or it can project a solid screen that changes colors (e.g. red, yellow and green)

based on 'readiness' to start the process. Low refreshing rate, limited by the tracker's.
System: Monitors the implant/trial location relative to the bone (i.e. in bone's coordinates). Drives tracker, projector, and other IO devices.
Approach:
Medium OTT/RFs distance AND implant/trial relatively close to the bone.
Tracker: High refreshing rate, optimized for implant/trial and bone RFs readings.
Projector: May not project any defined image (as the bone can be out of projector's sight), or it can project a solid screen that changes based on 'readiness' to start the process. Medium refreshing rate.
System: Monitors the implant location relative to the bone (i.e. in bone's coordinates). Drives tracker, projector, and other IO devices.
Active:
Smaller OTT/RFs distance AND implant/trial is close/touching to the bone.
Tracker: High refreshing rate, optimized for implant and bone RFs readings.
Projector: May not project any defined image (as the bone can be out of projector's sight), or it can project a solid screen that changes based on process status (start to end of data collection). High refreshing rate.
System: Monitors the implant/trial location relative to the bone (i.e. in bone's coordinates). Calculates and displays (and record when needed) the errors defined by the actual location/orientation of the navigated implant relative to where it is supposed to be according to plan. Drives tracker, projector, and other IO devices. Monitors progress of the assessment process, and when finished it calculates, records and displays the calculated parameters.
May or may not require additional IO device (e.g. touch screen)
Transition between modes:
Simply based on distance thresholds.
Or by user's input
End of the task:
Assessment process is fully completed.
(or) The system ceases to see the instrument's RFs (for at least a minimum period of time)
This could be complemented or overwritten by user's input (touch screen, voice command, touching with the pointer on a specific divot on the bone's reference frame, etc.)
Range of motion:
Objective: Assess the range of motion and biomechanics of the joint after implantation. It can be done with trials or final implants on.
Procedure: After placing the trial (or actual implant) on, before removing the bones' RFs and closing the wound, the surgeon flexes the knee and performs handles the joint, reaching limit positions like maximum flexion and hyper extension). This maneuvering is performed while pointing OTT to the tibial and femoral RFs. Dynamic measurements (tibia relative to femur) are expressed in anatomical terms.
How the system identify this task:
OTT sees both tibia's and femur's reference frames (RFs).
Both bones have been cut. (Bone cutting and implant location could have or could have not been performed.)
Initiation of the task:
The system recognizes both RFs coexisting in the scene (for at least a minimum period of time), while the conditions above are fulfilled.
This could be complemented or overwritten by user's input (touch screen, voice command, touching with the pointer or the cutting instrument on a specific divot or mark on the bone's reference frame or the bone itself, etc.)
Modes
Hovering:
OTT is too far away from the RFs.
Tracker: Lower refreshing rate.
Projector: May not project any defined image (as the bone can be out of projector's sight), or it can project a solid screen that changes colors (e.g. red, yellow and green) based on 'readiness' to start the process. Low refreshing rate, limited by the tracker's.
System: Monitors the tibia location relative to the femur. Drives tracker, projector, and other IO devices.
Approach:
Medium OTT/RFs distance.
Tracker: High refreshing rate, optimized for bones' RFs readings.
Projector: May not project any defined image (as the bone can be out of projector's sight), or it can project a solid screen that changes based on 'readiness' to start the process. Medium refreshing rate.
System: Monitors the implant location relative to the bone (i.e. in bone's coordinates). Drives tracker, projector, and other IO devices.
Active:
Smaller OTT/RFs distance AND implant/trial is close/touching to the bone.
Tracker: High refreshing rate, optimized for implant and bone RFs readings.
Projector: May not project any defined image (as the bone can be out of projector's sight), or it can project a solid screen that changes based on process status (start to end of data collection). High refreshing rate.
System: Monitors the tibia location relative to the femur. Calculates and displays (and record when needed) the dynamic motion (flexion/extension, varus/valgus, internal/external rotation, AP motion, etc.). Drives tracker, projector, and other IO devices. Monitors progress of the assessment process, and when finished it saves all parameter recorded and notifies the user.
May or may not require additional IO device (e.g. touch screen)
Transition between modes:
Simply based on distance thresholds.
Or by user's input
End of the task:
Assessment process is fully completed.
(or) The system ceases to see the bones' RFs (for at least a minimum period of time)
This could be complemented or overwritten by user's input (touch screen, voice command, touching with the pointer on a specific divot on the bone's reference frame, etc.)
Other activities (e.g. registration verification, bone cut refinement, etc.) can be considered sub-cases of the above.
In one aspect in any of the above described examples, lower refreshing rate refers to changes in refresh rate from about 30-100 Hz to as low as 1-10 Hz.
When resecting a portion of a bone a surgeon may cut more rapidly and aggressively when the cutting tool is relatively far from the boundary of the area to be resected.

As the OTT CAS detects the surgeon approaching the boundary of the resection area, the surgeon may receive appropriate OTT CAS outputs to slow the pace of cutting to ensure that the resection remains within the desired boundaries. To help the surgeon readily assess the proximity to the resection boundary, the OTT CAS system may provide a number of appropriate OTT CAS outputs to the surgeon as the surgeon approaches the boundary. Further still, the OTT CAS system may be configured to provide feedback related to the control the operation of the OTT equipped surgical tool in response to the proximity of the tool to the resection boundary and the corresponding OTT CAS data processing response and resulting CAS outputs.

As described above, the OTT CAS system provides for the pre-operative analysis of a patient model and the identification of the tissue to be resected. After the portion of the tissue to be resected is determined, the OTT CAS system may analyze the data for the model and identify the boundary for the resection. The tissue to be resected may then be identified in the OTT projector output using a plurality of colors based on the relation to the resection boundary.

For instance, the OTT projector output may be adapted based on OTT CAS processing factors to project onto a portion of the tissue that is not to be removed in red. Optionally, the OTT projector output may indicate a portion of the tissue that is to be resected that is relatively close to the resection boundary in yellow. In still another alternative, the OTT CAS processes may produce an OTT projector output whereby the remainder of the tissue to be resected may be eliminated in green. In this way, as the surgeon views the surgical field during a procedure the surgeon may cut rapidly and aggressively while the OTT projector output indicates the tool is operating on tissue in the green zone. As the surgeon approaches the resection boundary, the OTT-based projector output indicates the tool is operating on tissue in the yellow zone. These OTT CAS determined projector outputs serve as indications to the surgeon to proceed more slowly as the tool approaches the resection boundary. In this way, the OTT CAS system provides a readily identifiable visual and graphical display directly onto the surgical field that informs the surgeon of the proximity of the current surgical action to a resection boundary. Similarly, the OTT CAS system can be used to visually recognize and use an OTT-based projector output to identify the proximity of the surgical tool to sensitive anatomical structures, such as nerves, vessels, ligaments etc. OTT CAS output to the projector may include distinctive color schemes to identify the structures within the surgical field as part of OTT CAS output for the user.

FIGS. 37A-44 relate to various alternative tactile feedback mechanisms along with related kinematic responses and design criteria.

FIG. 37A illustrates a bent form that deflects to move an actuator in response to trigger force. FIG. 37B illustrates a sliding trapezoid form that will deform and restore its shape in response to trigger force. FIG. 37C illustrates a rotating reader or encoder used to provide a rotating response to the trigger force. FIG. 37D illustrates a frame moving in response to trigger force to depress a shaft into a base where the movement of the shaft may be registered as an indication of trigger force. FIG. 37E illustrates a pinned element that may deflect to indicate an amount of trigger force.

Figure 38A:
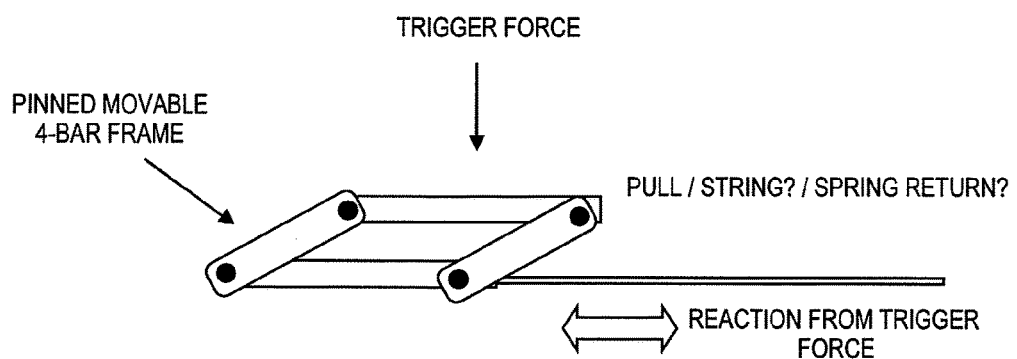
FIGS. 38A and 38B illustrate a simple four bar mechanism, in a raised and lowered, positions respectively that may be used to register trigger force and displace a shaft.
Figure 38B:
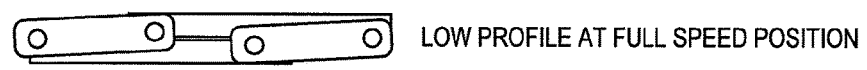

FIGS. 38A and 38B illustrate a simple four bar mechanism, in a raised and lowered, positions respectively that may be used to register trigger force and displace a shaft.

FIGS. 39A, 39B 39C each illustrate a scissor mechanism 80 without a position restoration element (39A) and driving an actuator 80, with a tension spring as a position restoration element 84 (39B) and a compression spring as a position restoration element 84 (39C). The movement of the actuator shown determines the height of the upper end of the scissor arms therefore the elevation of the scissor mechanism. This height will press against, and will be felt by the user placing his or her finger on the tool trigger.

Figure 40A:
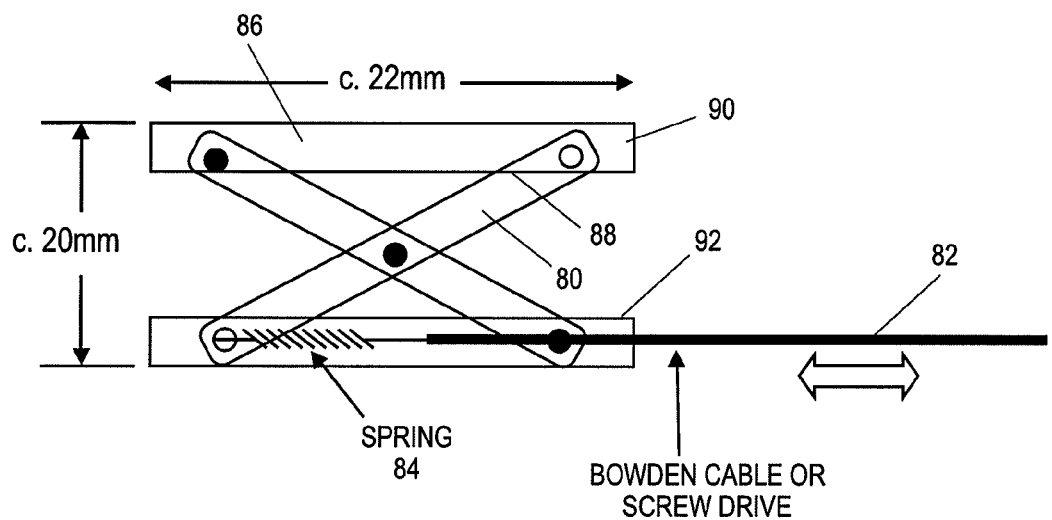
Figure 40B:
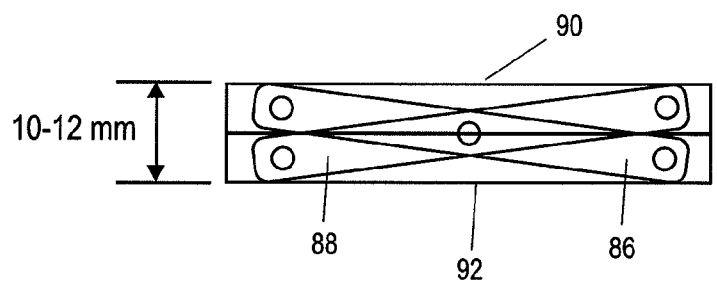

FIGS. 40A and 40B illustrate a side view of a scissor mechanism in a raised and lowered configuration, respectively. The scissor mechanism 80 includes a first link 86 and a second link 88 coupled at a pivot point whereby movement of the scissor raises and lowers the first and second platforms 90, 92. A position restoration element 84, here shown as a spring, is coupled to one end of the second link and to an actuator 82. The platforms have a length of about 22 mm and a maximum rise of about 20 mm in the elevated condition shown in FIG. 40.

Figure 40C:
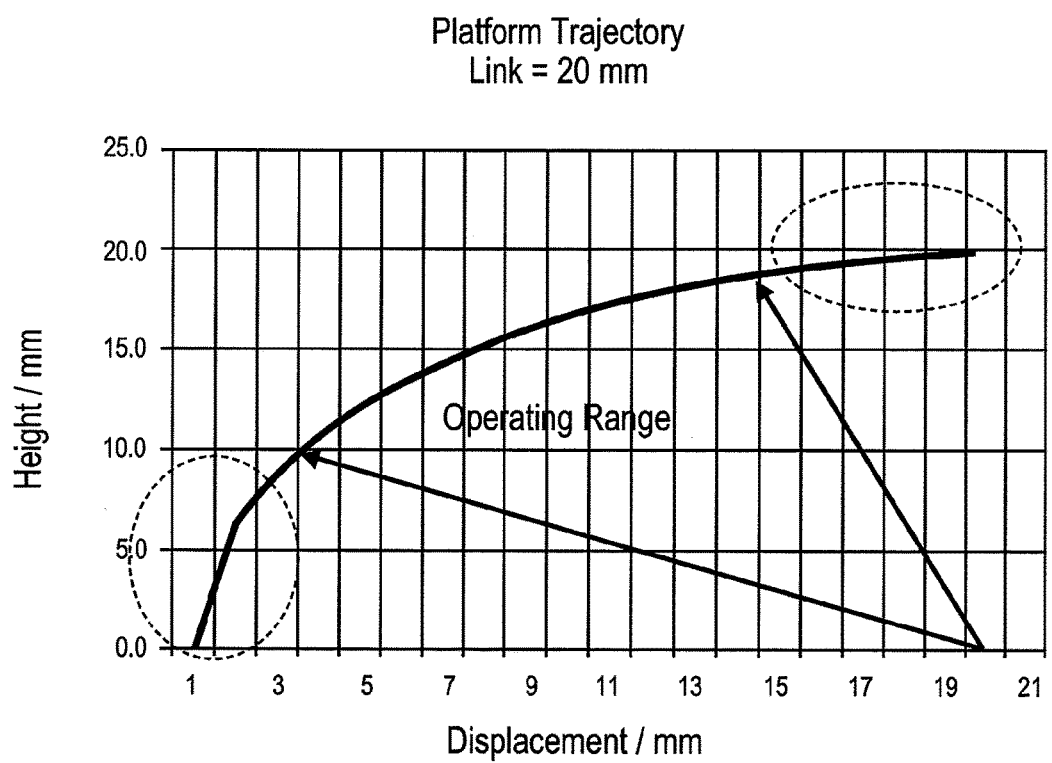
Figure 40D:
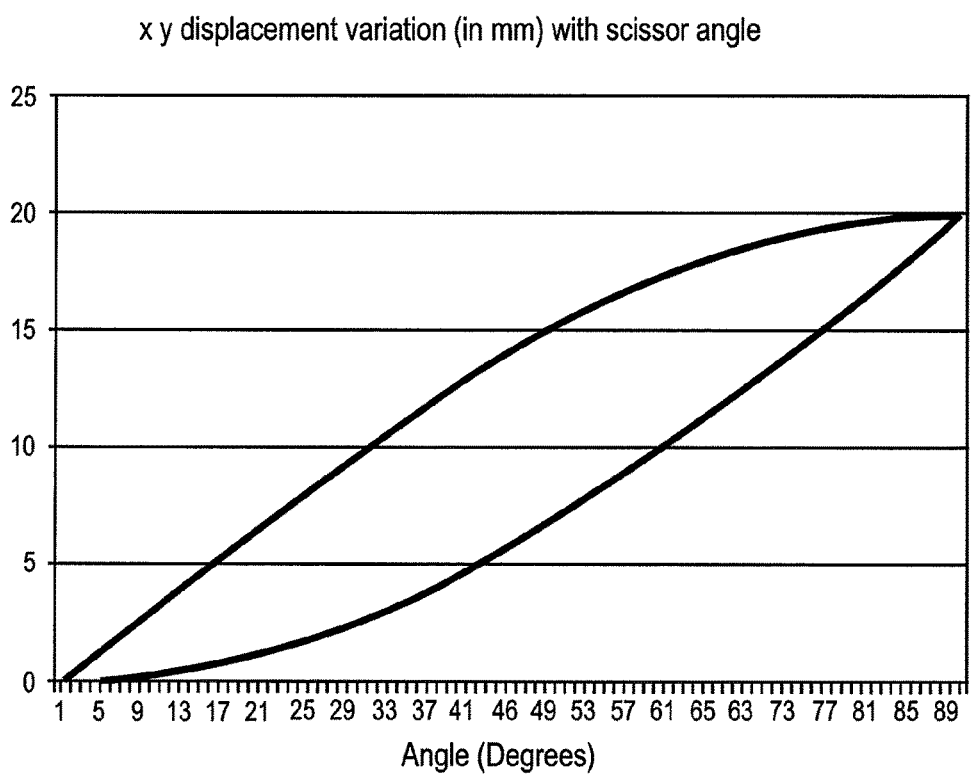

FIGS. 40C and 40D are charts relating to the displacement characteristics of the scissor mechanism 80 of FIGS. 40A and 40B. FIG. 40C relates a platform trajectory with a height of the device. FIG. 40D relates to the scissor angle with the displacement variation of the device.

Figure 41:
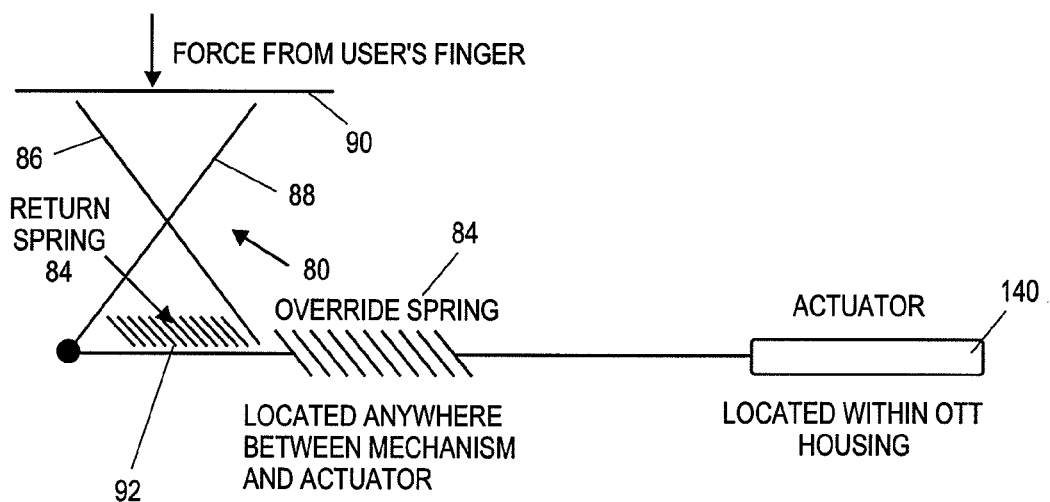

FIG. 41 illustrates another scissor mechanism 80 having a surgeon system override capability. The override capability is provided via the inclusion of a spring in line with the force application through the actuator. The actuator may be a component 140 is used for providing or receiving OTT CAS data during computer assisted surgery procedures. In this aspect, the on tool tracking device includes a component 140 adapted and configured to translate a movement received from a feedback mechanism, such as from the shaft 80 relative movement into a signal used in a computer assisted surgery procedure. The component 140 may be provided in a number of different configurations such as an encoder, an actuator or a motion transducer. In one aspect, the signal relates to the operation of the surgical tool operated by the trigger. In still a further embodiment, the component is or is adapted to include an actuator to impart movement to the shaft to influence the relative movement between the first platform and the second platform. In a further aspect, the actuator is configured to impart movement to the shaft in response to a signal related to controlling the operation of the surgical tool during a computer assisted surgery procedure.

The illustrated scissor mechanism embodiment shows the relationship of the first platform 90 and the second platform 92 borne by the links 86, 88 of the scissor mechanism 80. In addition, this embodiment shows a scissor mechanism having a pair of position restoration elements used in conjunction with the scissor mechanism 80. One position restoration element is the return spring positioned within the scissor mechanism 80. Another position restoration element is the override spring positioned between the scissor mechanism and the actuator or component 140.

Figure 42:
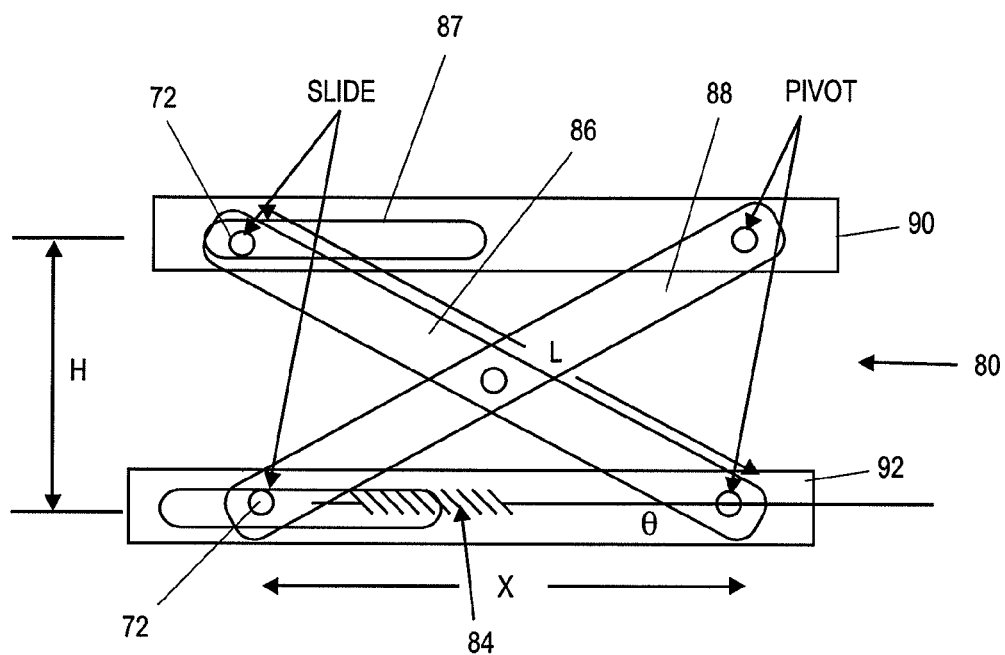
Figure 43:
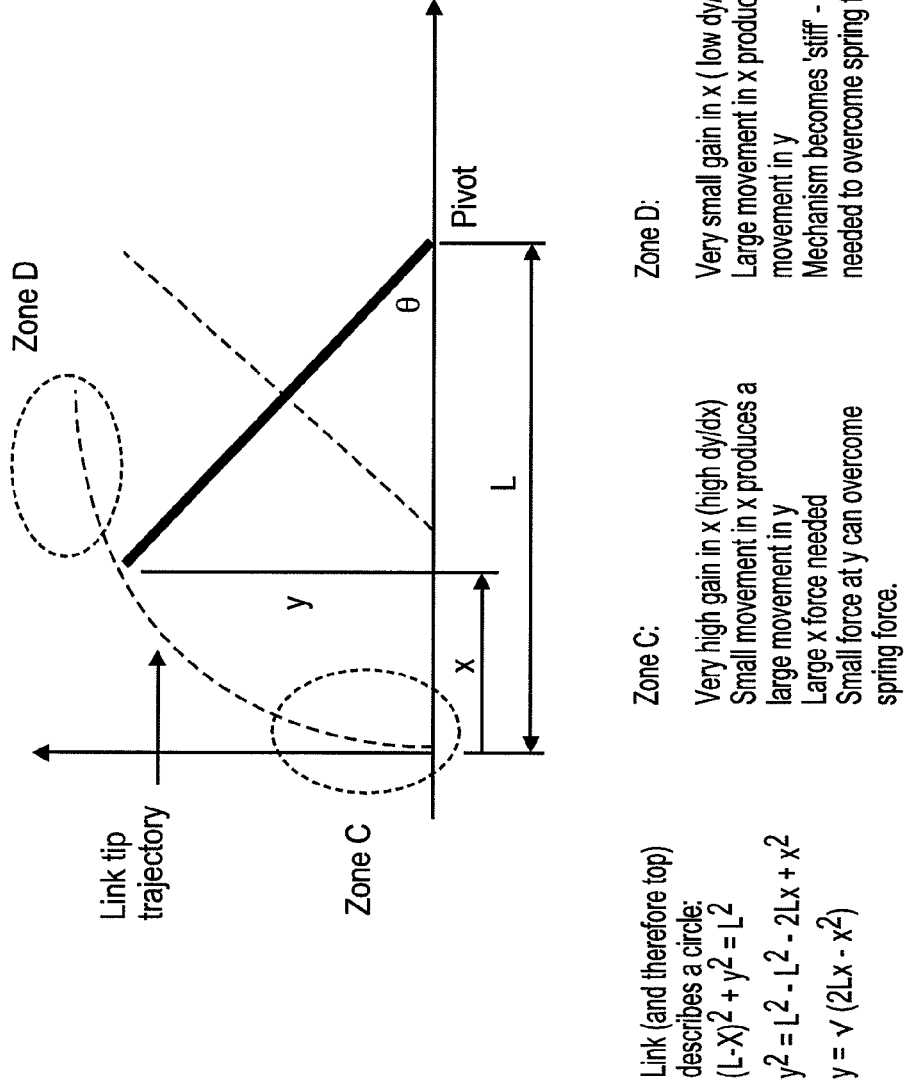
Figure 44:
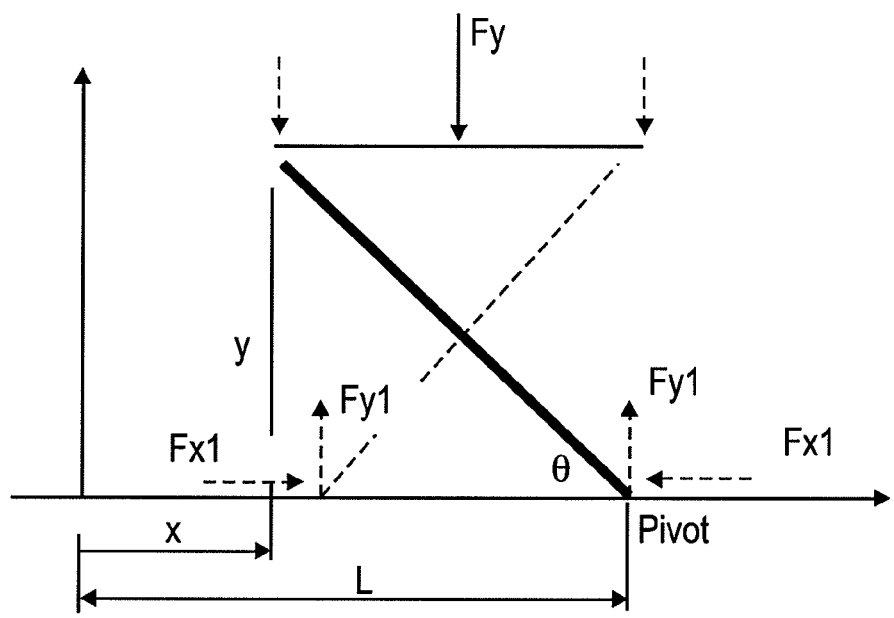

FIG. 42 illustrates a scissor mechanism similar to the schematic mechanism illustrated in FIG. 41. The scissor mechanism 80 includes a first platform 90 and the second platform 92 connected at one end of the links 80, and 86 in the pivoting relation to the first and second platform and sliding relation with the other end of the links 88, 86. A position restoration element, here a spring, is placed between the actuator or cable and a sliding and of a scissor link 88. This embodiment also includes the details of the elongate slots the first and of the platforms to permit sliding movement of the link first end relative to the first and second platform. The second end of the links 88, 86 are coupled in pivoting relation to the first platform and the second platform 90, 92. Here the motion of the first and second platforms is adjusted to the use of the spring or under the influence of the actuator. The operational characteristics of the mechanism of FIG. 42 are better appreciated with reference to the charts and FIGS. 43 and 44.

Figure 45:
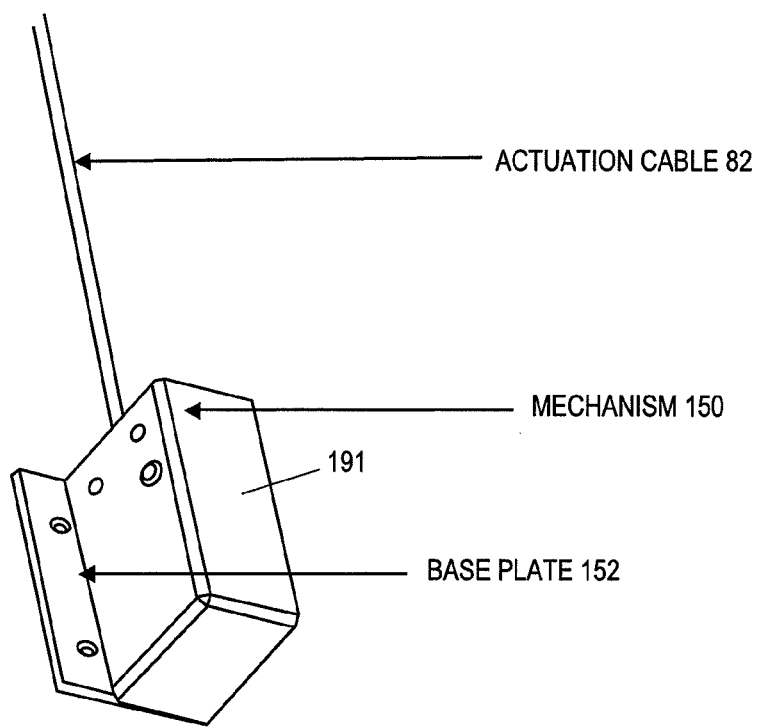
FIG. 45 is an isometric view of a tactile feedback mechanism.
Figure 46A:
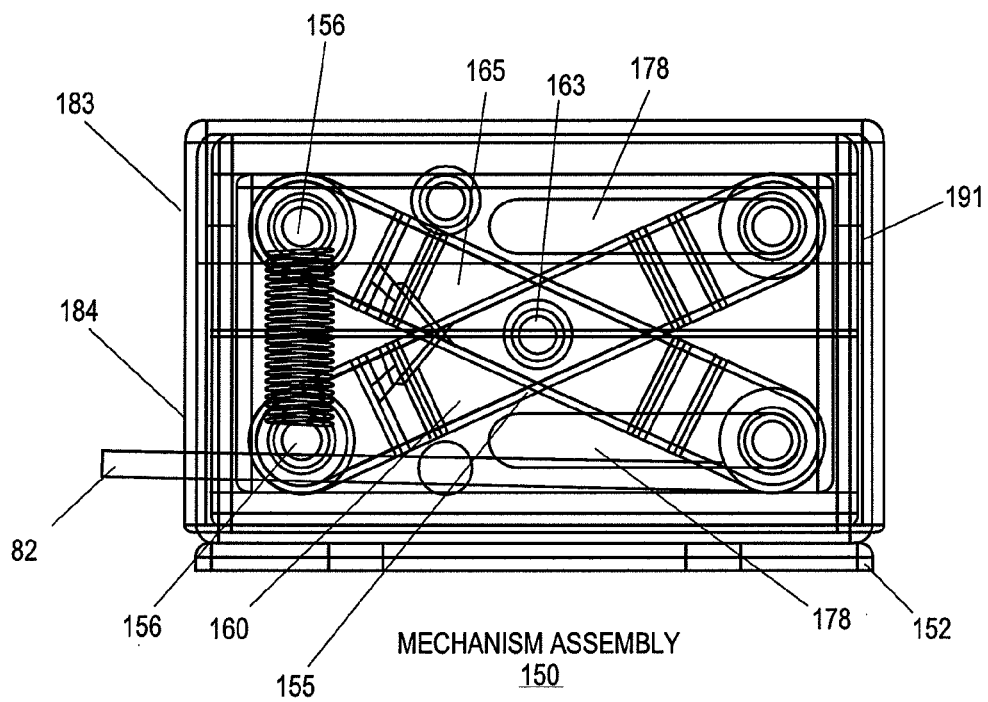
FIGS. 46A-46F illustrate various views of the components and operation of the mechanism of FIG. 45.

FIG. 45 is an isometric view of a tactile feedback mechanism. FIGS. 45 and 46A illustrate isometric and side views of a tactile feedback mechanism 150, respectively. The view of FIG. 45 shows the base plate 152 use for attachment to a surgical tool 50 adjacent a trigger 52. The scissor mechanism (best seen in FIG. 46A) is covered by a cover 191 that is borne by the first platform 183 and moves along with the platform. An actuation cable 82 is coupled to the scissor mechanism and moves in response to movement of the scissor mechanism.

Figure 46B:
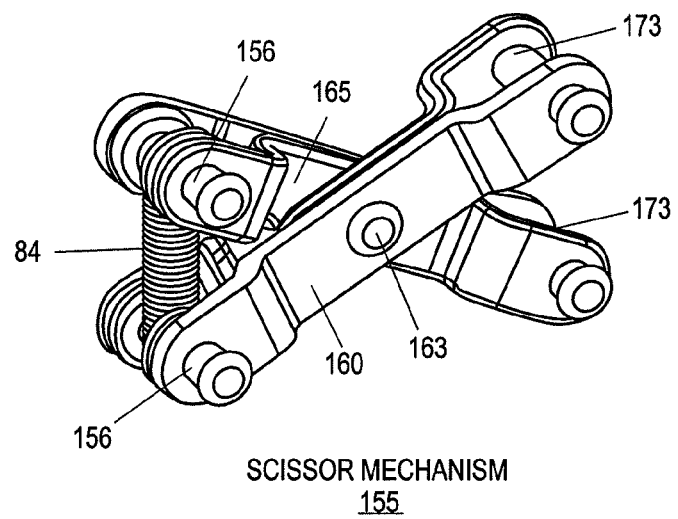

FIG. 46B illustrates an isometric view of the scissor mechanism 155 of FIG. 46A without the cover 191 or the platforms 183, 184. The Y-shaped linkage 160 and 165 are pinned 163 to form a scissor mechanism 155. A position restoration element 84 is positioned between the first ends of the first link and the second link. Also visible in this view are is the shaft 173 used to slide along the slots 178 in the platforms.

Figure 46C:
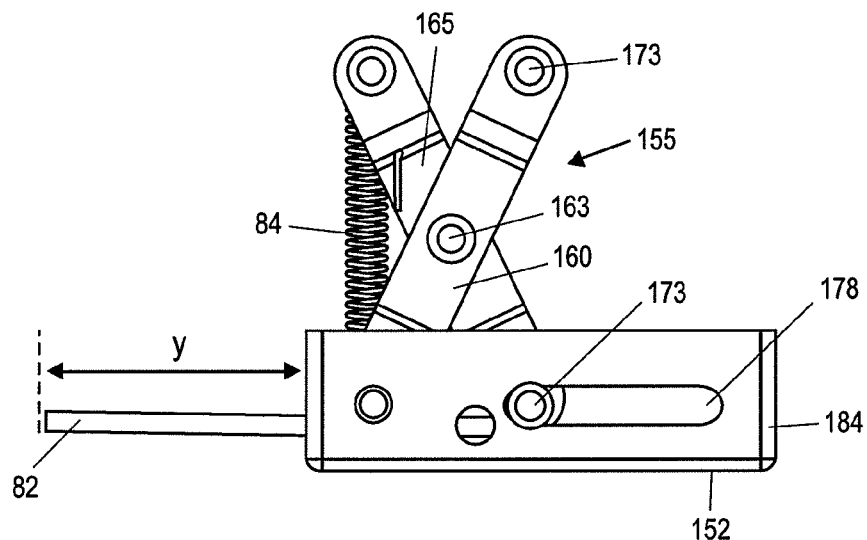
Figure 46D:
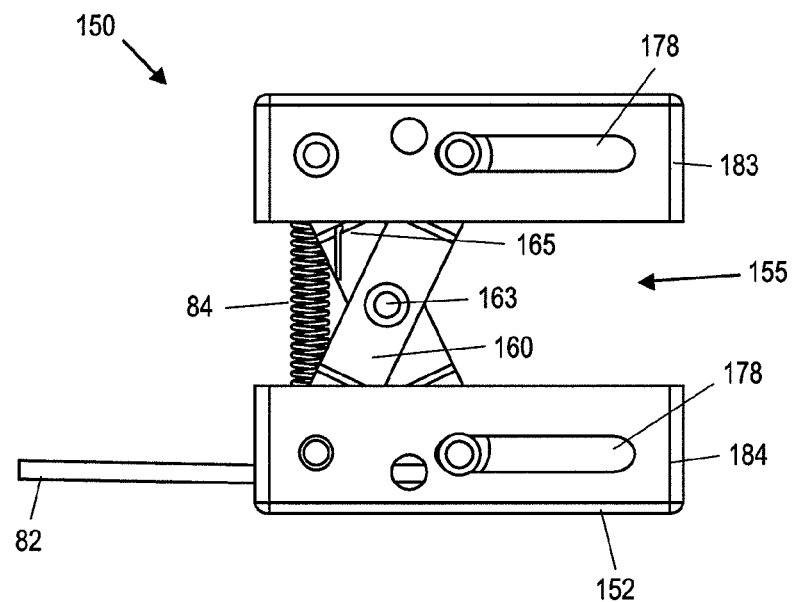

FIGS. 46A-46F illustrate various views of the components and operation of the mechanism of FIG. 45. FIGS. 46C and 46D show the TFM 150 of FIGS. 45 and 46A in an extended condition with (FIG. 46D) and without (FIG. 46C) the top platform 183. The cable 82 is moved a displacement +y from the lower platform 184 in relation to the length of movement of the links along the slots 178.

Figure 46E:
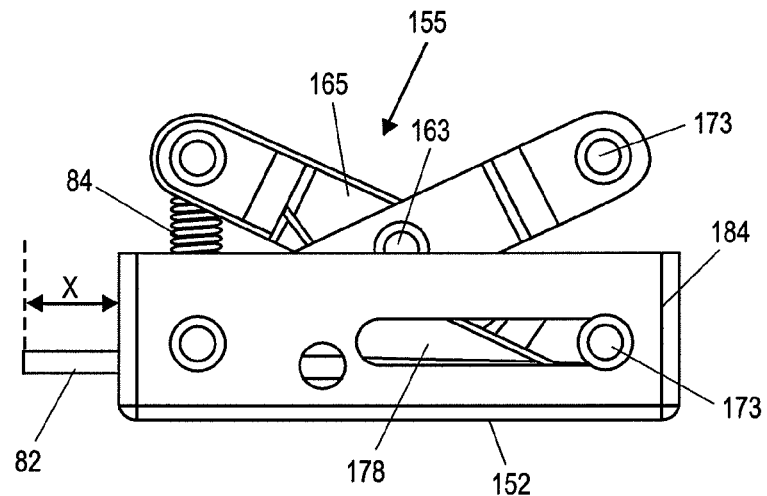
Figure 46F:
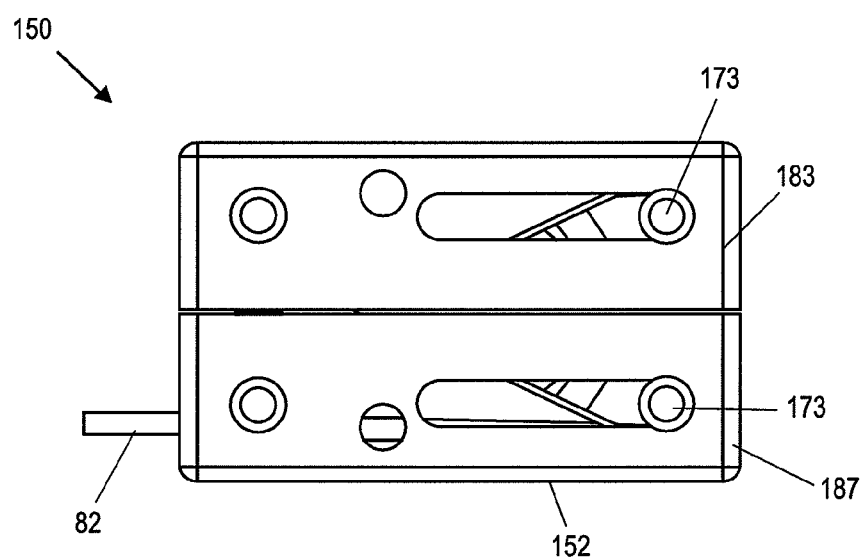

FIGS. 46E and 46F show the TFM 150 of FIGS. 45 and 46A in an closed or retracted condition with (FIG. 46F) and without (FIG. 46E) the top platform 183. The cable 82 is moved a displacement +x from the lower platform 184 in relation to the length of movement of the links along the slots 178.

Figure 47:
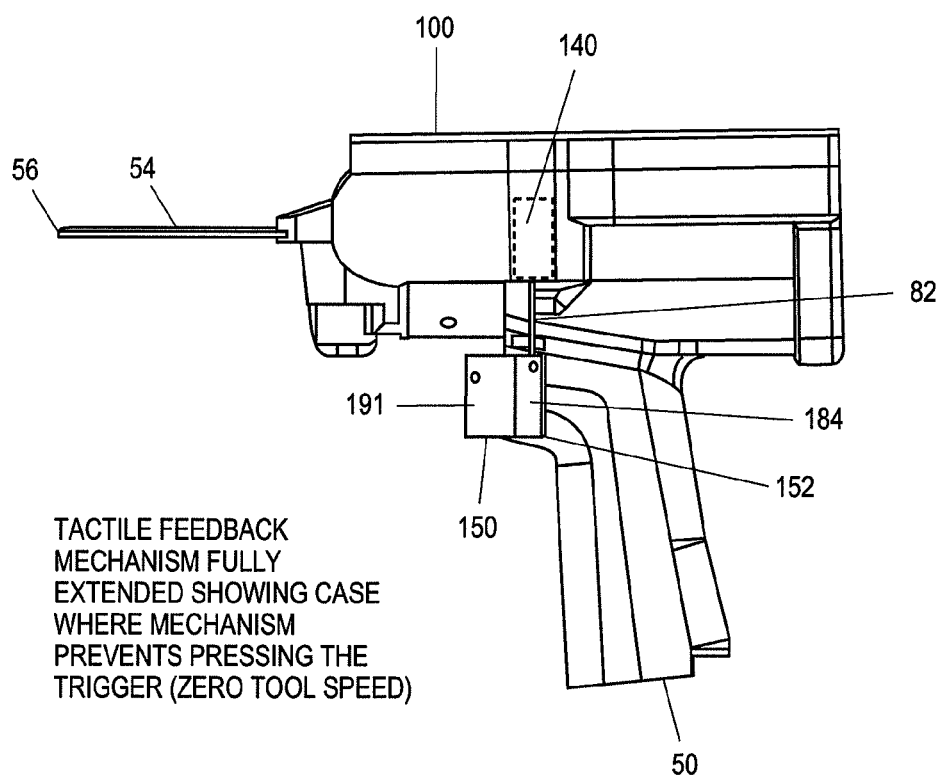
FIGS. 47 and 48 illustrate a side view of an on tool tracing device mounted on a surgical instrument having a tool (here a saw) with the tactile feedback mechanism of FIG. 45 in position to interact with the trigger of the surgical instrument.
Figure 48:
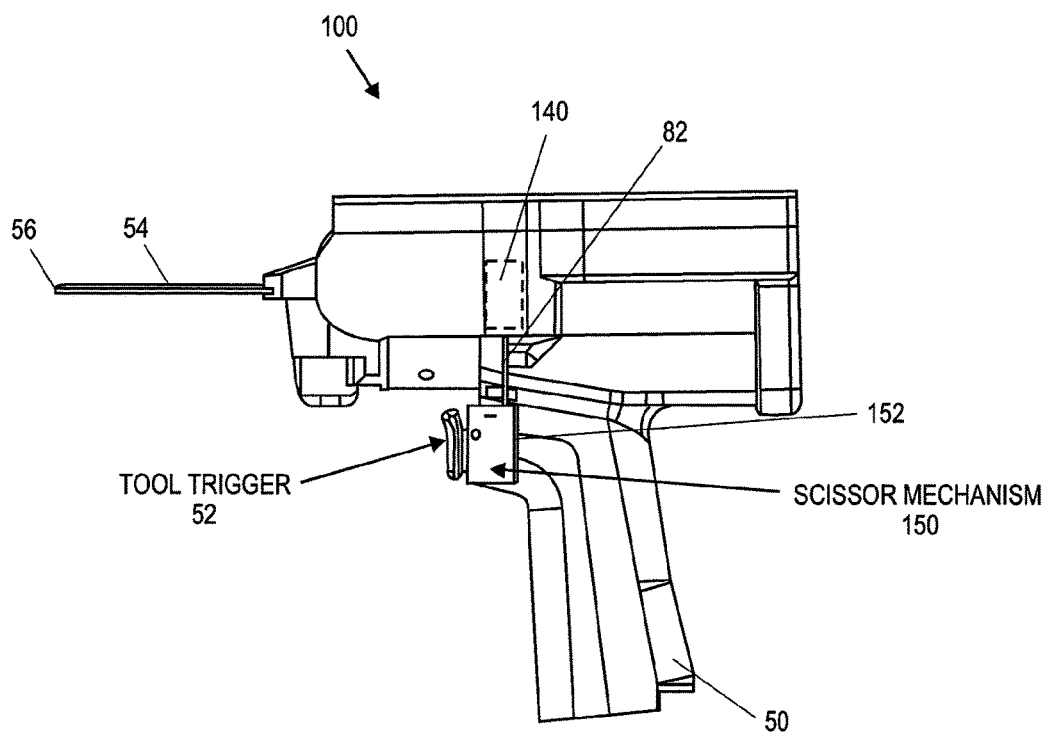

FIGS. 47 and 48 are side views of an OTT 100 on a surgical tool 50 having a TFM 150 positioned adjacent the trigger of the surgical tool. The actuator 82 extends from the TFM into the OTT 100. A component 140 within the OTT is configured to receive and provide output to or receive from the TFM. In this embodiment, the cover 191 is expended away from the base 152 exposing a portion of the base 184.

When the TFM moves the cover 191 into the position show, the trigger function on the surgical tool is impaired by the cover 191 that blocks access to the trigger 152. FIG. 48 illustrates the cover 191 in a losered configuration where the trigger 52 is accessible.

FIGS. 47 and 48 illustrate a side view of an on tool tracking device mounted on a surgical instrument having a tool (here a saw) with the tactile feedback mechanism of FIG. 45 in position to interact with the trigger of the surgical instrument. FIG. 47 illustrates the tactile feedback mechanism in an expanded configured that covers the trigger and FIG. 48 shows the tactile feedback mechanism collapsed to expose the trigger.

Figure 49A:
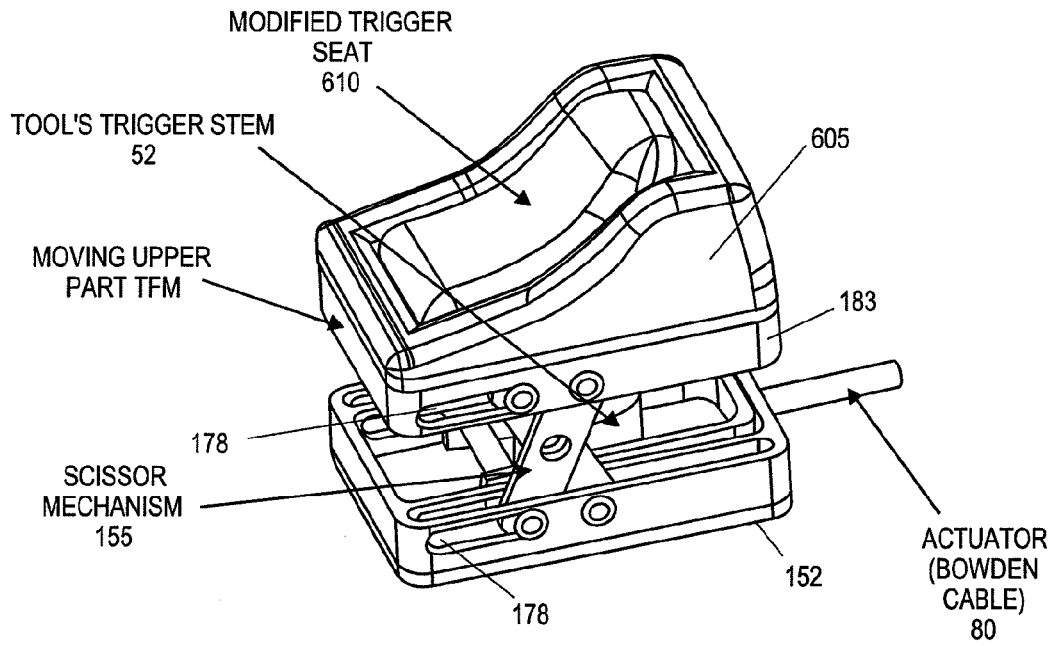
FIGS. 49A-49B illustrate another alternative of a tactile feedback mechanism in an open or expanded state (FIG. 49A) and a closed state (FIG. 49B).
Figure 49B:
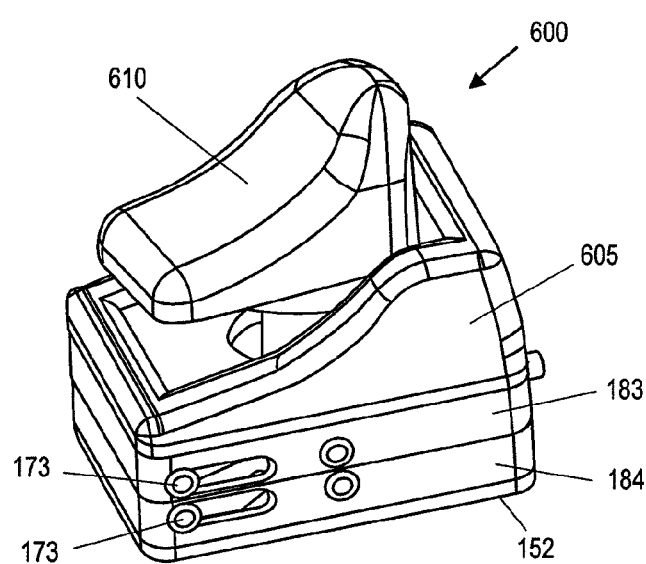
Figure 49C:
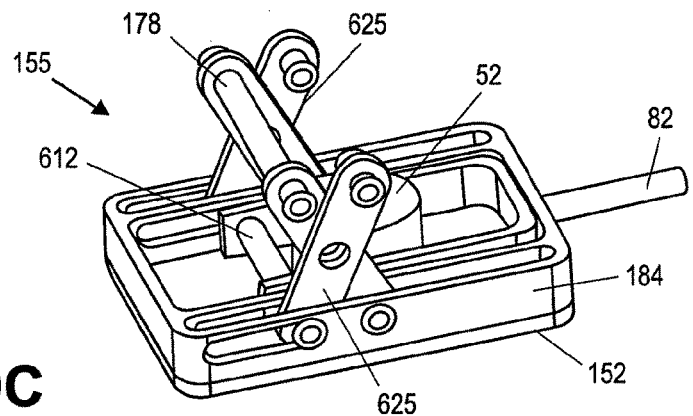
FIGS. 49C-49E illustrate the various views of the internal mechanisms of the devices in FIGS. 49A and 49B.
Figure 49D:
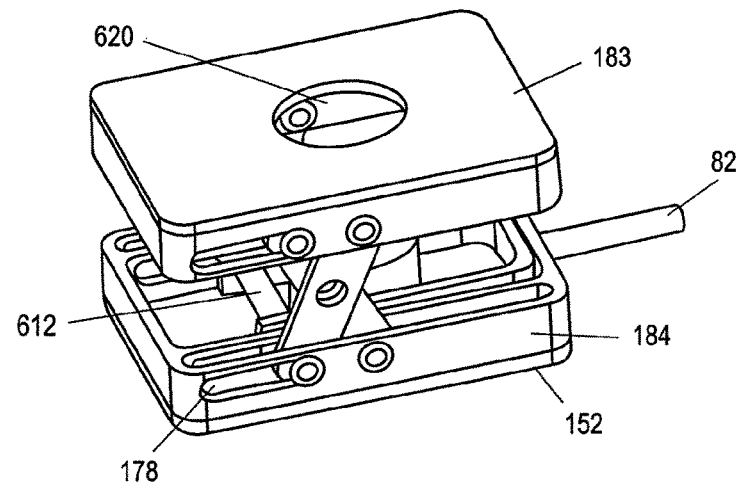
Figure 49E:
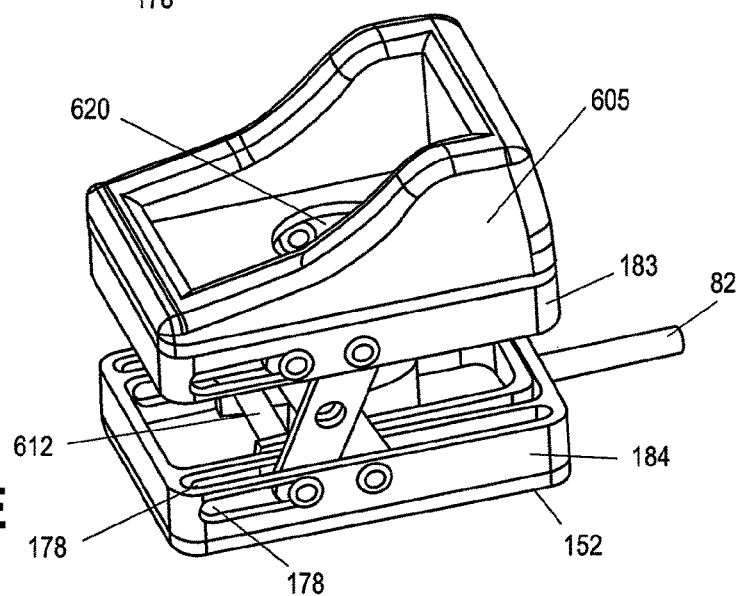

FIGS. 49A-49B illustrate another alterative of a tactile feedback mechanism in an open or expanded state (FIG. 49A) and a closed state (FIG. 49B). FIGS. 49C-49E illustrate the various views of the internal mechanisms of the devices in FIGS. 49A and 49B.

The FIGS. 49A and 49B illustrate isometric views of an over the trigger tactile feedback mechanism 600 in a raised and lowered condition, respectively. The over trigger tactile feedback mechanism 600 has a trigger adapter 605 attached to the first platform 183. A modified trigger seed text and is adapted to engage with the trigger 52. The modified trigger seed fits within and is movable relative to the trigger adapter 605. A scissor mechanism 155 is provided as before to move the first platform and the second platform.

The relative positions of the platforms in views illustrate how in the collapsed condition the modified trigger seat 610 is raised above the trigger adapter 605. In contrast, in the raised condition the modified trigger seat 610 is withdrawn within and below the upper surfaces of the trigger adapter 605.

FIG. 49C is an isometric view of the scissor mechanism 155 in a raised condition with the upper platform and the trigger adapter removed. FIG. 40 9D is similar to the view of FIG. 40 9C with the upper platform 183 attached to the scissor mechanism 155. An aperture 620 is provided in the upper platform 183. The aperture 620 used to provide coupling between the modified trigger seat 610 and the trigger 52.

Figure 50:
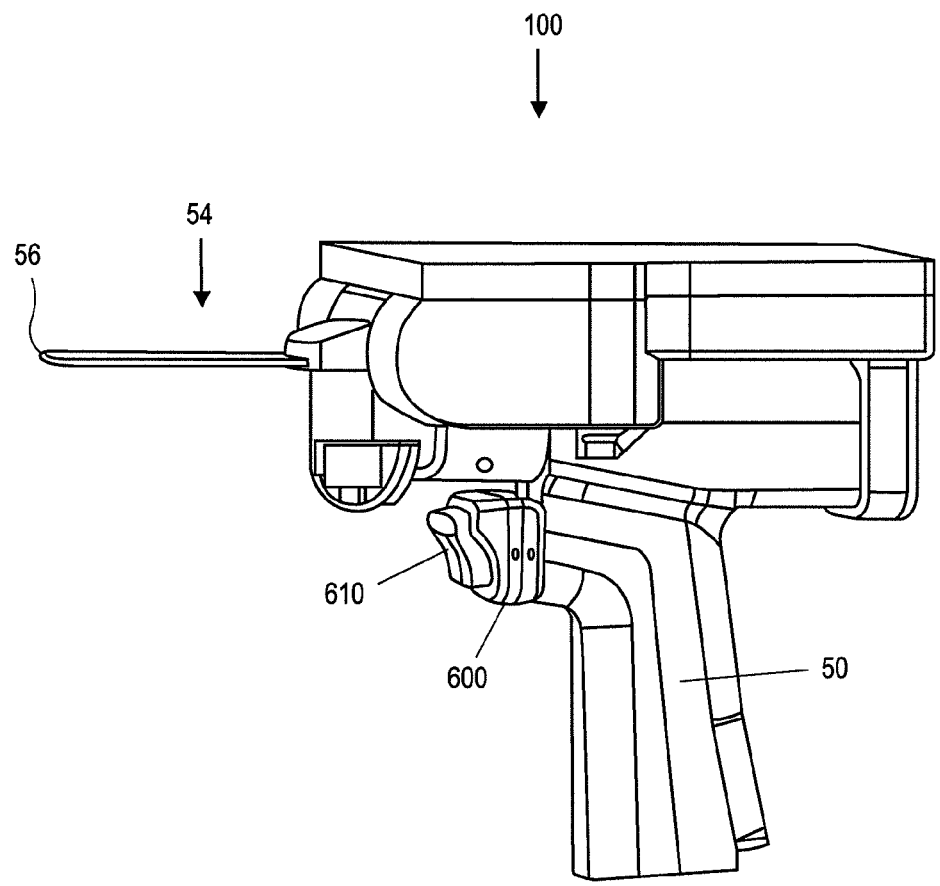
FIG. 50 illustrates an embodiment of an OTT coupled for use with a surgical tool having an embodiment of the mechanism of FIGS. 49A and 49B mounted for cooperation with the trigger of the surgical tool and configured to send and to receive trigger related with a component in the OTT.

FIG. 49E is similar to the other embodiments with the addition of the trigger adapter 605 in position on top of the first platform 183. FIG. 50 illustrates an embodiment of an OTT 100 coupled to a surgical tool 50 where the trigger 52 of the tool 50 is covered by the tactile feedback mechanism 600.

In the configuration of FIG. 50, a user's ability to manipulate the trigger 52 is covered by the operation of the tactile feedback mechanism 600.

FIG. 50 illustrates an embodiment of an OTT coupled for use with a surgical tool having an embodiment of the mechanism of FIGS. 49A and 49B mounted for cooperation with the trigger of the surgical tool and configured to send and to receive trigger related with a component in the OTT.

Figure 51:
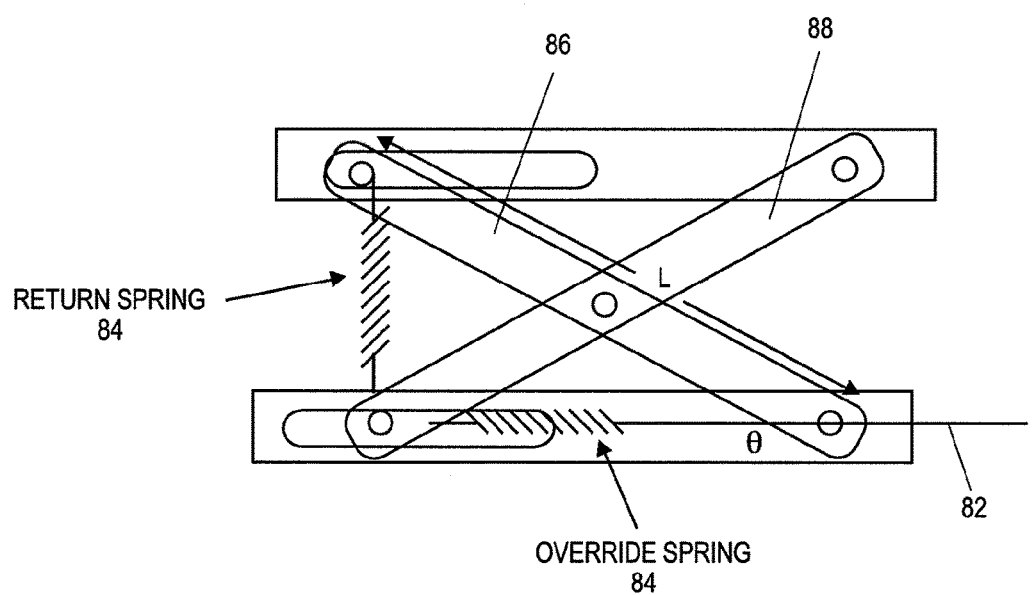
FIG. 51 is a cut away view of an alternative embodiment of a scissor mechanism utilizing two position restoration elements.

FIG. 51 is an alternative embodiment of a scissor mechanism utilizing two position restoration elements. FIG. 51 illustrates a scissor mechanism similar to FIG. 42. In contrast to the scissor mechanism of FIG. 42, the illustrated scissor mechanism in this embodiment includes a pair of position restoration elements. One position restoration element 84 is a return spring extended between the first and second platforms and coupled to the first ends of the links 86, 88. The return spring is used to modify the movement platforms and hence control trigger responsiveness. The other position restoration element is the override spring extending along the second platform. The override spring is coupled to a sliding and of the link 88 and the cable 82. The return spring in the override spring work in concert to provide a variety of different responsive features to the tactile feedback mechanism as schematically represented by FIG. 51. As a result the use of more than one in different types of position restoration element provides a wide variety of response characteristics for the tactile feedback mechanisms described herein.

Figures 52A, 52B:
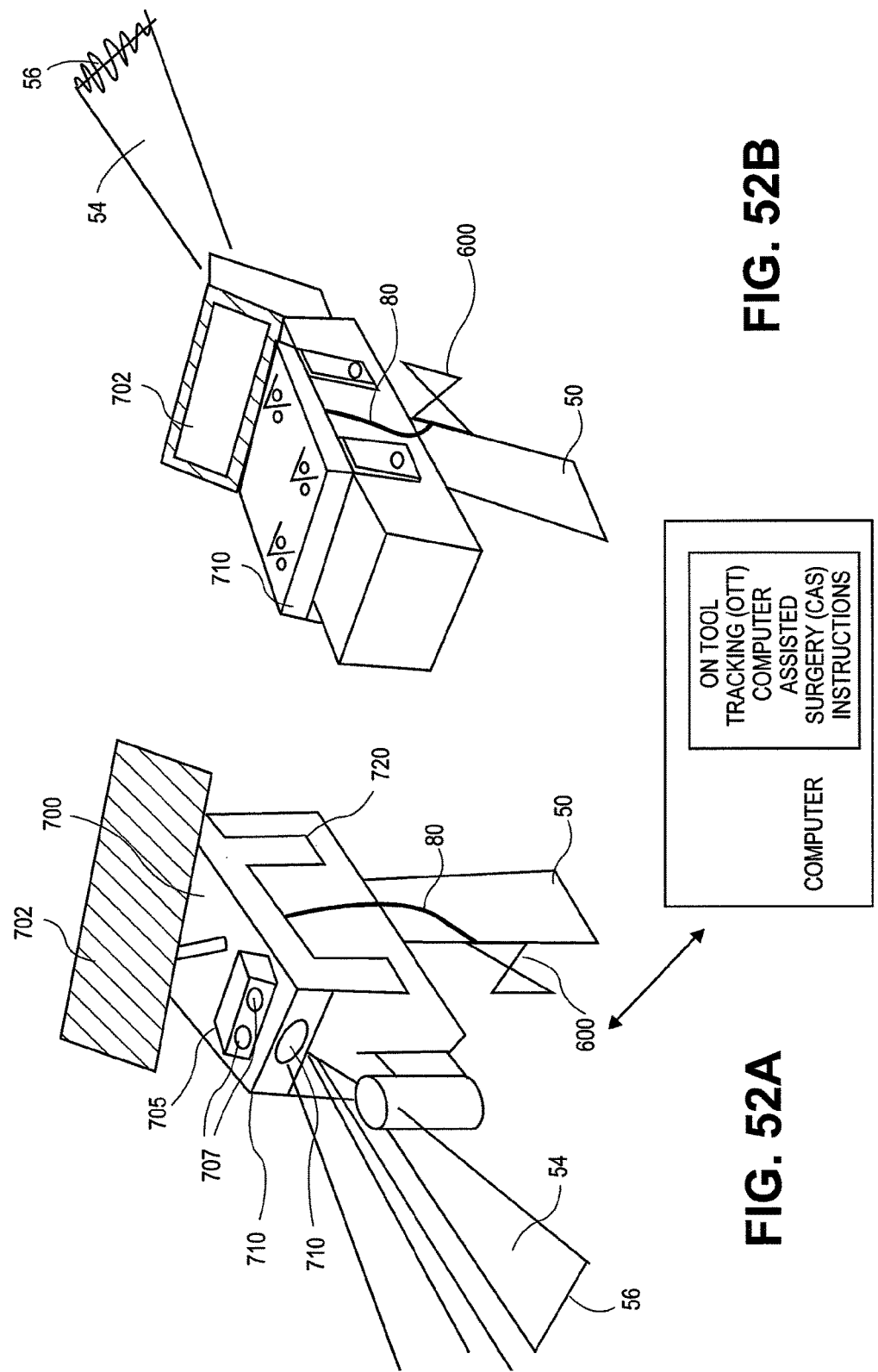
FIGS. 52A and 52B are front and rear isometric views respectively of an on tool tracking and navigation device (OTT) that includes a display with OTT housing coupled to a surgical tool having a trigger based feedback mechanism coupled to the OTT. The view also shows an exemplary computer system in communication with the OTT.

FIGS. 52A and 52B illustrate front isometric and rear isometric views, respectively, of another OTT embodiment coupled to a surgical tool 50. OTT 700 includes a housing 710 having a camera mount 705 and projector 710. In this embodiment, the camera mounts 705 is on the upper surface of the housing 710. The mount 705 contains a pair of cameras 707 directed towards the tool 74 for imaging the active element 56. In addition, this embodiment includes a TFM hundred over the trigger of the tool 50. The cable 80 provides an interface between the TFM 600 and the OTT 700 for the various purposes of tactile feedback as described herein. The OTT 700 also includes a display 702 on the upper surface of the housing 710. The display 702 may be used to provide OTT CAS output information for the user. Additionally or alternatively, display 702 is used as a user interface for user inputs. The display 702 may be configured as a graphical user interface (GUI) or other type of computer input device. Also shown is a computer in communication with the OTT 700 for the purpose of utilizing the information obtained from the use of the OTT during a CAS procedure in furtherance of the completion of a computer aided surgery. The computer includes within an electronic memory accessible to the processing unit instructions for on tool tracking computer assisted surgery. In one embodiment, computer is included within the OTT 700 as part of the electronics package within the housing. In another embodiment, the computer is an external component configured for receiving and transmitting data related to OTT CAS processes either wirelessly or via a wired connection to and from the OTT 700.

As the above examples in the illustrative embodiments make clear, embodiments of the TFM mechanisms of the present invention may be adapted or configured to provide outputs related to trigger movement or position or for further processing by the OTT CAS computer. The various TFM mechanisms provided herein may be used to provide in a minimally intrusive manner an indication of tool operation, characteristics or parameters (speed, position, rotation, setting, power level and the like) for use by the OTT CAS system. An output from a tactile feedback mechanism may be provided via an encoder/reader in the mechanism, in the OTT device, or mounted on the surgical tool itself. Still further, feedback mechanism embodiments may include wireless communications for transmitting tactile feedback mechanism information or trigger information for further processing in the OTT device or the OTT CAS computer. In a still further aspect, one or more components of the tactile feedback mechanism may be driven under instructions received based on OTT CAS processes, modes or algorithms. In some embodiments, tactile feedback mechanism indications and data are used to provide a dynamic real-time feedback loop from the OTT CAS system. Indications from the tactile feedback mechanism may also be used to provide the automatic control of one or more surgical tool control features such as: the tools motor, actuator attenuating its motor/cutting/drilling action speed or stopping it as part of an appropriate OTT CAS processing output. In one aspect, the feedback loop control is provided based on a determination of the OTT CAS system that automatic intervention of surgical tool functionality is needed to prevent an improper cut, or harm to an anatomical structure within the OTT CAS surgical field.

In still further aspects, embodiments of the tactile feedback mechanism or other feedback mechanisms configured to utilize the outputs from the systems and methods described herein may be used to automatically or semi-automatically control one or more operating characteristics of an active element of a surgical tool utilizing an on tool tracking device. Still further an embodiment of the OTT CAS system may also be configured to control the operation of the surgical tool in response to a determination of the position of the surgical tool relative to the desired boundary. Specifically, if the system determines that the tool is positioned within the tissue to be resected that is not proximate the boundary (i.e. in the green zone), the system may allow the surgical tool to controlled as desired by the surgeon. If the system determines that the tool is positioned within the tissue to be resected that is proximate the boundary (i.e. the yellow zone), the system may reduce or attenuate the operation of the surgical tool. For instance, if the tool is a saw, and it enters the yellow zone, the system may slow down the reciprocation or revolution of the saw as it moves proximate the resection boundary. Further still, if the system detects that the tool is positioned at the boundary or on tissue that is not to be resected or operated on, the system may control the surgical tool by completely stopping the tool. Although the system may automatically control the operation of the surgical tool, the system includes an override function that allows the surgeon to override the control of the tool. In this way, if the surgeon determines that a portion of tissue should be resected that was not identified for resection during the pre-operative analysis; the surgeon can override the system and resect the tissue during the procedure.

Embodiments of the tactile feedback mechanism include a wide variety of tactile stimulus. For example, the stimulus could be as simple as enhanced vibration to indicate deviation of the surgical path from the intended resection. Tactile stimulus provides the opportunity for more sophisticated indications in accordance with the various modifications and outputs provided by the OTT CAS methods described herein.

In general, powered surgical tools are activated by means of a trigger and embodiments of the feedback based mechanisms described herein provide detectable and variable (increases and decreases under control of the OTT CAS computer) resistance on the trigger or pressure on the surgeon's finger actuating the tool in a manner to indicate to the surgeon when the surgical path or current use of the active element deviates from the intended resection or other action according to the OTT CAS surgical plan. It is to be appreciated that the variety of different configurations for providing tactile feedback may be used with an unmodified, modified or replaced trigger for actuating the surgical tool used with an OTT device. In some various alternative embodiments, a trigger based feedback assembly includes a dynamic member coupled to a scissor mechanism that is in turn coupled to a stationary base (usually mounted on the handle of the surgical tool. The position or stiffness of the assembly, typically as a result of interaction with a transmission shaft or cable is dictated by a control unit within the OTT. The control unit may be configured to provide a wide variety of OTT related feedback functions including, by way of example, an actuator to operate the transmission shaft which in turn changes the force to close the scissor mechanism, moves the trigger mechanism to a full extended position, move the trigger mechanism to a full contracted position, move to a position to impair operation of the trigger, or, optionally to stop operation of the active element of the tool. In one aspect, the transmission shaft or cable or element is Bowden cable. In still other embodiments, the transmission shaft that couples the scissor mechanism to the associated component in the OTT may be any suitable element such as a rod, spring, solenoid, chain, gear, or a mini pneumatic or hydraulic actuated system. Still further, it is to be appreciated that the actuator used for the controls described above may also be included within the feedback mechanism in proximity to the trigger. In one alternative of this aspect, the actuator may be connected to the OTT device via a wired or wireless connection to provide the appropriate OTT CAS process control signals to the actuator in furtherance of the above described OTT CAS techniques.

The control unit is also capable of receiving data from the computer system. When the system determines a deviation in excess of a specified threshold level exists between the surgical path and the surgical plan by comparing the position of the tool to the intended resection of the surgical plan, the control unit actuates the transmission, increasing the resistance required to pull the trigger. Indication can be provided in the form of preventing the depression of the trigger so that the surgeon cannot activate the tool. Alternatively, indication can take the form of increased resistance, which the surgeon can overcome by the application of more force.

FIGS. 52A and 52B are front and rear isometric views respectively of an on tool tracking and navigation device (OTT) that includes a display with OTT housing coupled to a surgical tool having a trigger based feedback mechanism coupled to the OTT. The view also shows an exemplary computer system in communication with the OTT.

FIG. 36 is a flowchart representing an exemplary OTT CAS process including modification of any of the above described OTT CAS processes to include associated surgical tool operational characteristics, parameters or other data related to the use of an active element in any OTT CAS process or procedure. The OTT CAS process 3600 includes many of the same processing steps described above with regard to OTT CAS process 3100 in FIG. 31A. process Notwithstanding, any element of the indicator subsystem could readily be used for any approach to computer assisted surgery wherein the computer assisted surgery system establishes both the location of the tool in three dimensions and calculates where, according to a surgical plan, the surgeon intends to make a resection. In one alternative aspect, the methods, systems and procedures described herein are modified to incorporate one or more of the techniques, devices or methods described in U.S. Non Provisional patent application Ser. No. 11/764,505 filed on Jun. 18, 2007 and published as US 2008/0009697 entitled "Method and Apparatus for Computer Aided Surgery," the entirety of which is incorporated herein for all purposes.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. An on tool tracking and guidance device, comprising:
a housing having a surface for releasable engagement with a portion of a hand held surgical tool;
a display on the housing;
a first camera and a second camera in an arrangement within the housing on either side of a central longitudinal axis of the housing whereby each of the first camera and the second camera provide an image output containing an extracorporeal surgical field selected for a computer assisted surgery procedure;
an electronic image processor within the housing configured to receive the image output from each of the first and second cameras and perform an image processing operation using the image output from each of the first and second cameras to provide an image guided navigation output for use in the computer assisted surgery procedure and;
a projector within the housing positioned to provide an output visible within the extracorporeal surgical field containing information related to the image guided navigation output for use in the computer assisted surgery procedure.

2. The device of claim 1 wherein a field of view of the first camera and a field of view the second camera are from 70 mm to 200 mm from the first and second cameras.

3. The device of claim 1 wherein a field of view of the first camera and a field of view the second camera are from 50 mm to 250 mm from the first and second cameras.

4. The device of claim 1 wherein the surface for releasable engagement with the portion of the hand held surgical tool is shaped to form a complementary curve with the portion of the hand held surgical tool selected for engagement with the housing.

5. The device of claim 1 wherein a visual axis of the first camera and a visual axis of the second camera are inclined at an angle of between 0° to 20° relative to the central longitudinal axis of the housing.

6. The device of claim 1 wherein the projector output is projected from the housing so as to appear within the extracorporeal surgical field in front of an active element of the hand held surgical tool when the hand held surgical tool attached to the housing.

7. The device of claim 1 wherein the projector output is projected from the housing so as to appear within the extracorporeal surgical field on or near an active element associated with the hand held surgical tool when the hand held surgical tool is attached to the housing.

8. The device of claim 1 wherein the projector output is adapted for projection on a portion of the patient's anatomy, or on or within a surgical field surface in a surgical scene.

9. The device of claim 8 wherein the portion of the patient's anatomy is a bone.

10. The device of claim 8 wherein the adapted projector output is adjusted for the curvature, roughness or condition of the patient's anatomy.

11. The device of claim 1 wherein the projector is positioned in the housing above a horizontal plane that contains the first camera and the second camera.

12. The device of claim 1 wherein the projector is positioned in the housing below a horizontal plane that contains the first camera and the second camera.

13. The device of claim 1 wherein the display is configured to provide a visual output comprising information related to the image guided navigation output for use in the computer assisted surgery procedure.

14. The device of claim 1 wherein the display is a touch screen configured as an input device for the on tool tracking and guidance device.

15. The device of claim 1 wherein the projector is positioned within the housing on an inclined base.

16. The device of claim 1 wherein the projector is a pico projector.

17. The device of claim 1 wherein the projector output visible within the extracorporeal surgical field is provided in the form of laser.

18. The device of claim 1 wherein the surface for releasable engagement is selected so that when the on tool tracking and guidance device is engaged and in use with the hand held surgical tool, the first and second cameras and the projector are positioned above an active element of the hand held surgical tool.

19. The device of claim 1 wherein the surface for releasable engagement is selected so that when the on tool tracking and guidance device is engaged and in use with the hand held surgical tool, the cameras and the projector are positioned below or to one side of an active element of the hand held surgical tool.

20. The device of claim 1 further comprising:
a communication element within the housing configured to provide information related to the image guided navigation output to a component separate from the housing.

21. The device of claim 20 wherein the communication element provides information wirelessly to and from the component separate from the housing.

22. The device of claim 20 wherein the communication element provides information via a wired connection to the component separate from the housing.

23. The device of claim 20 wherein the component separate from the housing is a computer containing instructions in computer readable media related to the use of the image guided navigation output for use in the computer assisted surgery procedure.

24. The device of claim 1 further comprising:
a communication element within the housing configured to receive and provide instructions to the projector to produce the projector output visible within the extracorporeal surgical field, the projector output further comprising at least one visually perceptible indication related to a computer assisted surgery processing step performed using the image guided navigation output from the electronic image processor.

* * * * *